United States Patent
Zhu et al.

(10) Patent No.: US 10,421,753 B2
(45) Date of Patent: Sep. 24, 2019

(54) RAD51 INHIBITORS AND USES THEREOF

(71) Applicant: THE REGENTS OF THE UNIVERSITY OF CALIFORNIA, Oakland, CA (US)

(72) Inventors: Jiewen Zhu, Irvine, CA (US); Wen-Hwa Lee, Newport Coast, CA (US); Hongyuan Chen, Irvine, CA (US); Xuning Guo, Irvine, CA (US); Xiao-Long Qiu, Haimen (CN)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/554,829

(22) PCT Filed: Mar. 1, 2016

(86) PCT No.: PCT/US2016/020269
§ 371 (c)(1),
(2) Date: Aug. 31, 2017

(87) PCT Pub. No.: WO2016/140971
PCT Pub. Date: Sep. 9, 2016

(65) Prior Publication Data
US 2018/0057483 A1 Mar. 1, 2018

Related U.S. Application Data

(60) Provisional application No. 62/126,887, filed on Mar. 2, 2015.

(51) Int. Cl.
| | | |
|---|---|---|
| *C07D 417/04* | (2006.01) |
| *C07D 401/04* | (2006.01) |
| *C07D 403/04* | (2006.01) |
| *C07D 209/44* | (2006.01) |
| *C07D 223/16* | (2006.01) |
| *C07D 471/04* | (2006.01) |
| *C07D 277/56* | (2006.01) |

(52) U.S. Cl.
CPC ......... *C07D 417/04* (2013.01); *C07D 209/44* (2013.01); *C07D 223/16* (2013.01); *C07D 277/56* (2013.01); *C07D 401/04* (2013.01); *C07D 403/04* (2013.01); *C07D 471/04* (2013.01)

(58) Field of Classification Search
CPC .. C07D 401/04; C07D 217/22; C07D 217/08; C07D 417/04; A61K 31/55
See application file for complete search history.

(56) References Cited

U.S. PATENT DOCUMENTS

| | | | | |
|---|---|---|---|---|
| 8,293,764 B2 * | 10/2012 | Lee | .......... | A61K 31/4725 514/311 |
| 9,012,455 B2 * | 4/2015 | Lee | .......... | A61K 31/4745 514/252.18 |
| 2005/0070570 A1 | 3/2005 | Garcia et al. | | |
| 2011/0144209 A1 * | 6/2011 | Zachar | .......... | A61F 7/00 514/616 |

FOREIGN PATENT DOCUMENTS

WO   2007120726   10/2007

OTHER PUBLICATIONS

Qi, Tetrahedron: Asymmetry, vol. 21, 429-436, 2010. (Year: 2010).*
Hesp, Org Lett, vol. 14, No. 9, 2304-2307, 2012. (Year: 2012).*
Zhang, Tetranderon, vol. 68, 5263-5268, 2012. (Year: 2012).*
Dong, Synthetic COmm, VOI 42, 2806-2817, 2012. (Year: 2012).*
Pingaew, Arch Pharm Res, VOI 36, 1066-1077, 2013. (Year: 2013).*
Janody, J Org Chem, vol. 79, 5673-5683, 2014. (Year: 2014).*
Zhu, E Je Med Chem, VOI 96, 196-208, 2015. (Year: 2015).*
Smusz, Bioorg & Med Chem Letters, vol. 25, 1827-1830, 2015. (Year: 2015).*
Qiu et al. "Stereoselective Synthesis of Chiral IBR2 Analogues" J. Org. Chem. 2007, vol. 74, No. 5, pp. 2018-2027.
Pingaew et al. "Synthesis, cytotoxicity and QSAR study of N-tosyl-1,2,3,4-tetrahydroisoquinoline derivatives" Arch. Pharm. Res. 2013, vol. 36, No. 9, pp. 1066-1077.
Zhu et al., "Efficient and Practical Syntheses of Enantiomerically Pure (S)-(−)-Norcryptostyline I, (S)-(−)- Norcryptostyline II, (R)-(+)-Salsolidine and (S)-(−)-Norlaudanosine via a Resolution-Racemization Method" Chinese J. Journal of Chemistry, 2014, vol. 32, Issue 10, pp. 1039-1048.
Zhu et al., "A novel small molecule RAD51 inactivator overcomes imatinib-resistance in chronic myeloid leukaemia" 2013, EMBO Mol. Med. 5:1-13.
Pierce et al., "XRCC3 promotes homology-directed repair of DNA damage in mammalian cells" 1999, Genes Dev. 13:2633-2638.
Wang et al., "Asymmetric Friedel-Crafts Reaction of Indoles with Imines by an Organic Catalyst" 2006, J. Am. Chem. Soc. 128:8156-8157.
Pellegrini et al., "Insights into DNA recombination from the structure of a RAD51-BRCA2 complex" 2002, Nature 420:287-293.

* cited by examiner

*Primary Examiner* — D Margaret M Seaman
(74) *Attorney, Agent, or Firm* — Riverside Law LLP

(57) ABSTRACT

The present invention includes novel RAD51 inhibitors. The compounds of the invention may be useful in preventing or treating cancer in a subject in need thereof. The present invention also includes methods of preventing or treating cancer in a subject in need thereof by administering to the subject a therapeutically effective amount of a compound of the invention.

21 Claims, 18 Drawing Sheets

RAD51 INHIBITORS AND USES THEREOF

CROSS REFERENCE TO RELATED APPLICATIONS

The present application is the U.S. National Stage Application filed under 35 U.S.C. § 371 of International Patent Application No. PCT/US2016/020269, filed Mar. 1, 2016, which is entitled to priority under 35 U.S.C. § 119(e) to U.S. Provisional Patent Application No. 62/126,887, filed Mar. 2, 2015, the entire disclosures of all of which are incorporated by reference herein as if set forth herein in their entireties.

STATEMENT REGARDING FEDERALLY SPONSORED RESEARCH OR DEVELOPMENT

This invention was made in part with U.S. Government support under Grant No. CA107568, awarded by the National Institutes of Health. The U.S. Government has certain rights in this invention.

BACKGROUND OF THE INVENTION

RAD51 is essential for DNA repair, proliferation and survival of cells. RAD51 protein level is elevated in many cancer cells, contributing to their resistance to chemotherapy and the continuous cell proliferation (Flygare et al., 2001, Exp. Cell Res. 268:61-69; Chen et al., 1999, J. Biol. Chem. 274:32931-32935; Chen et al., 1998, Proc. Natl. Acad. Sci. USA 95:5287-5292; Klein, 2008, DNA Repair 7:686-693; Maacke et al., 2000, Oncogene 19:2791-2795; Qiao et al., 2005, Br. J. Cancer 93:137-143; Raderschall et al., 2002, Cancer Res. 62:219-225; richerdson et al., 2004, Oncogene 23:546-553; Robu et al., 2001, Proc. Natl. Acad. Sci. USA 98:8211-8218; Slupianek et al., 2001, Mol. Cell 8:795-806). Targeting RAD51 is therefore an attractive strategy for treating difficult-to-treat cancers, such as triple negative breast cancers, which are often easy to metastasize and difficult to treat (Hudis et al., 2011, Oncologist 16:1-11; Peddi et al., 2012, Int. J. Breast Cancer 2012:1-7) as they known to be resistant to most common therapeutics. Recently, a small molecule RAD51 inhibitor (Zhu et al., 2013, EMBO Mol. Med. 5:1-13), designated as IBR2, was identified and validated. RAD51 was rapidly degraded in IBR2-treated cancer cells, and the homologous recombination repair was impaired, subsequently leading to cell death. However, the $IC_{50}$ values of IBR2 were only in the range of 12-20 μM for most tested cancer cell lines.

There is a need in the art for novel RAD51 inhibitors with improved potency. The present invention addresses this unmet need.

SUMMARY OF THE INVENTION

The present invention includes a compound selected from the group consisting of formula (I), formula (II), and formula (III), a salt or solvate, and any combinations thereof:

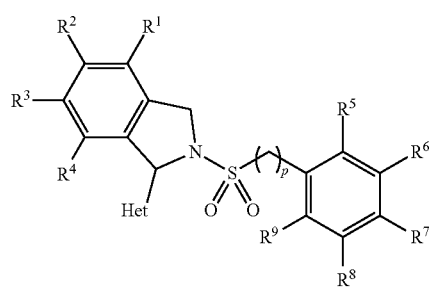

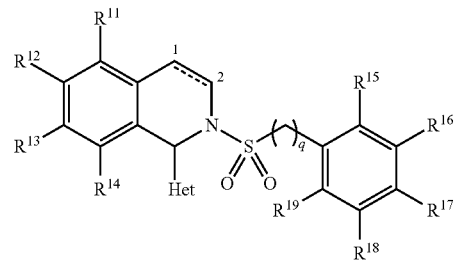

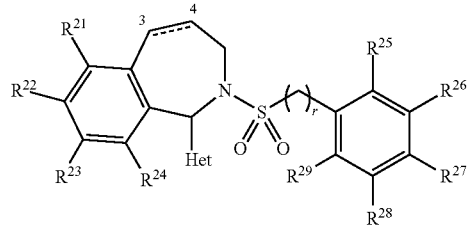

wherein:

$R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{27}$, $R^{28}$, and $R^{29}$ are each independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{30}$, $SR^{30}$, $S(=O)R^{30}$, $S(=O)_2R^{30}$, $NHS(=O)_2R^{30}$, $C(=O)R^{30}$, $OC(=O)R^{30}$, $CO_2R^{30}$, $OCO_2R^{30}$, $CH(R^{30})_2$, $N(R^{30})_2$, $C(=O)N(R^{30})_2$, $OC(=O)N(R^{30})_2$, $NHC(=O)NH(R^{30})$, $NHC(=O)R^{30}$, $NHC(=O)OR^{30}$, $C(OH)(R^{30})_2$, and $C(NH_2)(R^{30})_2$;

each occurrence of $R^{30}$ is independently selected from the group consisting of H and $C_1$-$C_6$ alkyl;

Het is a 5- to 14-membered substituted or unsubstituted heteroaryl ring;

the bond between carbon 1 and carbon 2 may be a single bond or a double bond;

the bond between carbon 3 and carbon 4 may be a single bond or a double bond;

p is an integer from 0-3;

q is an integer from 0-3; and r is an integer from 0-3, with the proviso that in a compound of formula (II), if $R^{11}$, $R^{12}$, $R^{13}$, $R^{14}$, $R^{15}$, $R^{16}$, $R^{17}$, $R^{18}$, and $R^{19}$ are all H, the bond between carbon 1 and carbon 2 is a double bond, and q is 1, then Het cannot be 3-indolyl.

In one embodiment, the compound is a compound of formula (I). In another embodiment, the compound is a compound of formula (II). In another embodiment, the compound is a compound of formula (III). In another embodiment, $R^1$, $R^2$, $R^3$, $R^4$, $R^5$, $R^6$, $R^7$, $R^8$, and $R^9$ are each H. In another embodiment, $R^{11}$, $R^{12}$, $R^{13}$, $R^{14}$, $R^{15}$, $R^{16}$, $R^{17}$, $R^{18}$, and $R^{19}$ are each H. In another embodiment, $R^{15}$ is selected from the group consisting of H, F, and $CF_3$. In another embodiment, $R^{16}$ is selected from the group consisting of H, F, and $CF_3$. In another embodiment, $R^{17}$ is selected from the group consisting of H, F, and $CF_3$. In another embodiment, $R^{21}$, $R^{22}$, $R^{23}$, $R^{24}$, $R^{25}$, $R^{26}$, $R^{27}$, $R^{28}$, and $R^{29}$ are each H. In another embodiment, Het is selected from the group consisting of indolyl, azaindolyl, and thiazolyl, wherein the indolyl, azaindolyl, or thiazolyl group may be optionally substituted. In another embodiment, Het is selected from the group consisting of:

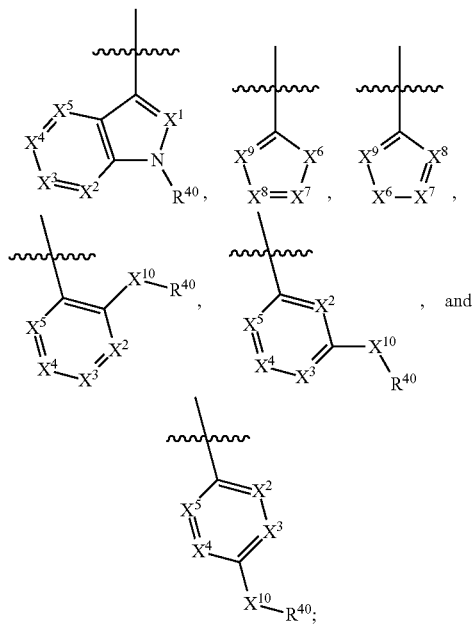

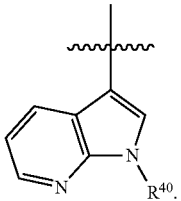

In one embodiment, p is 1. In another embodiment, q is 1. In another embodiment, r is 1.

In one embodiment, the compound is selected from the group consisting of:

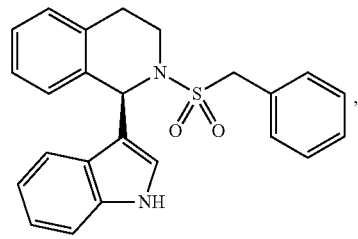

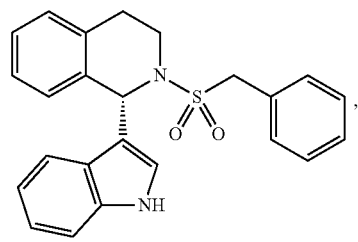

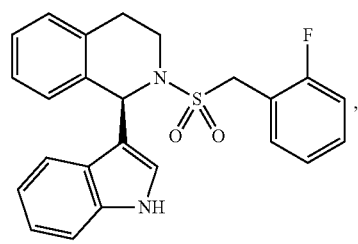

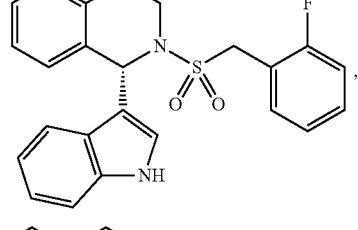

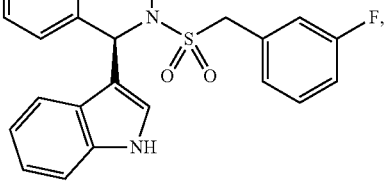

wherein $X^1$, $X^2$, $X^3$, $X^4$, $X^5$, $X^7$, $X^8$, and $X^9$ are each independently selected from the group consisting of N and $CR^{41}$;

$X^6$ and $X^{10}$ are each independently selected from the group consisting of S, O, $C(R^{42})_2$, and $NR^{43}$;

each occurrence of $R^{40}$, $R^{41}$, $R^{42}$, and $R^{43}$ is independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{44}$, $SR^{44}$, $S(=O)R^{44}$, $S(=O)_2R^{44}$, $NHS(=O)_2R^{44}$, $C(=O)R^{44}$, $OC(=O)R^{44}$, $CO_2R^{44}$, $OCO_2R^{44}$, $CH(R^{44})_2$, $N(R^{44})_2$, $C(=O)N(R^{44})_2$, $OC(=O)N(R^{44})_2$, $NHC(=O)NH(R^{44})$, $NHC(=O)R^{44}$, $NHC(=O)OR^{44}$, $C(OH)(R^{44})_2$, and $C(NH_2)(R^{44})_2$; and each occurrence of $R^{44}$ is independently selected from the group consisting of H and $C_1$-$C_6$ alkyl. In another embodiment, $X^6$ is S. In another embodiment, $X^8$ is $NR^{41}$. In another embodiment, $X^1$ is $NR^{41}$. In another embodiment, $X^2$ is $NR^{41}$. In another embodiment, $X^3$ is $NR^{41}$.

In one embodiment, Het is selected from the group consisting of:

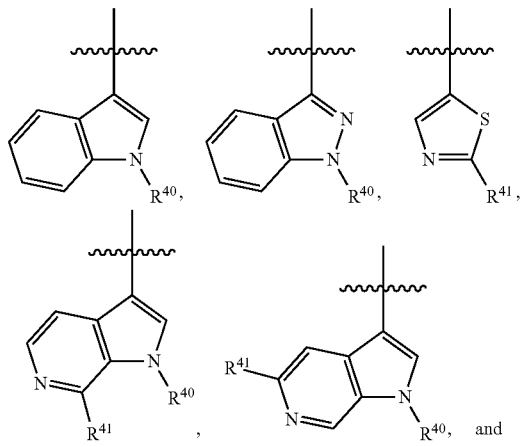

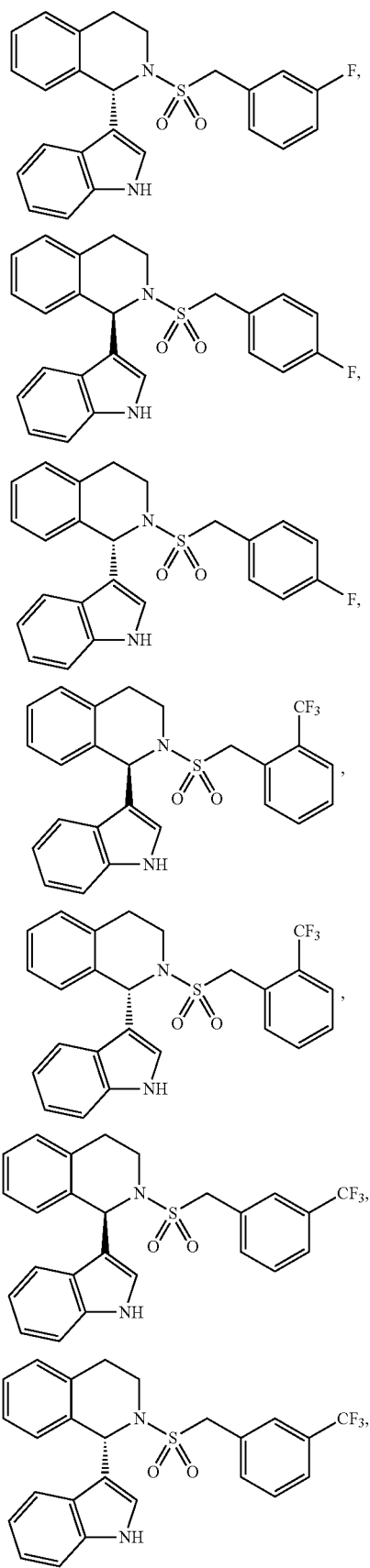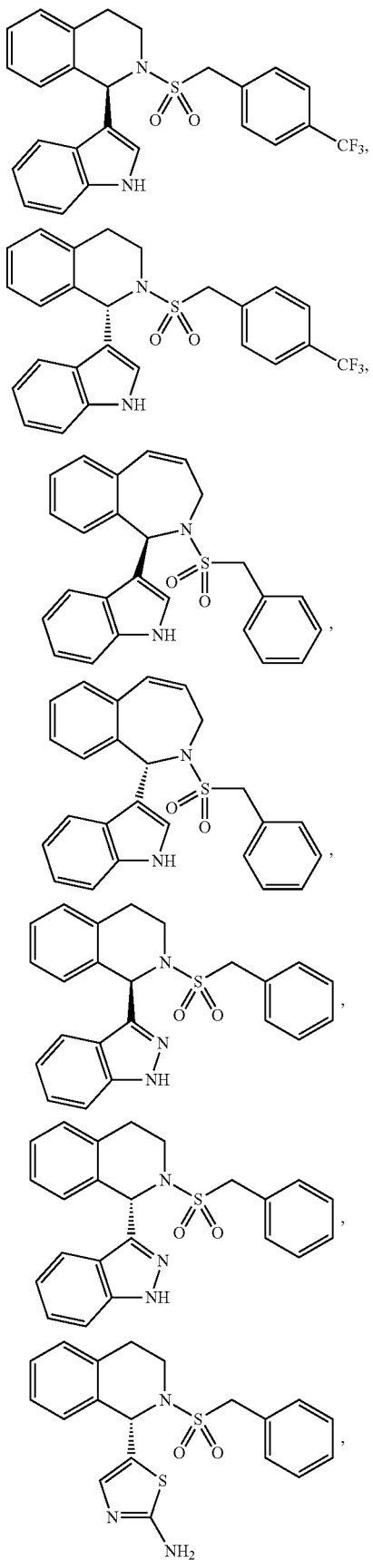

-continued

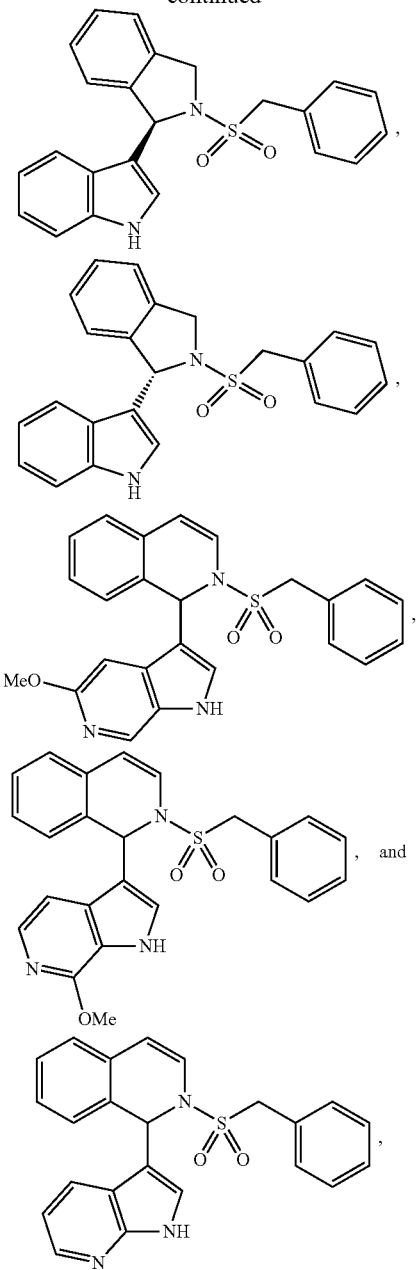

a salt or solvate, and any combinations thereof.

In one embodiment, the compound is:

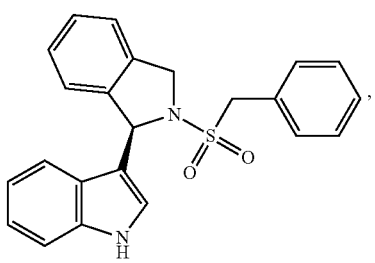

a salt or solvate, and any combinations thereof.

The present invention also includes a pharmaceutical composition comprising at least one compound of the invention.

The present invention also includes a method of preventing or treating cancer in a subject in need thereof. The method includes administering to the subject a therapeutically effective amount of a composition comprising a compound selected from the group consisting of formula (I), formula (II), and formula (III), a salt or solvate, and any combinations thereof:

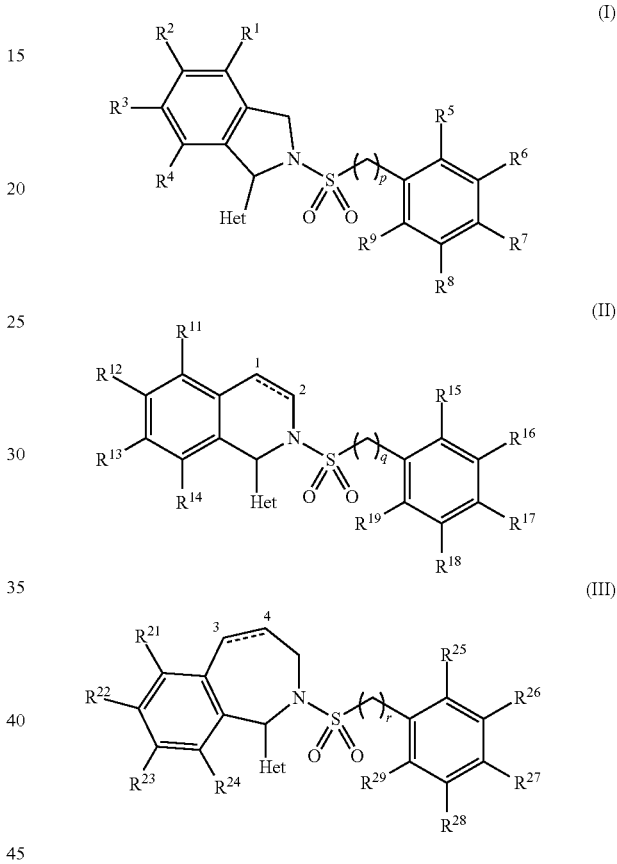

wherein:
$R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{27}$, $R^{28}$, and $R^{29}$ are each independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{30}$, $SR^{30}$, $S(=O)R^{30}$, $S(=O)_2R^{30}$, $NHS(=O)_2R^{30}$, $C(=O)R^{30}$, $OC(=O)R^{30}$, $CO_2R^{30}$, $OCO_2R^{30}$, $CH(R^{30})_2$, $N(R^{30})_2$, $C(=O)N(R^{30})_2$, $OC(=O)N(R^{30})_2$, $NHC(=O)NH(R^{30})$, $NHC(=O)R^{30}$, $NHC(=O)OR^{30}$, $C(OH)(R^{30})_2$, and $C(NH_2)(R^{30})_2$;

each occurrence of $R^{30}$ is independently selected from the group consisting of H and $C_1$-$C_6$ alkyl;

Het is a 5- to 14-membered substituted or unsubstituted heteroaryl ring;

the bond between carbon 1 and carbon 2 may be a single bond or a double bond;

the bond between carbon 3 and carbon 4 may be a single bond or a double bond;

p is an integer from 0-3;
q is an integer from 0-3; and
r is an integer from 0-3, with the proviso that in a compound of formula (II), if $R^{11}$, $R^{12}$, $R^{13}$, $R^{14}$, $R^{15}$, $R^{16}$, $R^{17}$, $R^{18}$, and $R^{19}$ are all H, the bond between carbon 1 and carbon 2 is a double bond, and q is 1, then Het cannot be 3-indolyl.

In one embodiment, the compound is a compound of formula (I). In another embodiment, the compound is a compound of formula (II). In another embodiment, the compound is a compound of formula (III). In another embodiment, $R^1$, $R^2$, $R^3$, $R^4$, $R^5$, $R^6$, $R^7$, $R^8$, and $R^9$ are each H. In another embodiment, $R^{11}$, $R^{12}$, $R^{13}$, $R^{14}$, $R^{15}$, $R^{16}$, $R^{17}$, $R^{18}$, and $R^{19}$ are each H. In another embodiment, $R^{15}$ is selected from the group consisting of H, F, and $CF_3$. In another embodiment, $R^{16}$ is selected from the group consisting of H, F, and $CF_3$. In another embodiment, $R^{17}$ is selected from the group consisting of H, F, and $CF_3$. In another embodiment, $R^{21}$, $R^{22}$, $R^{23}$, $R^{24}$, $R^{25}$, $R^{26}$, $R^{27}$, $R^{28}$, and $R^{29}$ are each H. In another embodiment, Het is selected from the group consisting of indolyl, azaindolyl, and thiazolyl, wherein the indolyl, azaindolyl, or thiazolyl group may be optionally substituted.

In one embodiment, Het is selected from the group consisting of:

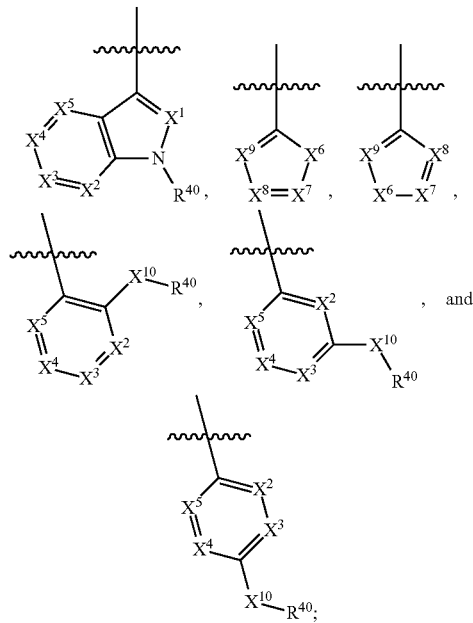

wherein $X^1$, $X^2$, $X^3$, $X^4$, $X^5$, $X^7$, $X^8$, and $X^9$ are each independently selected from the group consisting of N and $CR^{41}$;

$X^6$ and $X^{10}$ are each independently selected from the group consisting of S, O, $C(R^{42})_2$, and $NR^{43}$;

each occurrence of $R^{40}$, $R^{41}$, $R^{42}$, and $R^{43}$ is independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{44}$, $SR^{44}$, $S(=O)R^{44}$, $S(=O)_2R^{44}$, $NHS(=O)_2R^{44}$, $C(=O)R^{44}$, $OC(=O)R^{44}$, $CO_2R^{44}$, $OCO_2R^{44}$, $CH(R^{44})_2$, $N(R^{44})_2$, $C(=O)N(R^{44})_2$, $OC(=O)N(R^{44})_2$, $NHC(=O)NH(R^{44})$, $NHC(=O)R^{44}$, $NHC(=O)OR^{44}$, $C(OH)(R^{44})_2$, and $C(NH_2)(R^{44})_2$; and each occurrence of $R^{44}$ is independently selected from the group consisting of H and $C_1$-$C_6$ alkyl.

In one embodiment, $X^6$ is S. In another embodiment, $X^8$ is $NR^{41}$. In another embodiment, $X^1$ is $NR^{41}$. In another embodiment, $X^2$ is $NR^{41}$. In another embodiment, $X^3$ is $NR^{41}$ In one embodiment, Het is selected from the group consisting of:

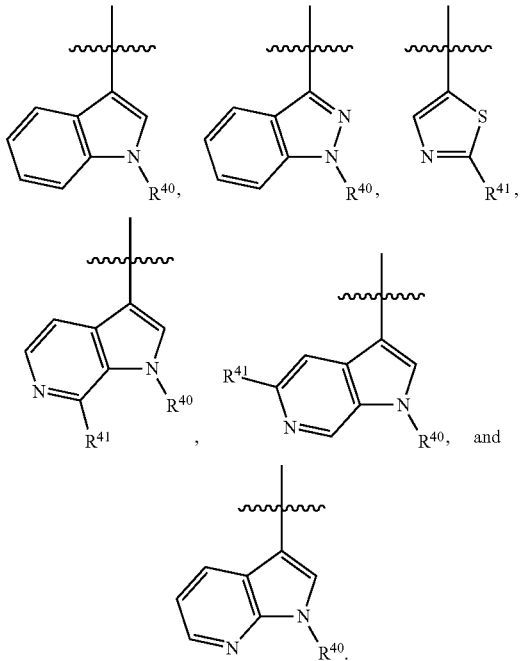

In one embodiment, p is 1. In another embodiment, q is 1. In another embodiment, r is 1.

In one embodiment, the compound is selected from the group consisting of:

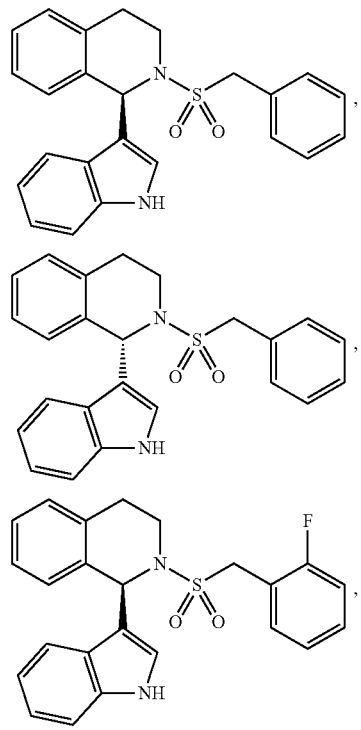

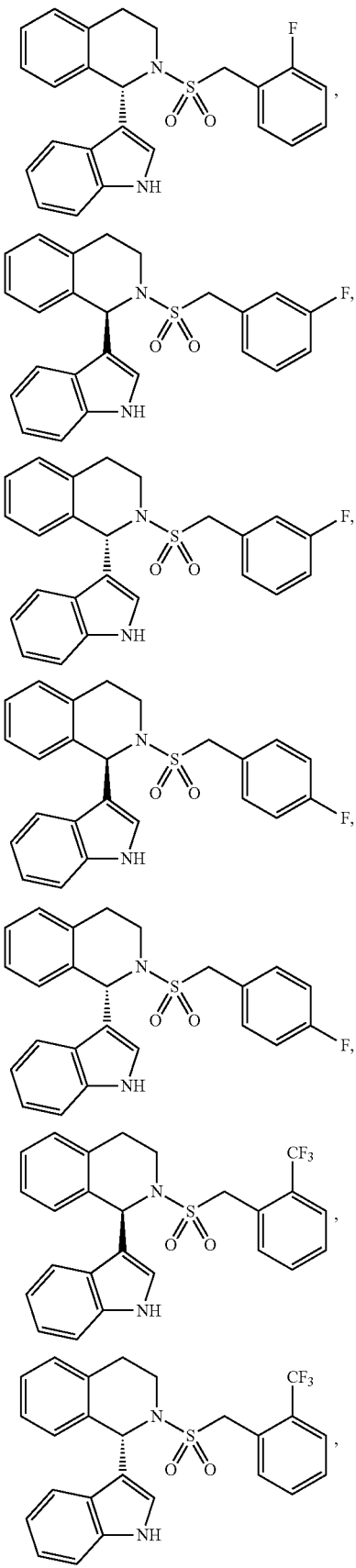
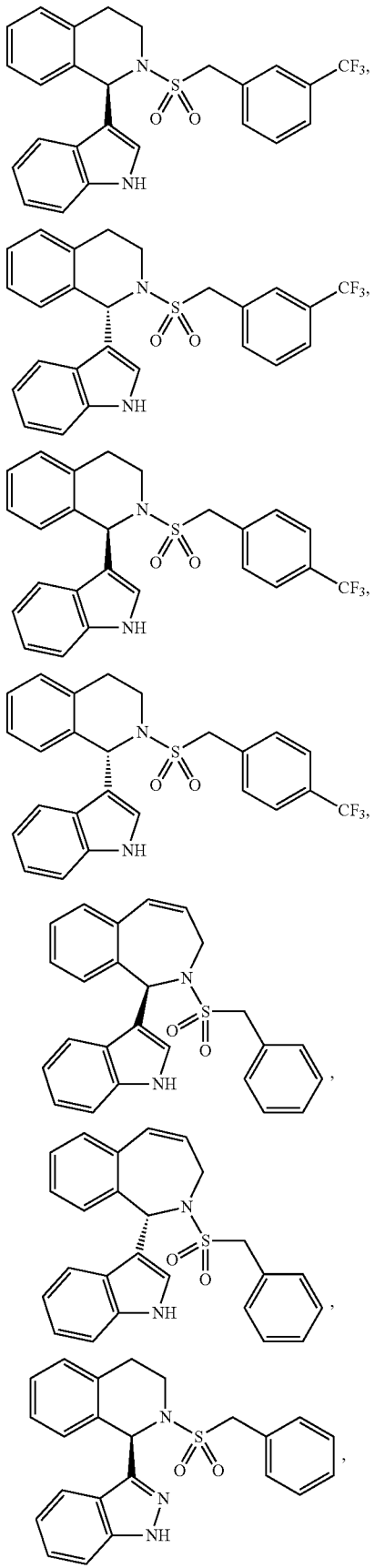

-continued

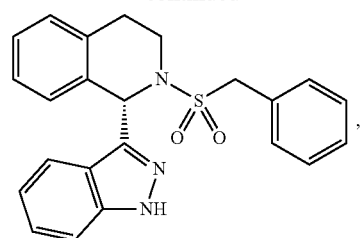

,

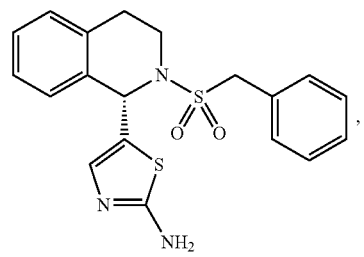

,

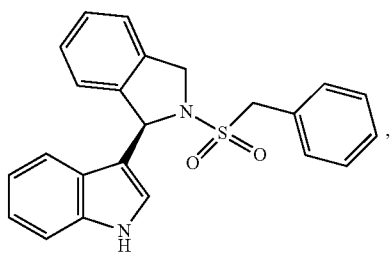

,

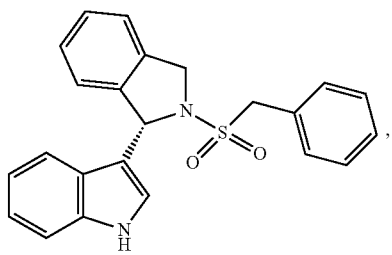

,

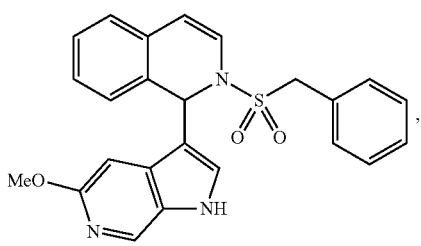

,

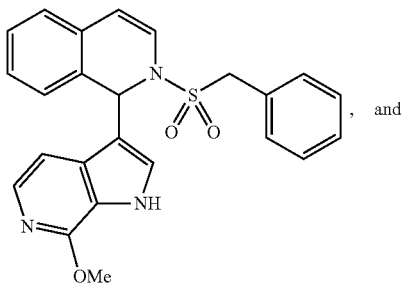

, and

-continued

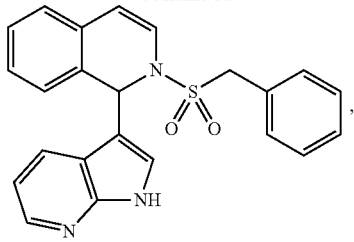

, a salt or solvate, and any combinations thereof.

In one embodiment, the compound is:

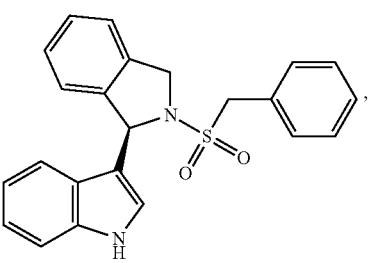 [SMILES: O=S(=O)(Cc1ccccc1)N1Cc2ccccc2[C@@H]1c1c[nH]c2ccccc12]

, a salt or solvate, and any combinations thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 9A-9B, depicts a docking model of RAD51-IBR120. FIG. 9A depicts an image of the binding conformation with lowest energy. RAD51 residues within 5 Å of docked IBR120 are labeled in cyan. Potential hydrogen bonds are labeled in dashed lines. RAD51 protein is shown as transparent surface according to hydrophobicity, with ball-and-stick model indicating docking site. FIG. 9B is a schematic of contributing intermolecular interactions between RAD51 and IBR120. Potential hydrogen bonds are shown in blue. N—H—O distances (Å) are indicated. Hydrophobic surfaces are marked with red dashed curves.

FIGS. 10A-10D, depicts an exemplary structural activity relationship of the compounds of the invention. FIG. 10A depicts experimental data demonstrating that the R-configuration has better activity than S-configuration (two-tailed t-test, p<0.01). Inset: star (*) shows the chiral center in IBR120. FIG. 10B depicts experimental data demonstrating that correlation between activity and dihedral angle in all 25 compounds. Cluster centers were obtained using K-means clustering algorithm (k=2). Inset showing the dihedral angle formed by C—C—N—S in IBR120 (shown as bold bonds). FIG. 10C depicts experimental data demonstrating the predictive multivariate linear model derived from the training set (pIC50~(6.15±1.73)−(0.02±0.01)*MolWeight−(0.45±0.12)*MolLogP−(0.20±0.05)*MolLogS+(0.01±0.01)*MolPSA+(0.018+0.005)*MolVol−(0.006±0.003)*MoldHf−(0.025±0.005)*Score+(0.0021±0.0007)*DihedralAngle−(0.08±0.06)*Chirality), Residual standard error: 0.034 on 6 degrees of freedom, Multiple R-squared: 0.984, Adjusted R-squared: 0.9599, p-value: 0.0001061. FIG. 10D depicts experimental data demonstrating the prediction result on the test sets in comparison with experimental data.

FIGS. 12A-12I, depicts experimental data demonstrating that IBR120 dose dependently inhibits HR repair. HR frequency was measured by two-colour fluorescence flow cytometric analysis using HeLa-DR-GFP cells. Fifty thousand events were analyzed for each experiment. Cells were treated with DMSO (mock), 10 or 20 μM of IBR2 or IBR120 as indicated for 24 hours after transient transfection with I-SceI expression vector pCABSce for 24 hours. HR frequencies were indicated by GFP positive cell percentages. FIG. 12A is a graph depicting experimental data demonstrating FACS analysis data for cells with no I-Sce treated with DMSO. FIG. 12B is a graph depicting experimental data demonstrating FACS analysis data for cells with no I-Sce treated with 10 μM of IBR120. DMSO. FIG. 12C is a graph depicting experimental data demonstrating FACS analysis data for cells with no I-Sce treated with 10 μM of IBR2. FIG. 12D is a graph depicting experimental data demonstrating FACS analysis data for cells with I-Sce treated with DMSO. FIG. 12E is a graph depicting experimental data demonstrating FACS analysis data for cells with I-Sce treated with 10 μM of IBR120. DMSO. FIG. 12F is a graph depicting experimental data demonstrating FACS analysis data for cells with I-Sce treated with 20 μM of IBR120. DMSO. FIG. 12G is a graph depicting experimental data demonstrating FACS analysis data for cells with I-Sce treated with 10 μM of IBR2. DMSO. FIG. 12H is a graph depicting experimental data demonstrating FACS analysis data for cells with I-Sce treated with 20 μM of IBR2. FIG. 12I is a graph depicting experimental data demonstrating a summary of HR frequency determined by FACS analysis. GFP positive cell percentages by indicated treatments obtained from three independent experiments are summarized as means±SD.

FIGS. 16A-16B, depicts experimental data demonstrating a predictive multivariate linear model without including dihedral angle and chirality as parameters. FIG. 16A is a graph of predicted and experimental data demonstrating the model derived from the training set (pIC50~(7.24±4.05)−(0.03±0.02)*MolWeight−(0.18±0.21)*MolLogP−(0.05±0.15)*MolLogS+(0.02±0.02)*MolPSA+(0.027±0.009)*MolVol−(0.0085±0.0060)*MoldHf−(0.010±0.014)*Score), Residual standard error: 0.111 on 8 degrees of freedom, Multiple R-squared: 0.7719, Adjusted R-squared: 0.5723, p-value: 0.03853. FIG. 16B is a graph of predicted and experimental data demonstrating the prediction result on the test sets in comparison with experimental data.

DETAILED DESCRIPTION OF THE INVENTION

Figure 1:
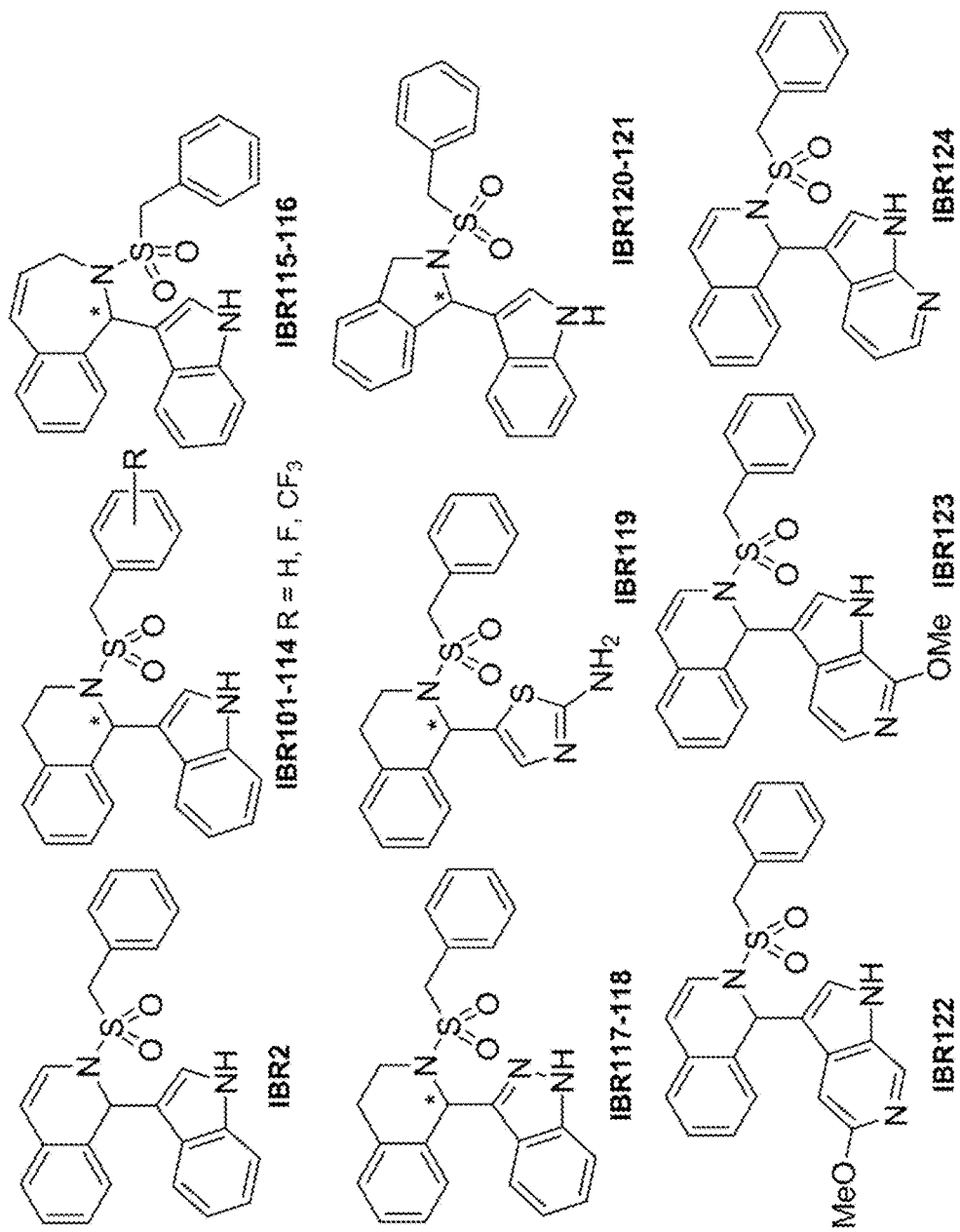
FIG. 1 depicts the structures of IBR2 and compounds IBR101-124.

The present invention relates in part to the unexpected discovery of novel RAD51 inhibitors that are useful for the treatment of cancer. As demonstrated herein, the compounds of the present invention have been shown to be effective chemotherapeutic agents for the treatment of breast cancer.

The present invention also includes novel methods of treating or preventing cancer using the compounds of the invention. In one embodiment, the cancer is selected from the group consisting of breast cancer, chronic myelogenous leukemia, osteosarcoma, glioblastoma, cervical cancer, lung cancer, colon cancer, melanoma, ovarian cancer, prostate cancer, liver cancer, pancreatic cancer, CNS tumors (including brain tumors), neuroblastoma, leukemia, bone cancer, intestinal cancer, lymphoma, and combinations thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

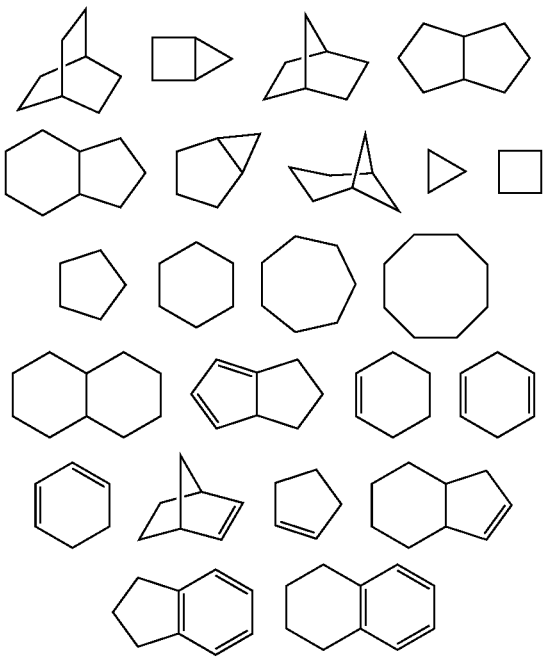

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

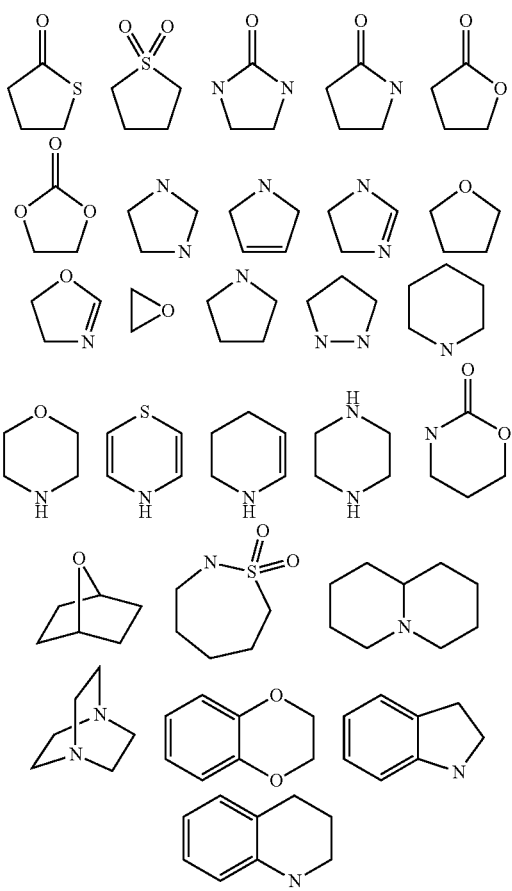

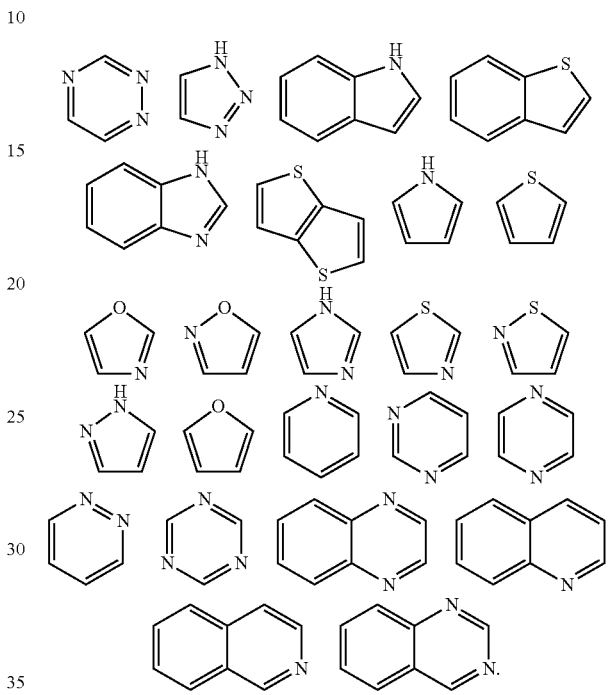

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π(pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-$(C_1-C_3)$alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-$(C_1-C_3)$alkyl" means an aryl-$(C_1-C_3)$alkyl functional group in which the aryl group is substituted. Similarly, the term "heteroaryl-$(C_1-C_3)$alkyl" means a functional group wherein a one to three carbon alkylene chain is attached to a heteroaryl group, e.g., —$CH_2CH_2$-pyridyl. The term "substituted heteroaryl-$(C_1-C_3)$alkyl" means a heteroaryl-$(C_1-C_3)$alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]2, —OC(=O)N[substituted or unsubstituted alkyl]2, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates in part to the unexpected discovery of a novel class of direct and specific RAD51 inhibitors. The compounds of the present invention exhibited 4.8-fold improvement in RAD51 inhibition over compounds of the prior art. In one embodiment, the compounds of the invention are capable of inhibiting the growth of triple-negative breast cancer cells and a panel of other malignancies. Thus, the present invention also related in part to methods for treating or prevent a disease or cancer in a subject in need thereof using the compounds of the invention.

RAD51 recombinase plays a critical role for cancer cell proliferation and survival. The IBR2 molecular scaffold contains a chiral center, and the structure-activity relationship of its chirality has not been explored to date. As described herein, novel RAD51 inhibitors, including compounds IBR101-124, were designed, synthesized, modeled, and biologically evaluated. These new compounds constitute a focused compound library representing a diversity of modified scaffold or substituents (FIG. 1).

The present invention also includes novel methods of treating or preventing cancer using the compounds of the invention. In one embodiment, the cancer is selected from the group consisting of lung cancer, colon cancer, melanoma, breast cancer, ovarian cancer, prostate cancer, liver cancer, pancreatic cancer, CNS tumors (including brain tumors), neuroblastoma, leukemia, bone cancer, intestinal cancer, lymphoma, and combinations thereof.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound selected from the group consisting of formula (I), formula (II), and formula (III), or a salt or solvate thereof, and combinations thereof:

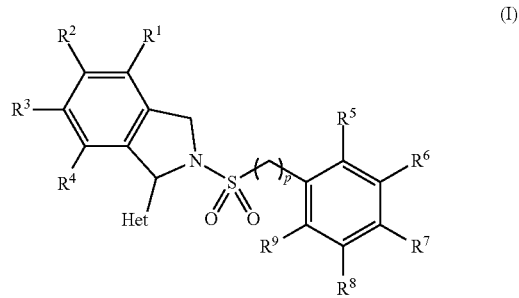

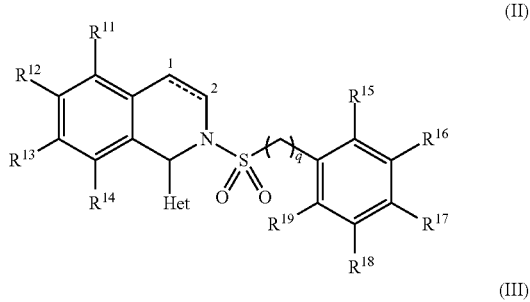

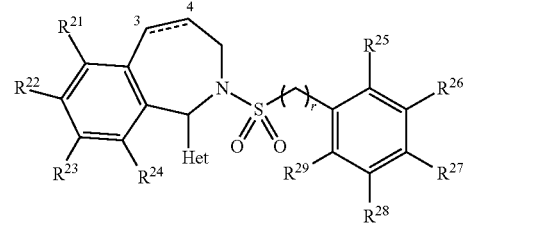

wherein:

$R^1, R^2, R^3, R^4, R^5, R^6, R^7, R^8, R^9, R^{11}, R^{12}, R^{13}, R^{14}, R^{15}, R^{16}, R^{17}, R^{18}, R^{19}, R^{21}, R^{22}, R^{23}, R^{24}, R^{25}, R^{26}, R^{27}, R^{28}$, and $R^{29}$ are each independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{30}$, $SR^{30}$, $S(=O)R^{30}$, $S(=O)_2R^{30}$, $NHS(=O)_2R^{30}$, $C(=O)R^{30}$, $OC(=O)R^{30}$, $CO_2R^{30}$, $OCO_2R^{30}$, $CH(R^{30})_2$, $N(R^{30})_2$, $C(=O)N(R^{30})_2$, $OC(=O)N(R^{30})_2$, $NHC(=O)NH(R^{30})$, $NHC(=O)R^{30}$, $NHC(=O)OR^{30}$, $C(OH)(R^{30})_2$, and $C(NH_2)(R^{30})_2$;

each occurrence of $R^{30}$ is independently selected from the group consisting of H and $C_1$-$C_6$ alkyl;

Het is a 5- to 14-membered substituted or unsubstituted heteroaryl ring;

the bond between carbon 1 and carbon 2 may be a single bond or a double bond;

the bond between carbon 3 and carbon 4 may be a single bond or a double bond;

p is an integer from 0-3;

q is an integer from 0-3; and r is an integer from 0-3, with the proviso that in a compound of formula (II), if $R^{11}$, $R^{12}$, $R^{13}$, $R^{14}$, $R^{15}$, $R^{16}$, $R^{17}$, $R^{18}$, and $R^{19}$ are all H, the bond between carbon 1 and carbon 2 is a double bond, and q is 1, then Het cannot be 3-indolyl.

In one embodiment, the compound is a compound of formula (I). In another embodiment, the compound is a compound of formula (II). In another embodiment, the compound is a compound of formula (III).

In one embodiment, $R^1$, $R^2$, $R^3$, $R^4$, $R^5$, $R^6$, $R^7$, $R^8$, and $R^9$ are each H.

In one embodiment, $R^{11}$, $R^{12}$, $R^{13}$, $R^{14}$, $R^{15}$, $R^{16}$, $R^{17}$, $R^{18}$, and $R^{19}$ are each H. In one embodiment, $R^{15}$ is selected from the group consisting of H, F, and $CF_3$. In another embodiment, $R^{16}$ is selected from the group consisting of H, F, and $CF_3$. In another embodiment, $R^{17}$ is selected from the group consisting of H, F, and $CF_3$.

In one embodiment, $R^{21}$, $R^{22}$, $R^{23}$, $R^{24}$, $R^{25}$, $R^{26}$, $R^{27}$, $R^{28}$, and $R^{29}$ are each H.

Het can be any 5- to 14-membered substituted or unsubstituted heteroaryl ring, as would be understood by one of ordinary skill in the art. In one embodiment, Het is indolyl. In another embodiment, Het is an indolyl bioisostere. Non-limiting examples of indole bioisosteres include a substituted or unsubstituted phenol or aniline group. In another embodiment, Het is azaindolyl. In another embodiment, Het is thiazolyl.

In one embodiment, Het is selected from the group consisting of:

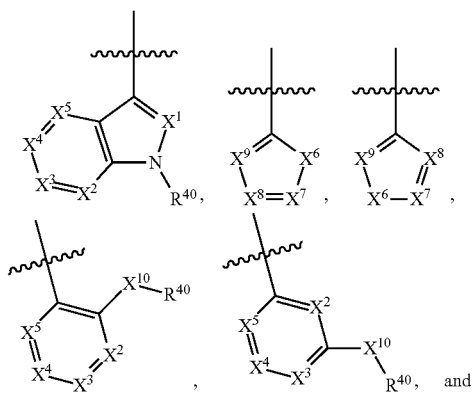

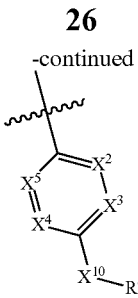

wherein $X^1$, $X^2$, $X^3$, $X^4$, $X^5$, $X^7$, $X^8$, and $X^9$ are each independently selected from the group consisting of N and $CR^{41}$;

$X^6$ and $X^{10}$ are each independently selected from the group consisting of S, O, $C(R^{42})_2$, and $NR^{43}$;

each occurrence of $R^{40}$, $R^{41}$, $R^{42}$, and $R^{43}$ is independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{44}$, $SR^{44}$, $S(=O)R^{44}$, $S(=O)_2R^{44}$, $NHS(=O)_2R^{44}$, $C(=O)R^{44}$, $OC(=O)R^{44}$, $CO_2R^{44}$, $OCO_2R^{44}$, $CH(R^{44})_2$, $N(R^{44})_2$, $C(=O)N(R^{44})_2$, $OC(=O)N(R^{44})_2$, $NHC(=O)NH(R^{44})$, $NHC(=O)R^{44}$, $NHC(=O)OR^{44}$, $C(OH)(R^{44})_2$, and $C(NH_2)(R^{44})_2$; and each occurrence of $R^{44}$ is independently selected from the group consisting of H and $C_1$-$C_6$ alkyl.

In one embodiment, $X^1$ is $CR^{41}$. In another embodiment, $X^1$ is N. In one embodiment, $X^2$ is $CR^{41}$. In another embodiment, $X^2$ is N. In one embodiment, $X^3$ is $CR^{41}$. In another embodiment, $X^3$ is N. In one embodiment, $X^4$ is $CR^{41}$. In another embodiment, $X^4$ is N. In one embodiment, $X^5$ is $CR^{41}$. In another embodiment, $X^5$ is N. In one embodiment, $X^6$ is S. In another embodiment, $X^6$ is O. In another embodiment, $X^6$ is $NR^{43}$. In one embodiment, $X^7$ is $CR^{41}$. In another embodiment, $X^7$ is N. In one embodiment, $X^8$ is $CR^{41}$. In another embodiment, $X^8$ is N. In one embodiment, $X^9$ is $CR^{41}$. In another embodiment, $X^9$ is N.

In one embodiment, Het is selected from the group consisting of:

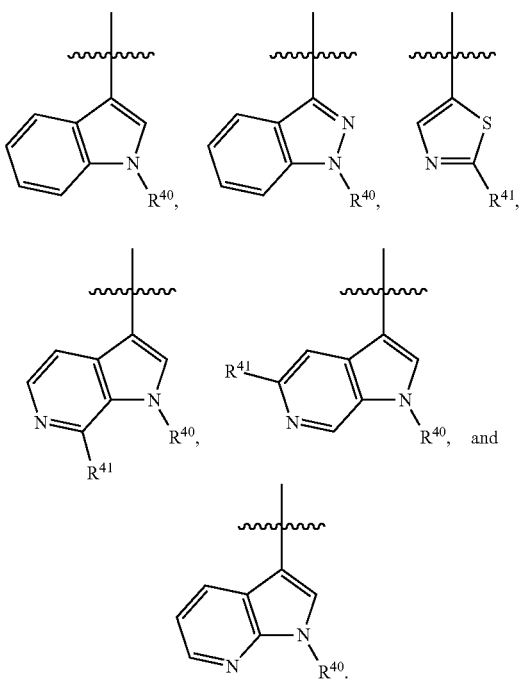

In one embodiment, Het is selected from the group consisting of:

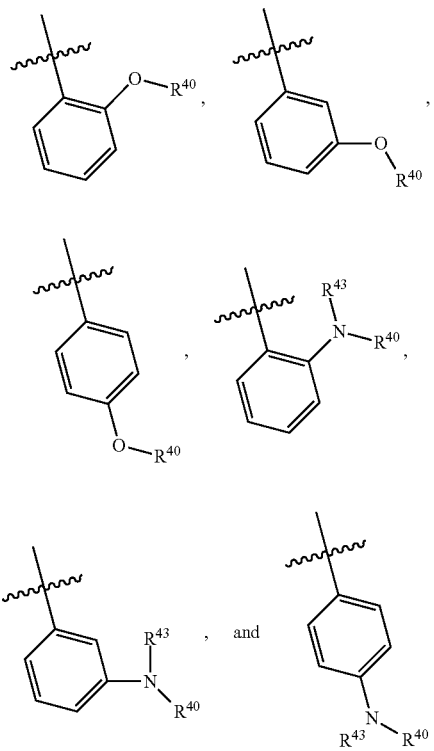

In one embodiment, $R^{40}$ is H.

In one embodiment, $R^{41}$ is H. In another embodiment, $R^{41}$ is methoxy. In one embodiment, each $R^{41}$ is H. In another embodiment, one $R^{41}$ is methoxy and the remaining $R^{41}$ are H. In another embodiment, one $R^{41}$ is —$NH_2$ and the remaining $R^{41}$ are H.

In one embodiment, the compound is selected from the group consisting of:

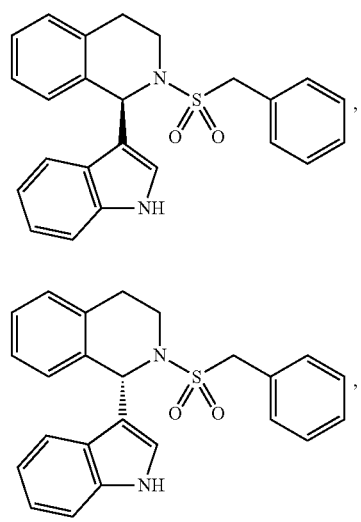

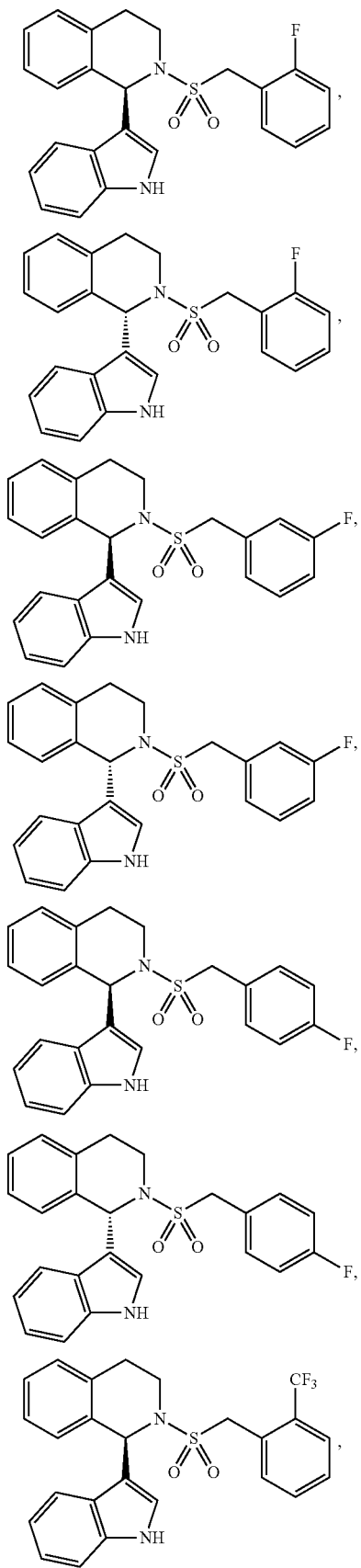

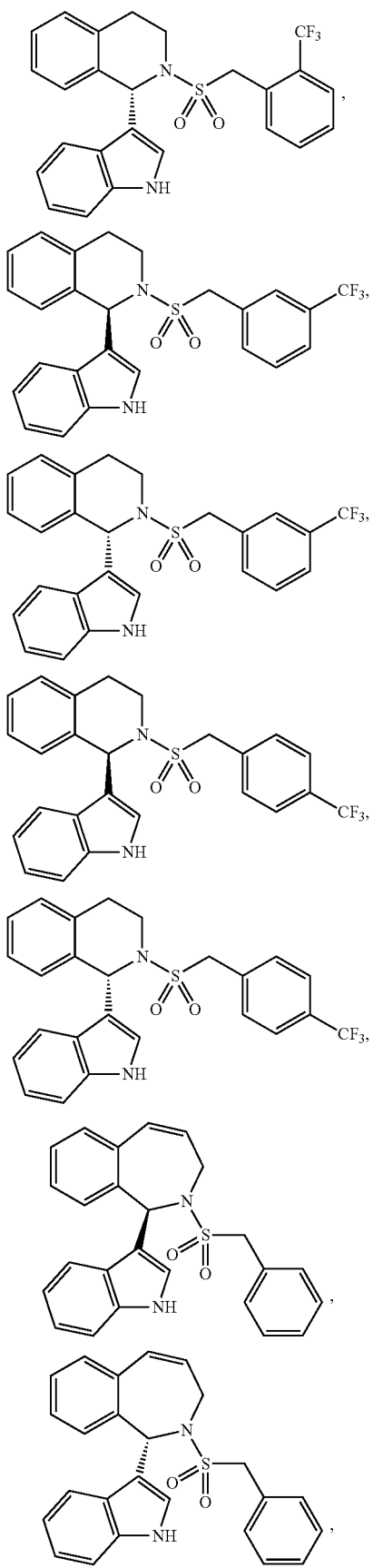
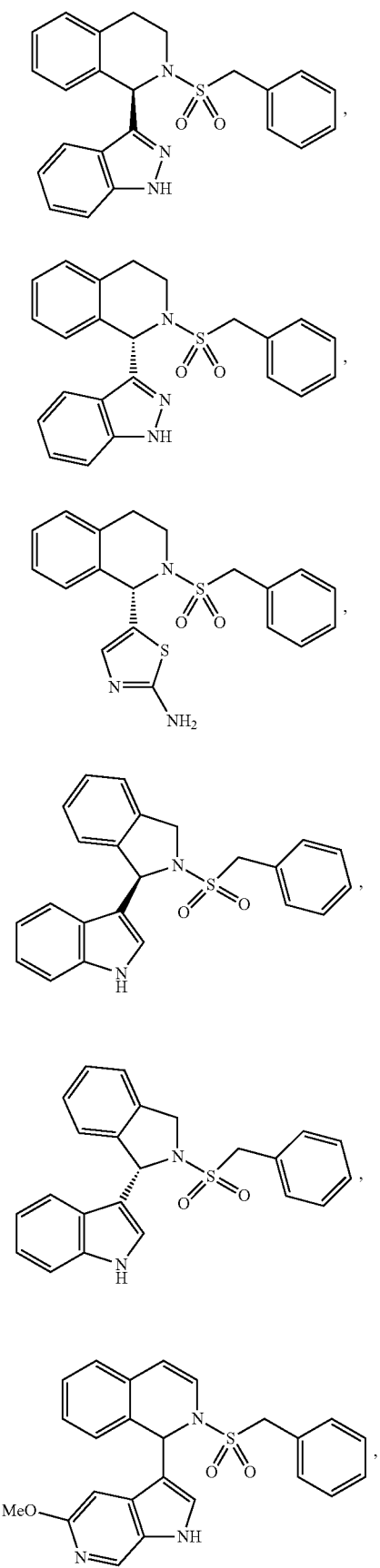

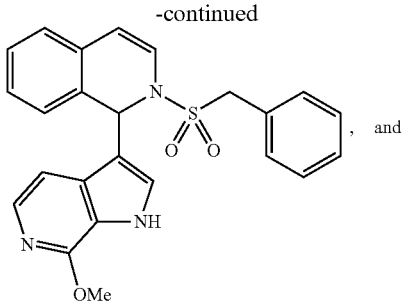

, and

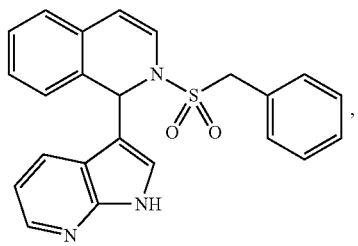

, a salt or solvate thereof, and any combinations thereof.

In one embodiment, the compound is:

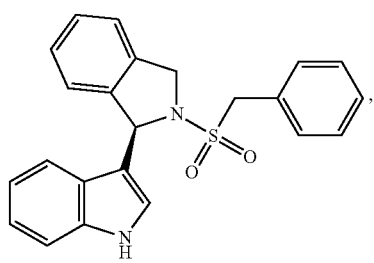 [SMILES: O=S(=O)(Cc1ccccc1)N1Cc2ccccc2[C@@H]1c1c[nH]c2ccccc12]

, a salt or solvate thereof, and any combinations thereof.

The invention also includes a composition comprising at least one compound selected from the group consisting of formula (I), formula (II), and formula (III).

The invention also includes a pharmaceutical composition comprising at least one compound selected from the group consisting of formula (I), formula (II), and formula (III).

The compounds of the invention may possess one or more stereocenters, and each stereocenter may exist independently in either the R or S configuration. The present invention is based in part on the discovery that in certain embodiments, the R enantiomer of a compound of the invention exhibited superior bioactivity than the S enantiomer.

The present invention therefore includes any possible stereoisomers, enantiomers, diastereomers, racemates, salts, or mixtures thereof of the compounds of the invention that are efficacious in the treatment of cancer. The isomers resulting from the presence of a chiral center comprise a pair of non-superimposable isomers that are called "enantiomers." Single enantiomers of a pure compound are optically active, i.e., they are capable of rotating the plane of plane polarized light. The present invention is meant to encompass diastereoisomers as well as their racemic and resolved, diastereomerically and enantiomerically pure forms and salts thereof. As used herein, the terms "enantiomerically pure form" or "enantiomerically pure" refer to a compound that has been substantially purified from the corresponding optical isomer(s) of the same formula. The compound is at least about 80% pure, at least about 90% pure, at least 98% pure, or at least about 99% pure, by weight.

In one embodiment, compounds described herein are present in optically active or racemic forms. In another embodiment, the compound of the invention is the S enantiomer. In one embodiment, the compound of the invention is the R enantiomer. It is to be understood that the compounds described herein encompass racemic, optically-active, regioisomeric and stereoisomeric forms, or combinations thereof that possess the therapeutically useful properties described herein. In one embodiment, a mixture of one or more isomer is utilized as the therapeutic compound described herein. In another embodiment, compounds described herein contain one or more chiral centers.

Preparation of the Compounds of the Invention

Compounds of formula (I)-(III) may be prepared by the general schemes described herein, using the synthetic method known by those skilled in the art. The following examples illustrate non-limiting embodiments of the invention.

In one aspect, compounds of formula (I) are synthesized by oxidative cleavage of a vinyl group followed by reduction to provide a benzylic alcohol. The alcohol can then be converted to a leaving group such as a mesylate, which can then undergo intramolecular cyclization to arrive at the desired compound. Enantiomers and/or diastereomers may subsequently be separated using any method known in the art.

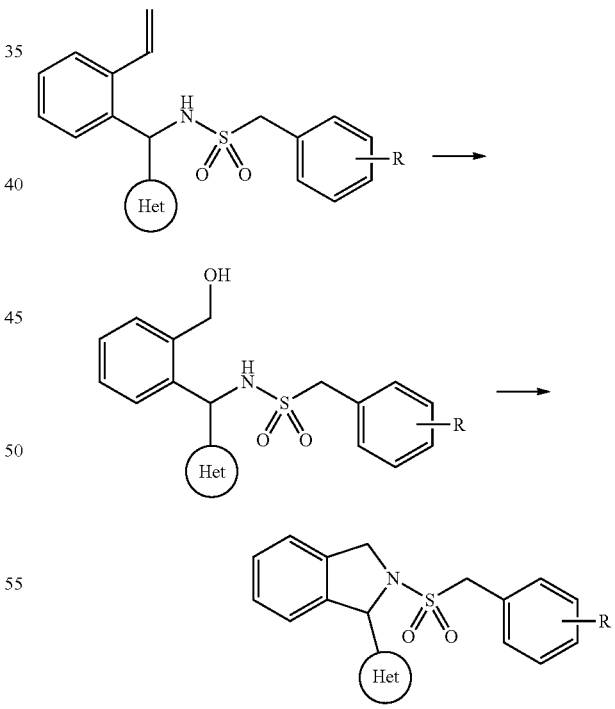

In another aspect, compounds of formula (II) are synthesized by the reaction of brominated heteroaryl group with a chiral benzylidene sulfonamide, followed by ring closure and subsequent deprotection. Enantiomers and/or diastereomers may subsequently be separated using any method known in the art.

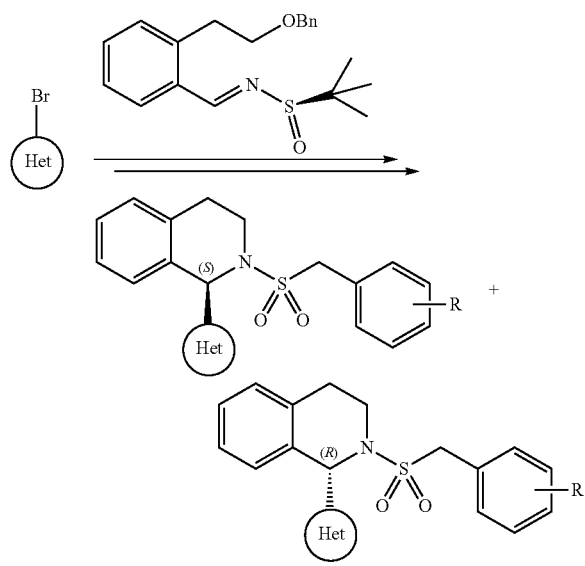

In another aspect, compounds of formula (III) are synthesized via bifunctional cinchona alkaloid-thiourea catalyzed addition of a heteroaryl group to a sulfonyl amide. Enantiomers and/or diastereomers may subsequently be separated using any method known in the art.

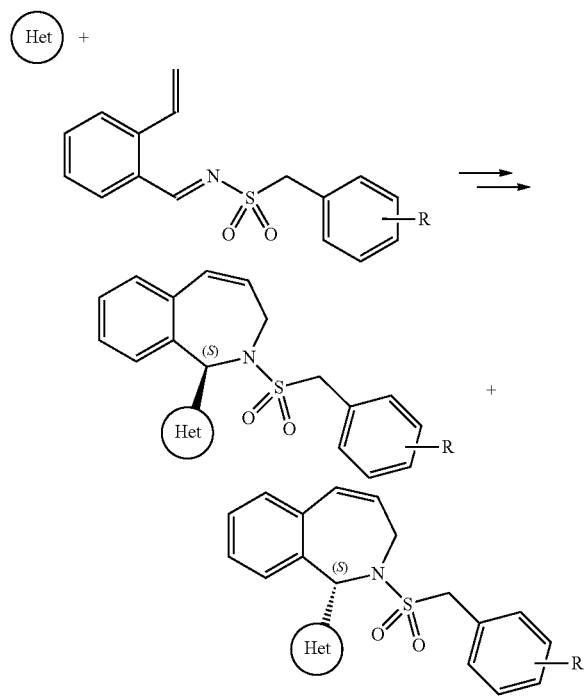

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Methods of the Invention

The invention includes a method of treating or preventing cancer in a subject in need thereof. The method comprises administering to the subject an effective amount of a therapeutic composition comprising a compound of the invention. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the compositions of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers that can be treated with the compositions of the invention include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, that can be treated with the compositions of the invention, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In one embodiment, the cancer is selected from the group consisting of breast cancer, chronic myelogenous leukemia, osteosarcoma, glioblastoma, cervical cancer, lung cancer, colon cancer, melanoma, ovarian cancer, prostate cancer, liver cancer, pancreatic cancer, CNS tumors (including brain tumors), neuroblastoma, leukemia, bone cancer, intestinal cancer, lymphoma, and combinations thereof. In one embodiment, the cancer is breast cancer. In another embodiment, the cancer is chronic myelogenous leukemia. In another embodiment, the cancer is osteosarcoma. In another embodiment, the cancer is glioblastoma. In another embodiment, the cancer is cervical cancer. In one embodiment, the method further comprises administering to the subject an additional therapeutic agent.

In one embodiment, administering the compound of the invention to the subject allows for administering a lower dose of the therapeutic agent compared to the dose of the therapeutic agent alone that is required to achieve similar results in treating or preventing cancer in the subject. For example, in one embodiment, the compound of the invention enhances the anti-cancer activity of the additional therapeutic compound, thereby allowing for a lower dose of the therapeutic compound to provide the same effect.

In one embodiment, the compound of the invention and the therapeutic agent are co-administered to the subject. In another embodiment, the compound of the invention and the therapeutic agent are coformulated and co-administered to the subject.

In one embodiment, the subject is a mammal. In another embodiment, the mammal is a human.

Combination Therapies

The compounds of the present invention are intended to be useful in combination with one or more additional compounds. In certain embodiments, these additional compounds may comprise compounds of the present invention or therapeutic agents known to treat or reduce the symptoms or effects of cancer. Such compounds include, but are not limited to, chemotherapeutics and the like.

In non-limiting examples, the compounds of the invention may be used in combination with one or more therapeutic agents (or a salt, solvate or prodrug thereof).

In certain embodiments, the compound of the invention may be administered to a subject in conjunction with (e.g. before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan. In another embodiment, the compounds of the present invention are administered in conjunction with Ospemifene, Tamoxifen, Raloxifene, or other drugs such as ICI 182,780 and RU 58668. In another embodiment, the compounds of the invention are administered in conjunction with aromatase inhibitors. Non-limiting examples of aromatase inhibitors include Exemestane, Letrozole, and Anastrozole. In another embodiment, the compounds of the invention are administered in conjunction with DNA damaging agents, such as cisplatin, or inhibitors against other DNA repair mechanisms, such as PARP inhibitors. In another embodiment, the compounds of the invention are administered in conjunction with topoisomerase inhibitors, such as etoposide or doxorubicin. In another embodiment, the compounds of the invention are administered in conjunction with tyrosine kinase inhibitors, such as imatinib and dasatinib.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either before or after the onset of cancer. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the cancer in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically acceptable excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Synthesis, Molecular Modeling, and Biological Evaluation of Novel RAD51 Inhibitors The results described herein demonstrate a panel of new RAD51 inhibitors. Among these compounds, a novel small molecule RAD51 inhibitor, IBR120, was observed to exhibit a 4.8-fold improved growth inhibition activity in triple negative human breast cancer cell line MBA-MD-468. IBR120 also inhibited the proliferation of a broad spectrum of other cancer cell types. An approximately 10-fold difference between the $IC_{50}$ values in normal and cancer cells was observed. Moreover, IBR120 was capable of disrupting RAD51 multimerization, impairing homologous recombination repair, and inducing apoptotic cell death. Therefore, these novel RAD51 inhibitors may be useful for the treatment of difficult-to-treat cancers.

The materials and methods used are described below.
Materials and Methods
Cell Lines and Antibodies Human leukemia cell line K562 and human breast cancer cell line T47D were maintained in RPMI 1640 (Invitrogen) supplemented with 10% fetal bovine serum (FBS) and 1% penicillin-streptomycin. Human breast cancer cell lines MCF7, MDA-MB-231, MDA-MB-361, MDA-MB-435, MDA-MB468, Hs578-T, human osteosarcoma cell line U2OS, human glioblastoma cell line T98G and human cervical adenocarcinoma cell line HeLa were maintained in low glucose Dulbecco Modified Eagle Medium (DMEM, Invitrogen) supplemented with 10% FBS and 1% penicillin-streptomycin. Human normal mammary epithelical cell line MCF10A was maintained in DMEM/F12 (50:50) medium (Invitrogen) supplemented with 5% horse serum, 20 ng/mL of epidermal growth factor, 0.5 mg/mL of hydrocortisone, 100 ng/mL of Cholera Toxin, 10 µg/mL of insulin, and 1% penicillin-streptomycin. To establish HeLa cells that stably expressed DR-GFP construct, cells were transfected with DR-GFP plasmid and selected with 2 µg/mL puromycin. Antibody sources were: mouse anti-RAD51 clone 14B4 and mouse anti-p84 (GeneTex), and secondary antibodies conjugated with Horseradish Peroxidase (GeneTex).
Cell Killing Assay Standard XTT assays with a four-day drug treatment procedure were performed to measure the dose dependent cytotoxicity of IBR analogs in cultured cells. In brief, cells were plated on 96-well dishes one day before the drug treatment, followed by drug treatment on day 2 and XTT assay on day 6 after drug addition by using a commercial cell proliferation kit (Roche Scientific) following the instructions. Triplicate sets were measured and compiled for final data presentation.
HR Assay Using previously described methods (Zhu et al., 2013, EMBO Mol. Med. 5:1-13; Pierce et al., 1999, Genes Dev. 13:2633-2638), HeLa cells stably expressing DR-GFP were transfected with the I-Sce expression vector pCBASce and treated with compounds or DMSO. Cells were then trypsinized and subjected to flow cytometry.
Molecular Modeling RAD51 coordinates were from PDB (Accession No: 1N0W). RAD51 residues containing atoms within 5 Å distance from the BRC4 peptide in 1N0W was designated as binding site for docking, including residues M158, Y159, I160, F167, P168, L171, S183, V185, L186, D187, N188, V189, A190, Y191, A192, R193, A194, F195, H199, Q202, L203, L204, Y205, Q206, A207, S208, A209, M210, V212, E213, Y216, L219, R247, R250, M251, L252, R254, L255, E258, F259. Structures of small molecules were generated and optimized and molecular docking was performed using ICM Pro (Molsoft), following standard procedures as described by the software manual, using default docking parameters at thoroughness=5. Docked conformations with RMSD<2 Å were considered acceptable and kept for future analysis. Dihedral angles in the lowest energy docked conformation were recorded. Statistic analysis, clustering analysis, and predictive multivariate linear model building was performed using R (Version 3.1.0) (Zhu et al., 2013, EMBO Mol. Med. 5:1-13; Pierce et al., 1999, Genes Dev. 13:2633-2638).

Multimer Formation Assay

A mixture of RAD51 (3.2 μg) and IBR120 (1:10 molar ratio) was incubated for 15 min at 37°C., supplemented with buffer (50 mM triethanolamine-HCl [pH7.5], 0.5 mM $Mg(OAc)_2$, 1 mM DTT, 2 mM ATP and 100 μg/ml BSA, total volume 20 μl) and incubated for 15 min. The mixture was loaded onto a 2.4 ml Superdex 200 PC 3.2/30 column (Pharmacia) equilibrated with the same buffer as previously described (Zhu et al., 2013, EMBO Mol. Med. 5:1-13; Pierce et al., 1999, Genes Dev. 13:2633-2638). Fractions (50 μl) were collected and 0.5 μl of each fraction was blotted onto PVDF membrane. RAD51 was detected using anti-RAD51 antibody (mAb 14B4, GeneTex)

Figure 2:
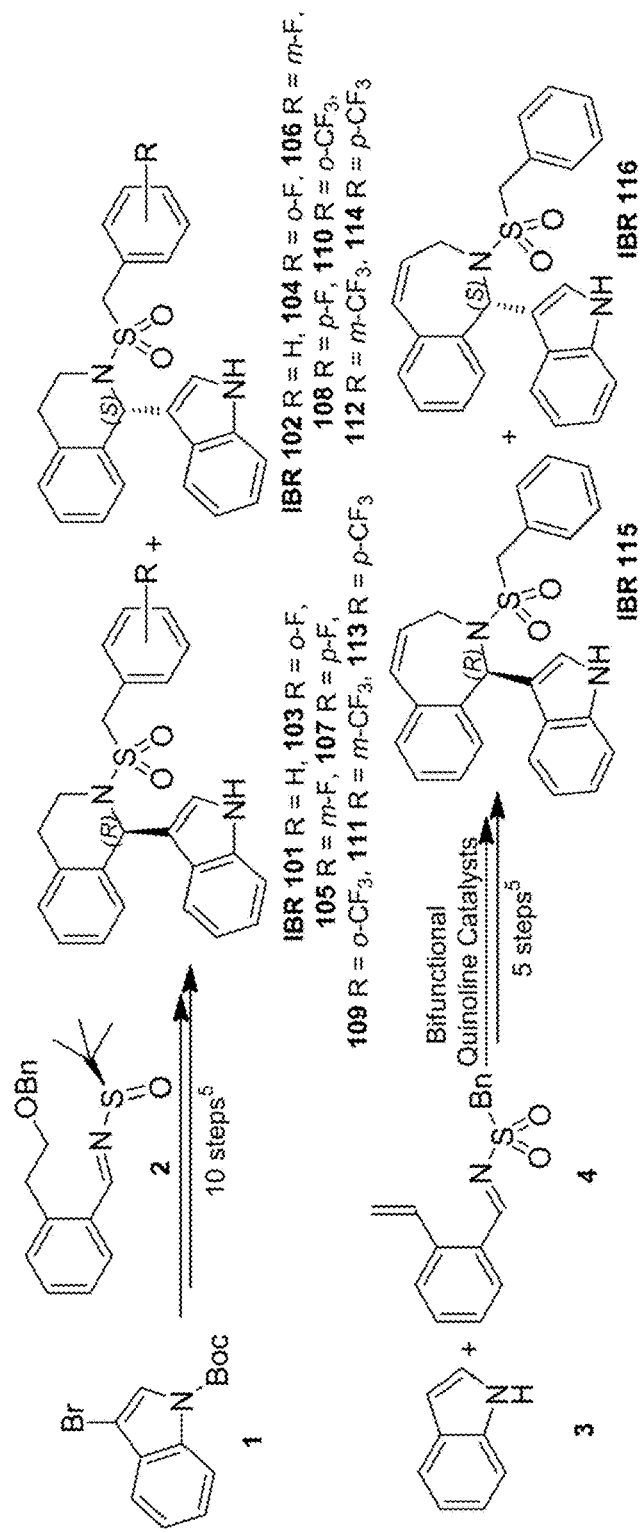
FIG. 2 is a scheme depicting an exemplary synthesis of compounds IBR101-116.

Synthesis of IBR2 analogues 1,2,3,4-tetrahydroisoquinoline analogues IBR101-114 were stereoselectively synthesized by addition of N-Boc-3-bromo-indole 1 to the chiral benzylidene sulfinamide 2 as key steps (Qiu et al., 2009, J. Org. Chem. 74:2018-2027). 2,3-Dihydro-1H-benzo[c]azepine analogues IBR115-116 were stereoselectively synthesized via bifunctional cinchona alkaloid-thiourea catalyzed addition of unprotected indole 3 to the sulfonyl amide 4 (FIG. 2) (Qiu et al., 2009, J. Org. Chem. 74:2018-2027; Wang et al., 2006, J. Am. Chem. Soc. 128:8156-8157).

Figure 3:
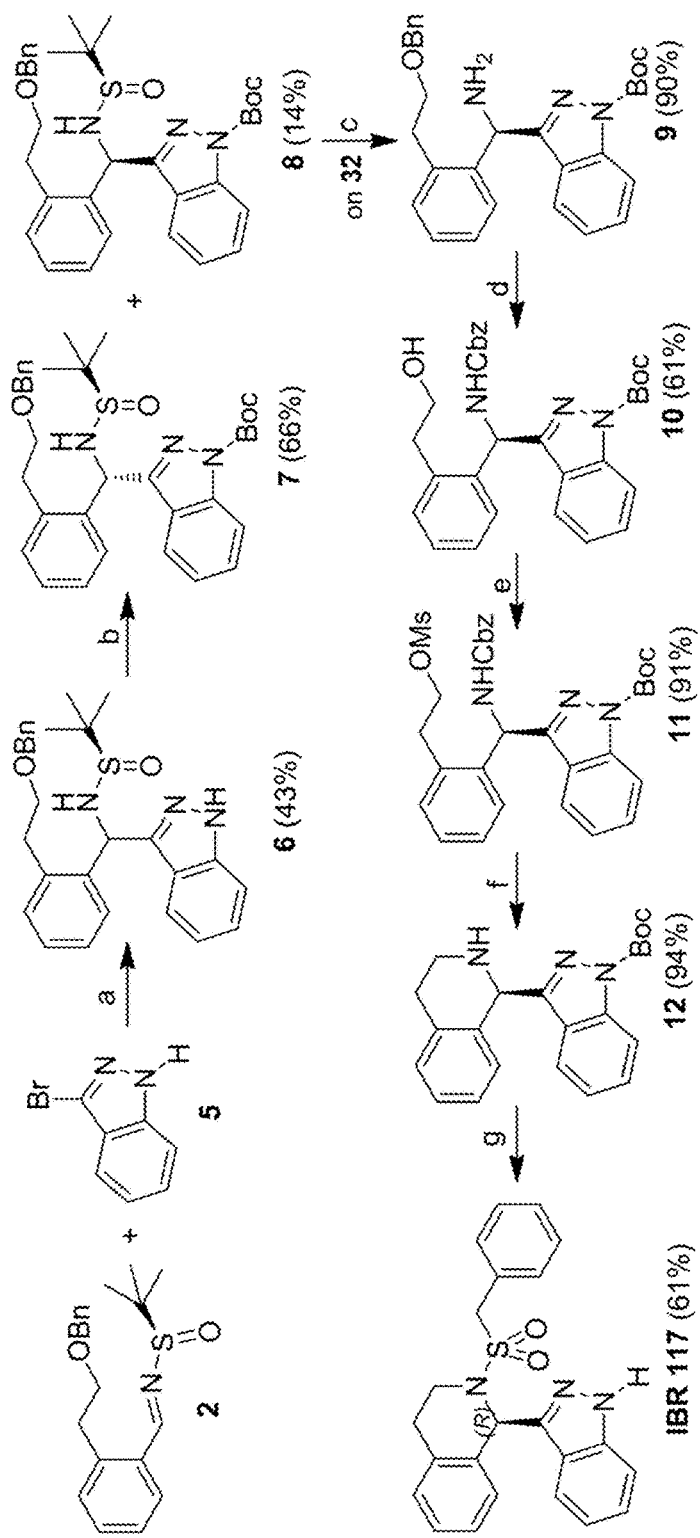
FIG. 3 is a scheme depicting an exemplary synthesis of compound IBR117.[a] Reagent and conditions: (a) (i) n-BuLi, THF, −78°C.; (ii) t-BuLi, THF, −78 °C.; (b) Boc$_2$O, CH$_2$Cl$_2$; (c) 4M HCl in dioxane, MeOH, rt.; (d) (i) Pd/C, H$_2$ (1 atm), 4M HCl in dioxane, MeOH, rt.; (ii) CbzCl, DIPEA, CH$_2$Cl$_2$, 0°C.; (e) MsCl, DIPEA, CH$_2$Cl$_2$, rt; (f) Pd/C, MeOH, H$_2$ (1 atm), rt; (g) (i) NaOMe, MeOH, rt.; (ii) BnSO$_2$Cl, CH$_2$Cl$_2$, DIPEA, 0°C.
Figure 4:
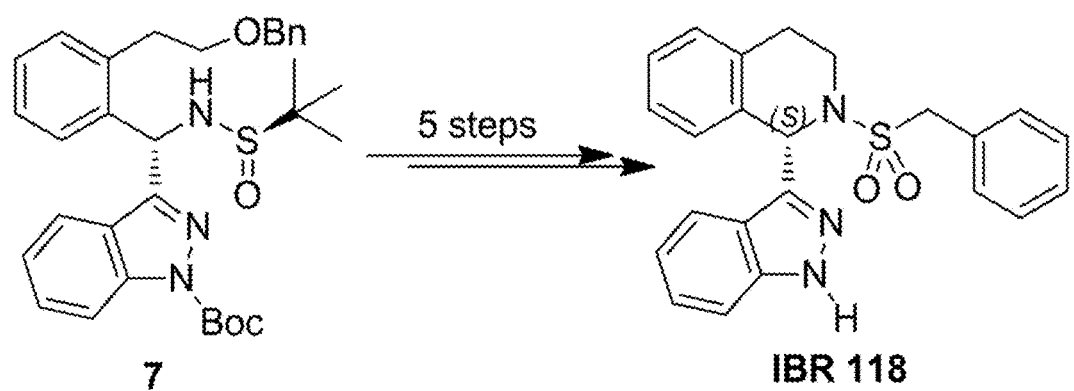
FIG. 4 is a scheme depicting an exemplary synthesis of compound IBR118.

Synthesis of optically pure indazole derivative IBR117 was accomplished via the reaction of the chiral benzylidene sulfinamide 2 (Qiu et al., 2009, J. Org. Chem. 74:2018-2027) and 3-bromoindazole 5. The desired indazolylated adduct 6 was obtained in medium yield (43%) and diastereoselectivity (65% dr) (FIG. 3) (Welch et al., 1992, Synthesis: 937-939). Protection of 6 with $Boc_2O$ gave compounds 7 and 8 in 66% and 14% yields, respectively. The diastereoisomers 7 and 8 could then be readily separated by silica gel column chromatography. Then, starting with chiral sulfinamide 8, HCl-mediated removal of the tert-butanesulfinyl group provided the amine product 9 in 90% yield. Subjecting the amine 9 to Pd/C-catalyzed hydrogenation followed by exposure of the resultant alcohol to CbzCl/DIPEA gave the compound 10 in 61% yield over 2 steps. Alcohol 10 was further mesylated to give compound 11 in 91% yield. Once hydrogenation of the mesylate 11 was carried out with Pd/C as catalyst in MeOH, the desired cyclic amine 12 was isolated in 94% yield, which led directly to IBR117 in 61% yield via deprotection with NaOMe/MeOH and subsequent benzylsulfonylation. Utilizing similar reaction procedures, the S configuration IBR2 analogue IBR118 was also prepared starting from chiral sulfinamide 7 in 37% yield over 5 steps (FIG. 4).

Figure 5:
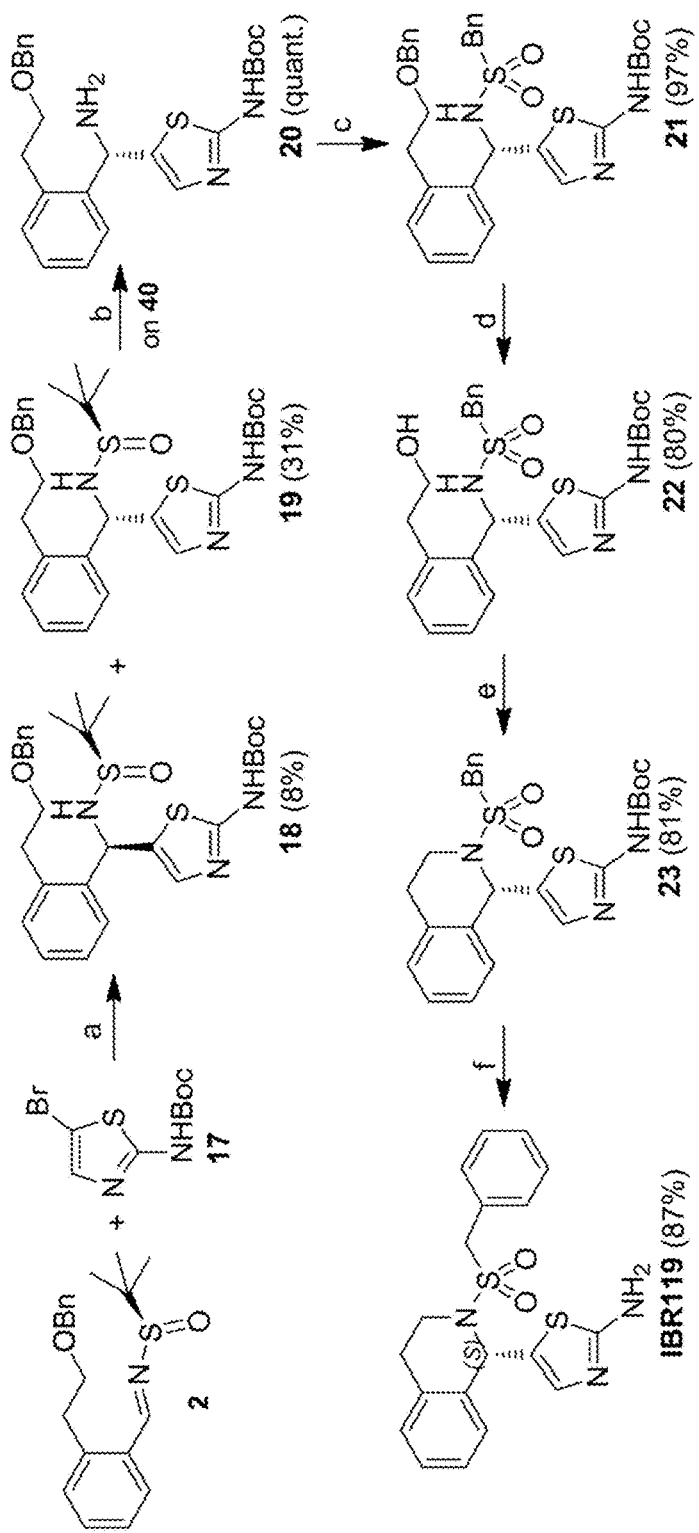
FIG. 5 is a scheme depicting an exemplary synthesis of compound IBR119.[a] Reagent and conditions: (a) n-BuLi, THF, −78°C.; (b) 4 M HCl in dioxane, MeOH, rt.; (c) BnSO$_2$Cl, CH$_2$Cl$_2$, DMAP, DIPEA; (d) Pd/C, H$_2$ (1 atm), 4 M HCl in dioxane, MeOH; (e) (i) MsCl, DMAP, DIPEA, CH$_2$Cl$_2$, 0°C. to rt.; (ii) KHMDS, THF, 0°C.; (f) TFA, CH$_2$Cl$_2$, rt.

Chiral thiazolyl amine derivative IBR119 was synthesized starting from N-Boc-2-amino-5-bromothiazole 17 and chiral benzylidene sulfinamide 2 (FIG. 5). Compound 2 was then treated with N-Boc-2-amino-5-lithiothiazole (prepared in situ via reaction of 17 with n-BuLi) at −78°C., and the desired sulfinamides 18 and 19 were provided in 39% yield with medium diastereoselectivity (59% dr). Diastereoisomers 18 and 19 were then successfully separated through silica gel chromatography. The tert-Butanesulfinyl group of 19 was removed by treatment with 4M HCl in dioxane and the amine 20 was obtained in almost quantitative yield. Benzylsulfonylation of 20 gave compound 21 in 97% yield, which was subjected to Pd/C-catalyzed hydrogenation to afford the alcohol 22 in 80% yield. Mesylation of 22 by treatment with MsCl/DMAP/DIPEA followed by exposure of resultant mesylate to KHDMS in THF furnished the desired cyclic compound 23. Synthesis of IBR119 was ultimately accomplished via TFA-mediated removal of the Boc protecting group in 23.

The synthesis of 5-membered ring derivative IBR120 started from the indole-derived compound 24, which was prepared according to previously reported methods (Qiu et al., 2009, J. Org. Chem. 74:2018-2027; Wang et al., 2006, J. Am. Chem. Soc. 128:8156-8157). A direct $OsO_4$—$NaIO_4$ mediated oxidative cleavage reaction was carried out on unprotected compound 24 in the presence of 2, 6-lutidine (Yu et al., 2004, Org. Lett. 6:3217-3219), followed by reduction with $NaBH_4$ to provide alcohol 25 (82%). Alcohol 25 was then treated with mesyl chloride and an appropriate base in DCM to give the corresponding mesylate, which was used as an intermediate for the following cyclisation reaction to form IBR120. The first attempt at cyclization of alcohol 25 using KHMDS as a base in THF gave a racemic product. Reaction conditions with milder bases were then investigated (Table 1).

TABLE 1

| Cyclization Conditions. | | | | | |
|---|---|---|---|---|---|
| Base | Solvent | Temperature | Time | Yield | ee |
| KHDMS | THF | −10° C. | 15 min | 43% | 0% |
| $Et_3N$ | DCM | r.t. | 2 h | 0% | — |
| $Et_3N$ | Dioxane | Reflux | 2 h | 0% | — |
| $K_2CO_3$ | MeOH | r.t. | 2 h | 42% | 0% |
| DIPEA | MeCN | r.t. | 2 h | 53% | 95.7% |

Figure 6:
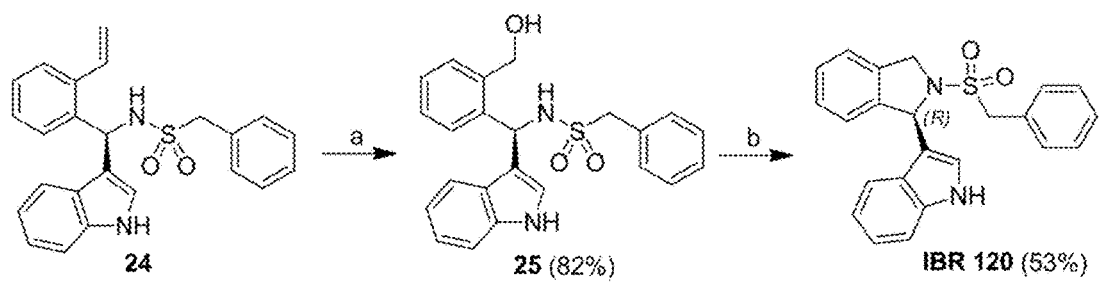
FIG. 6 is a scheme depicting an exemplary synthesis of compound IBR120.[a] Reagent and conditions: (a) (i) 2,6-lutidine, OsO$_4$, NaIO$_4$, Dioxane, H$_2$O, rt.; (ii) NaBH$_4$, THF, MeOH, 0°C. to rt.; (b) (i) MsCl, CH$_2$Cl$_2$, Et$_3$N; (ii) DIPEA, MeCN.
Figure 7:
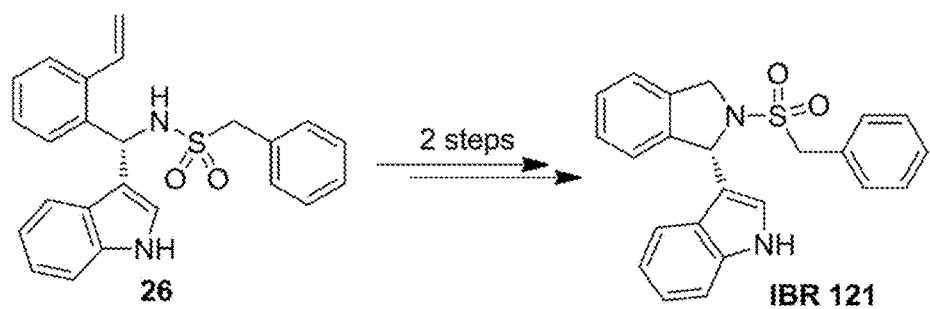
FIG. 7 is a scheme depicting an exemplary synthesis of compound IBR121.
Figure 8:
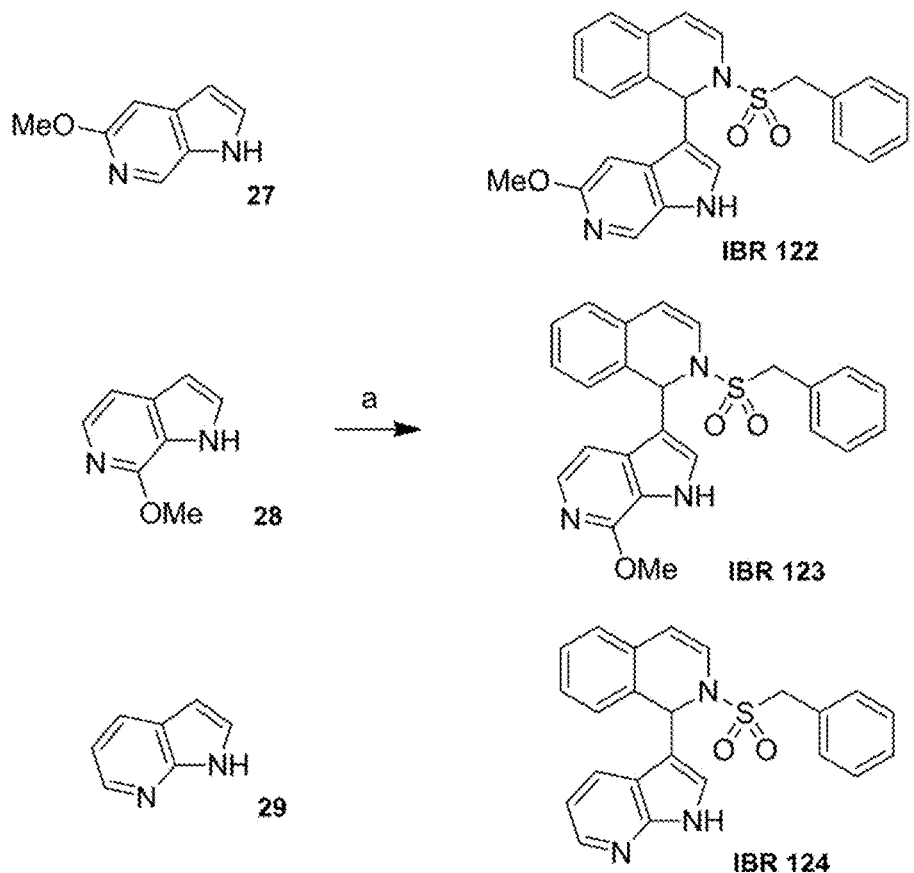
FIG. 8 is a scheme depicting an exemplary synthesis of compounds IBR122-124. The synthesis of racemic derivatives IBR122-124 was carried out using a one-pot synthetic scheme (Zhu et al., 2013, EMBO Mol. Med. 5:1-13), starting from azaindoles 27, 28, and 29, respectively.$^a$ Reagent and conditions: (a) BnSO$_2$Cl, 2 eq isoquinoline, benzene, 20 h, rt.
Figure 13:
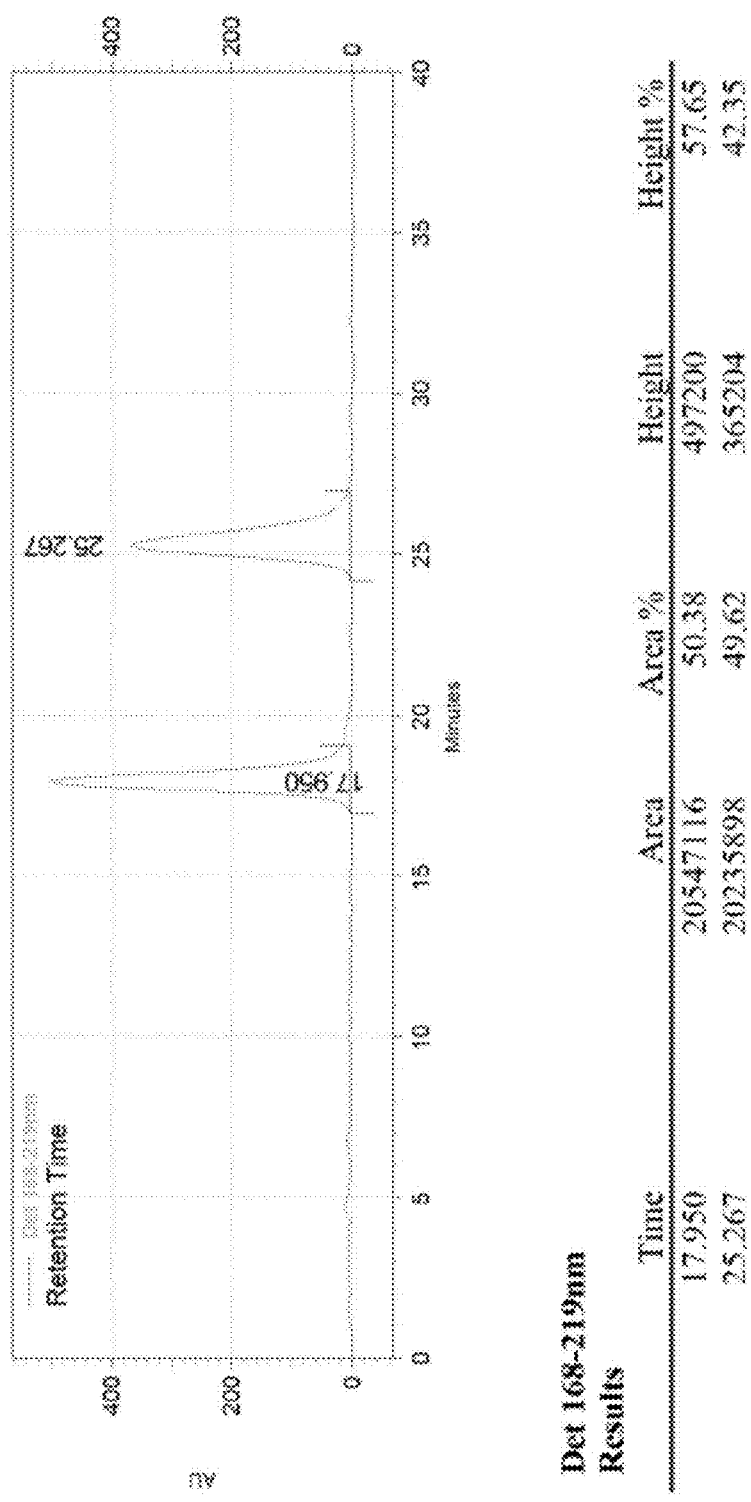
FIG. 13 is an exemplary chiral HPLC profile for racemic 3-(2-(benzylsulfonyl)isoindolin-1-yl)-1H-indole.
Figure 14:
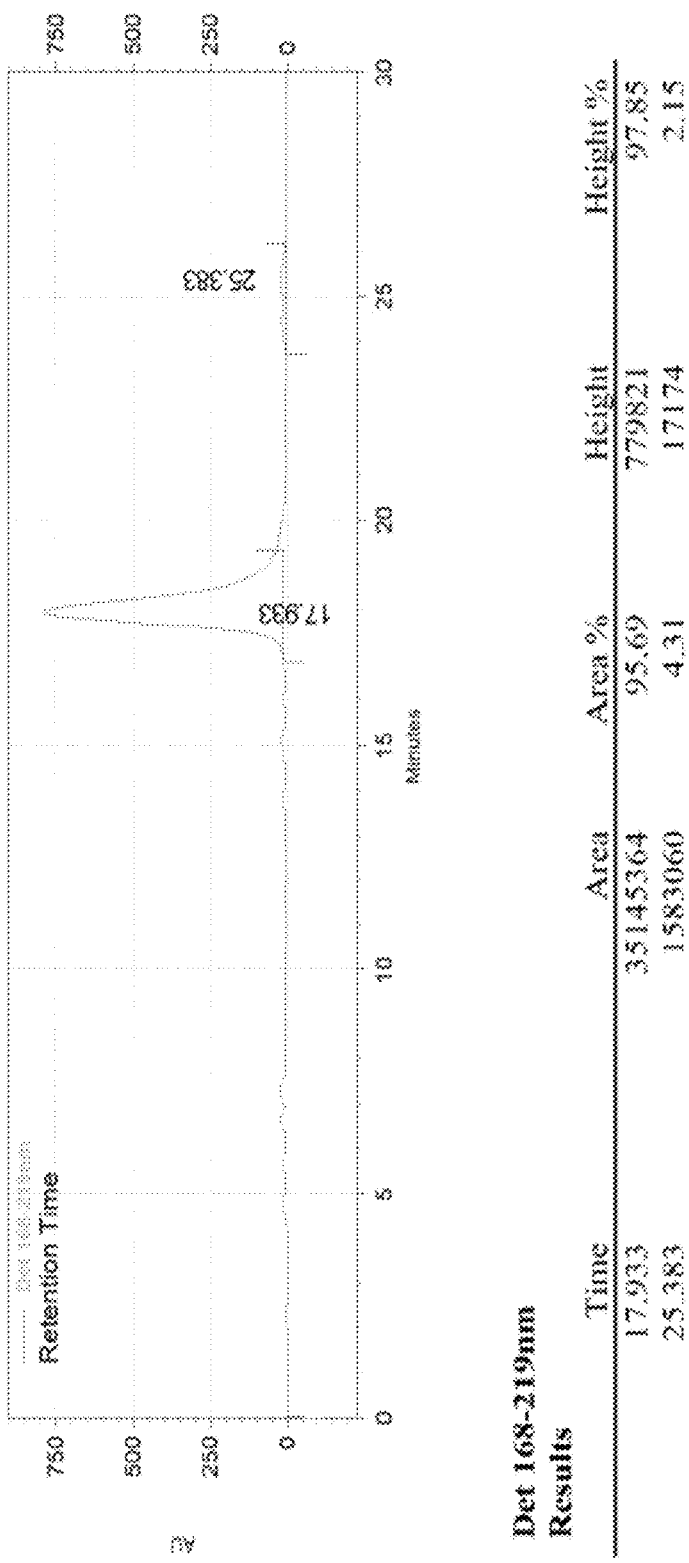
FIG. 14 is an exemplary chiral HPLC profile: (R)-3-(2-(benzylsulfonyl)isoindolin-1-yl)-1H-indole (IBR120). ee %=95.7%.
Figure 15:
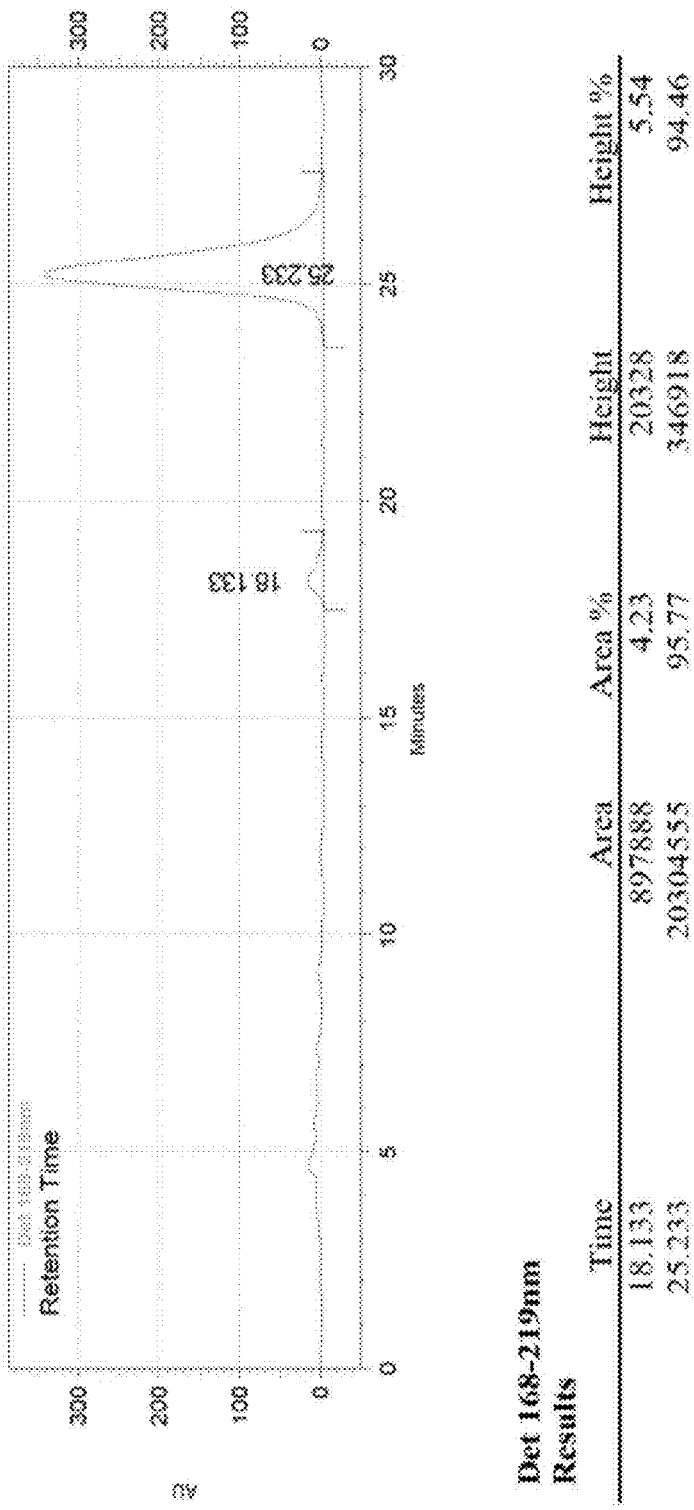
FIG. 15 is an exemplary chiral HPLC profile: (S)-3-(2-(benzylsulfonyl)isoindolin-1-yl)-1H-indole (IBR121). ee %=88.9%.

Reactions with $Et_3N$ in DCM at r.t. or in dioxane under reflux did not facilitate the conversion. The use of $K_2CO_3$ in MeOH gave racemic cyclization product in 42% yield. Finally, with Hünig's base in acetonitrile, the desired product IBR120 was obtained in 53% yield with >90% ee (FIG. 6). Utilizing the similar reaction procedures, the S configuration isomer IBR121 was also prepared starting from the indole-derived compound 26 (FIG. 7). Chiral HPLC analysis confirmed high enantiomeric purities of IBR120 and IBR121 (FIGS. 13-15). IBR122-124 were synthesized as depicted in FIG. 8.

IBR2 Analogues Inhibit Growth of Triple-Negative Human Breast Cancer

To test the possibility of inhibiting triple-negative breast cancer, the newly synthesized IBR2 analogues IBR101-124 were screened of their growth inhibition abilities using an XTT assay. As shown in Table 2, most of these synthetic IBR2 analogues inhibited the growth of triple-negative human breast cancer cell line MBA-MD-468.

TABLE 2

IBR2 analogues inhibit the growth of the triple-negative human breast cancer cell line MDA-MB-468.

| Cmpd. | IC$_{50}$ (μM) |
|---|---|
| IBR2 (rac) | 14.8 |
| IBR101 (R) | 11.7 |
| IBR102 (S) | 13.2 |
| IBR103 (R) | 12.7 |
| IBR104 (S) | 19.2 |
| IBR105 (R) | 14.2 |
| IBR106 (S) | 17.2 |
| IBR107 (R) | 11.2 |
| IBR108 (S) | 25.7 |
| IBR109 (R) | 14.8 |
| IBR110 (S) | 16.7 |
| IBR111 (R) | 11.1 |
| IBR112 (S) | 22.2 |
| IBR113 (R) | 13.6 |
| IBR114 (S) | 20.7 |
| IBR115 (R) | 14.7 |
| IBR116 (S) | >50 |
| IBR117 (R) | 9.5 |
| IBR118 (S) | 14.3 |
| IBR119 (S) | >25 |
| IBR120 (R) | 3.1 |
| IBR121 (S) | >12 |
| IBR122 (rac) | 12.7 |
| IBR123 (rac) | 6.3 |
| IBR124 (rac) | 6.2 |

It was observed that the half inhibitory concentrations (IC$_{50}$) of 1,2,3,4-tetrahydroisoquinoline analogues IBR101, 102, 103, 105, 107, 109, 111, 113, 118, 2,3-dihydro-1H-benzo[c]azepine analogue IBR115, and 1,2-dihydroisoquinoline analogue IBR122 were slightly lower than that of the parental compound IBR2; while 1,2,3,4-tetrahydroisoquinoline analogue IBR117, isoindoline analogue IBR120, and 1,2-dihydroisoquinoline analogues IBR123, 124 were significantly lower than that of IBR2. In all the successfully synthesized enantiomers, the R configuration consistently exhibited better bioactivity than the S configuration. Among all these analogues, IBR120 exhibited a 4.8-fold increase in activity (IC$_{50}$=3.1 μM), followed by IBR124, 123 and 117, with 1.6-2.4-fold increase in activities (IC$_{50}$=6.2, 6.3, 9.5 M, respectively), compared to the parental compound IBR2 (IC$_{50}$=14.8 μM).

IBR120 Inhibits a Panel of Cancer Cell Lines Growth

The growth inhibition of a panel of cancer cell lines was tested against IBR120 using an XTT assay. These cell lines included human Chronic Myelogenous Leukemia cell line K562, human breast cancer cell lines MCF7, MDA-MB-231, MDA-MB-361, MDA-MB-435, MDA-MB-468, Hs578-T, and T47D, human Osteosarcoma cell line U2OS, human Glioblastoma cell line T98G, human Cervical Cancer cell line HeLa, as well as human mammary gland normal epithelial cell line MCF10A as normal control. As shown in Table 3, while being essentially nontoxic to the normal cell line MCF10A (IC$_{50}$>30 μM), IBR120 exhibited killing effect in most tested cancer cell lines with IC$_{50}$ values in the low micromolar range (3~5 μM). This approximately 10-fold difference between the IC$_{50}$ values in normal and cancer cells demonstrates selectivity toward cancerous cells over normal cells.

TABLE 3

Inhibition activity of IBR120 on a panel of cancer cell lines.

| Cell line | Disease[19] | IC$_{50}$ (μM) |
|---|---|---|
| K562 | Chronic Myelogenous Leukemia | 3.6 ± 0.7 |
| MCF7 | Mammary Gland Adenocarcinoma | 3.1 ± 0.2 |
| MDA-MB-231 | Mammary Gland Adenocarcinoma | 3.5 ± 0.4 |
| MDA-MB-361 | Mammary Gland Adenocarcinoma | 4.5 ± 0.7 |
| MDA-MB-468 | Mammary Gland Adenocarcinoma | 3.1 ± 0.4 |
| MDA-MB-435 | Melanoma/Mammary Gland Ductal Carcinoma | 4.0 ± 0.7 |
| Hs578-T | Mammary Gland Carcinoma | 4.9 ± 1.0 |
| T47D | Mammary Gland Ductal Carcinoma | 6.3 ± 1.5 |
| U2OS | Osteosarcoma | 4.7 ± 0.5 |
| T98G | Glioblastoma Multiforme | 9.5 ± 0.9 |
| HeLa | Cervix Adenocarcinoma | 3.6 ± 0.6 |
| MCF10A | Mammary Gland, Normal epithelial cell line | >30 |

Molecular Docking Model

ICM software was employed to prepare the structures of RAD51 core domain, and to perform the molecular docking studies with IBR2 analogues. The crystal structure of human RAD51 in complex with BRC4 peptide (PDB No. 1N0W) (Pellegrini et al., 2002, Nature 420:287-293) was chosen for molecular docking studies. Initially a docking box containing all the atoms of RAD51 residues within 5 Å distance from the BRC4 peptide in 1N0W was used; and a "blind docking" procedure was performed using IBR2 as probe. Then the docking box was fixed and used for all docking studies with IBR2 analogues; the amino acid residues within the box contain RAD51 residues M158, Y159, I160, F167, P168, L171, S183, V185, L186, D187, N188, V189, A190, Y191, A192, R193, A194, F195, H199, Q202, L203, L204, Y205, Q206, A207, S208, A209, M210, V212, E213, Y216, L219, R247, R250, M251, L252, R254, L255, E258, F259. Molecular docking was then performed following rigid docking protocols; docking scores were collected and conformational analysis was performed based on the results.

Figure 9:
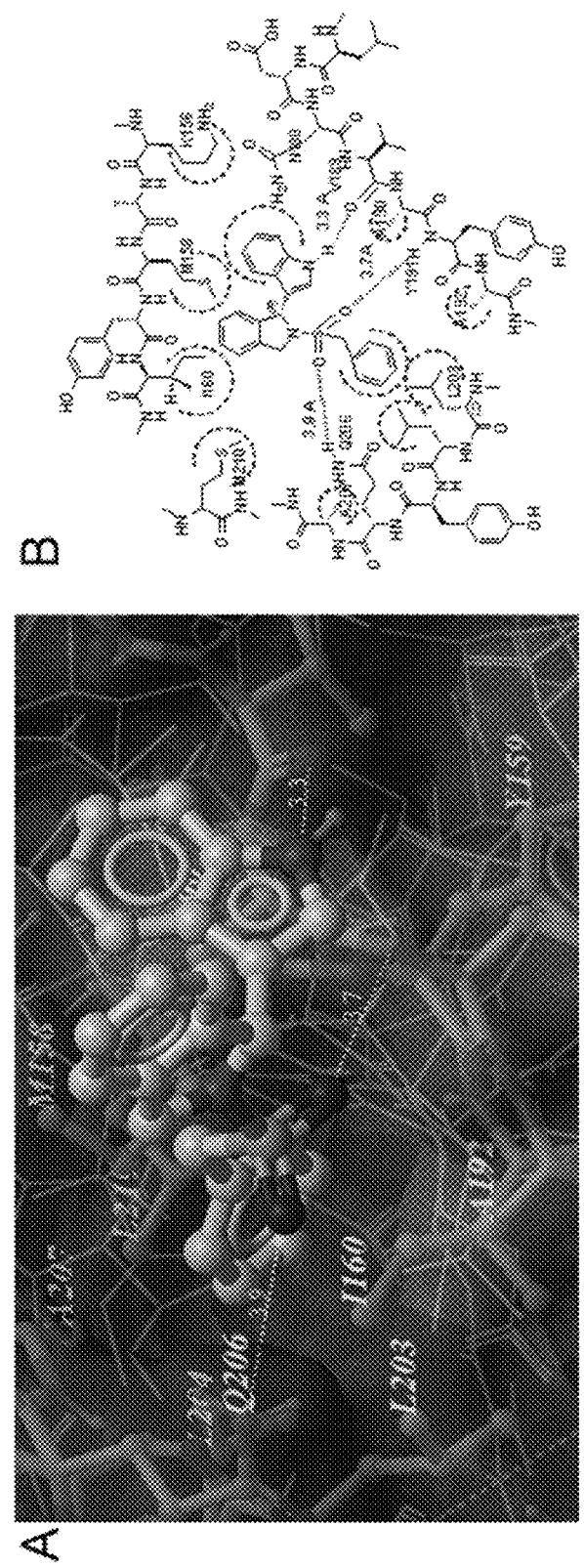
FIG. 9, comprising

Many of the residues in the binding site are hydrophobic and therefore provide hydrophobic binding surface for interacting with the aromatic ring systems of IBR compounds. Three potential hydrogen bonding sites were identified between IBR120 and RAD51 residues V189, Y191, and Q206. The distance between the indole nitrogen atom and the backbone carbonyl oxygen of V189 was 3.3 Å. Although not wishing to be bound by any particular theory, this result suggests that a hydrogen bond of moderate strength may be involved in the binding. Moreover, both of the sulfonyl oxygen atoms seem to be involved in hydrogen bonding (FIG. 9).

Structure Activity Relationship of IBR2 Analogues

The structural diversity IBR compounds with respect to IBR2 was examined as follows: (1) different bioisosteres for replacing the indolyl ring, (2) chiral center of IBR2 analogues, and (3) variable sizes of the central ring.

Figure 10:
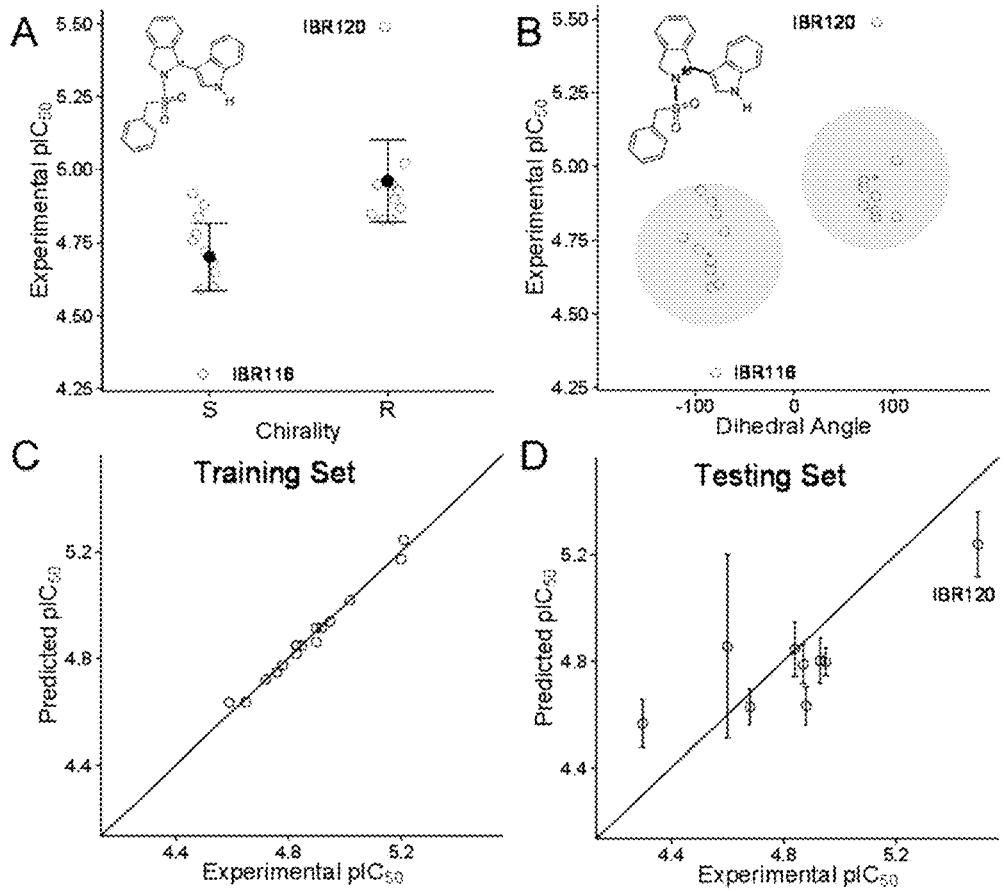
FIG. 10, comprising

By modifying indole moiety to various bioisosteres, a potential favorable modification site was identified. When compared with IBR2, IBR123 and 124 showed more than 2-fold increase of activity; and both IBR123 and 124 have included a potential hydrogen bond acceptor at the 7-position of the indolyl ring, suggesting further improvement could be made utilizing this property. Second, the growth inhibition assay results indicated that, compared with S isomers (average pIC$_{50}$=4.70), the R isomers (average pIC$_{50}$=4.96) are generally more active (Student's t-test, p=0.0047) (FIG. 10A). Moreover, increasing the central ring size from six to seven resulted in minimal change of activity of the R isomer (IBR115), but almost complete loss of function in the S isomer (IBR116). Decreasing the central ring size from six to five resulted in more than 4-fold increase of activity (IBR120). As discussed above, the docked conformation of IBR120 showed several favorable features of binding.

R-squared: 0.9599, p-value: 0.0001, FIG. 10C, Training Set). Using this model, the growth inhibition activity of most compounds in the test tests was predicted within 95% confidence interval (FIG. 10D, Testing Set).

Table 4 identifies the raw dataset used for SAR analysis and predictive multivariate linear models.

| Compound name | pIC50 | Mol Weight | Mol LogP | Mol LogS | Mol PSA | Mol Vol | Mol dHf | ICM Score | Dihedral Angle | Chirality | Training/ Test Set |
|---|---|---|---|---|---|---|---|---|---|---|---|
| IBR2 | 4.83 | 401 | 5.00 | −6.25 | 40.6 | 384 | 44.9 | −14.6 | 82.4 | racemic | Train |
| IBR101 | 4.93 | 403 | 4.52 | −6.28 | 41.5 | 380 | 33.6 | −9.49 | 70.4 | R | Test |
| IBR102 | 4.88 | 403 | 4.52 | −6.28 | 41.5 | 380 | 33.6 | −8.98 | −83.3 | S | Test |
| IBR103 | 4.90 | 404 | 3.85 | −5.54 | 54.8 | 374 | 51.6 | −13.3 | 83.1 | R | Train |
| IBR104 | 4.72 | 404 | 3.85 | −5.54 | 54.8 | 374 | 51.6 | −14.0 | −96.2 | S | Train |
| IBR105 | 4.85 | 421 | 4.67 | −6.72 | 41.5 | 385 | −11.3 | −8.45 | 83.1 | R | Train |
| IBR106 | 4.76 | 421 | 4.67 | −6.72 | 41.5 | 385 | −11.3 | −14.4 | −112 | S | Train |
| IBR107 | 4.95 | 421 | 4.79 | −6.58 | 41.5 | 386 | −11.3 | −10.1 | 70.5 | R | Test |
| IBR108 | 4.59 | 421 | 4.79 | −6.58 | 41.5 | 386 | −11.3 | −9.81 | −83.3 | S | Train |
| IBR109 | 4.83 | 421 | 4.79 | −6.79 | 41.5 | 386 | −11.3 | −8.08 | 83.3 | R | Train |
| IBR110 | 4.78 | 421 | 4.79 | −6.79 | 41.5 | 386 | −11.3 | −12.8 | −70.4 | S | Train |
| IBR111 | 4.95 | 471 | 5.76 | −7.43 | 41.5 | 417 | −12.0 | −15.6 | 70.5 | R | Train |
| IBR112 | 4.65 | 471 | 5.76 | −7.43 | 41.5 | 417 | −12.0 | −9.71 | −84.2 | S | Train |
| IBR113 | 4.87 | 471 | 5.76 | −7.31 | 41.5 | 417 | −12.0 | −10.4 | 70.3 | R | Test |
| IBR114 | 4.68 | 471 | 5.76 | −7.31 | 41.5 | 417 | −12.0 | −10.4 | −84.2 | S | Test |
| IBR115 | 4.83 | 471 | 5.64 | −7.04 | 41.5 | 417 | −12.0 | −9.95 | 104 | R | Train |
| IBR116 | 4.30 | 471 | 5.64 | −7.04 | 41.5 | 417 | −12.0 | −7.36 | −79.2 | S | Test |
| IBR117 | 5.02 | 415 | 4.64 | −6.30 | 41.8 | 406 | 41.7 | −9.87 | 104 | R | Train |
| IBR118 | 4.84 | 415 | 4.64 | −6.30 | 41.8 | 406 | 41.7 | −11.7 | −78.7 | S | Test |
| IBR119 | 4.60 | 386 | 3.20 | −4.71 | 62.9 | 336 | 12.3 | −14.5 | −75.8 | S | Test |
| IBR120 | 5.49 | 389 | 3.95 | −6.32 | 41.8 | 364 | 36.7 | −17.0 | 84.0 | R | Test |
| IBR121 | 4.92 | 389 | 3.95 | −6.32 | 41.8 | 364 | 36.7 | −12.3 | −94.5 | S | Train |
| IBR122 | 4.90 | 402 | 4.21 | −5.25 | 50.9 | 381 | 57.4 | −12.0 | 87.4 | racemic | Train |
| IBR123 | 5.20 | 432 | 4.31 | −6.19 | 57.1 | 410 | 14.4 | −10.3 | 71.8 | racemic | Train |
| IBR124 | 5.21 | 432 | 4.19 | −5.93 | 58.7 | 409 | 14.4 | −12.2 | 87.0 | racemic | Train |

To better understand how these structural factors might have invoked such changes in activity, improved docked conformations of all compounds were examined. It was hypothesized that the varying the sizes of the ring and the substituents could result in differences in the desired orientations of the indolyl, phenyl, and sulphonyl groups. This orientation can be readily quantified with a dihedral angle in the docking model (C—C—N—S(FIG. 10B, inset)). A cluster analysis (k-means, k=2) of this dihedral angle with regard to the $IC_{50}$'s suggested that the dihedral angles clustered around 75~100 degrees usually correlated with better activity; while the dihedral angles of −60~−110 degrees correlated with poorer activity (FIG. 10B). Although not wishing to be bound by any particular theory, these results suggest that the combined conformational effect elicited by the ring size and substituents determines the activity of a certain compound, at least in part.

Figure 16:
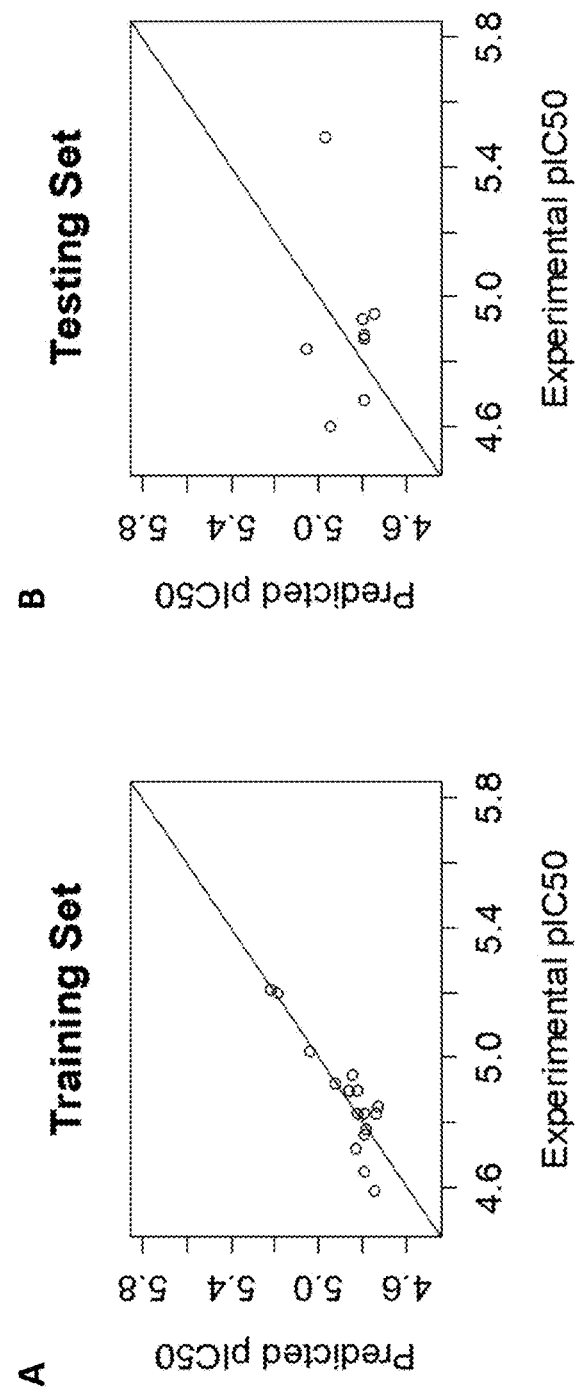
FIG. 16, comprising
Figure 17:
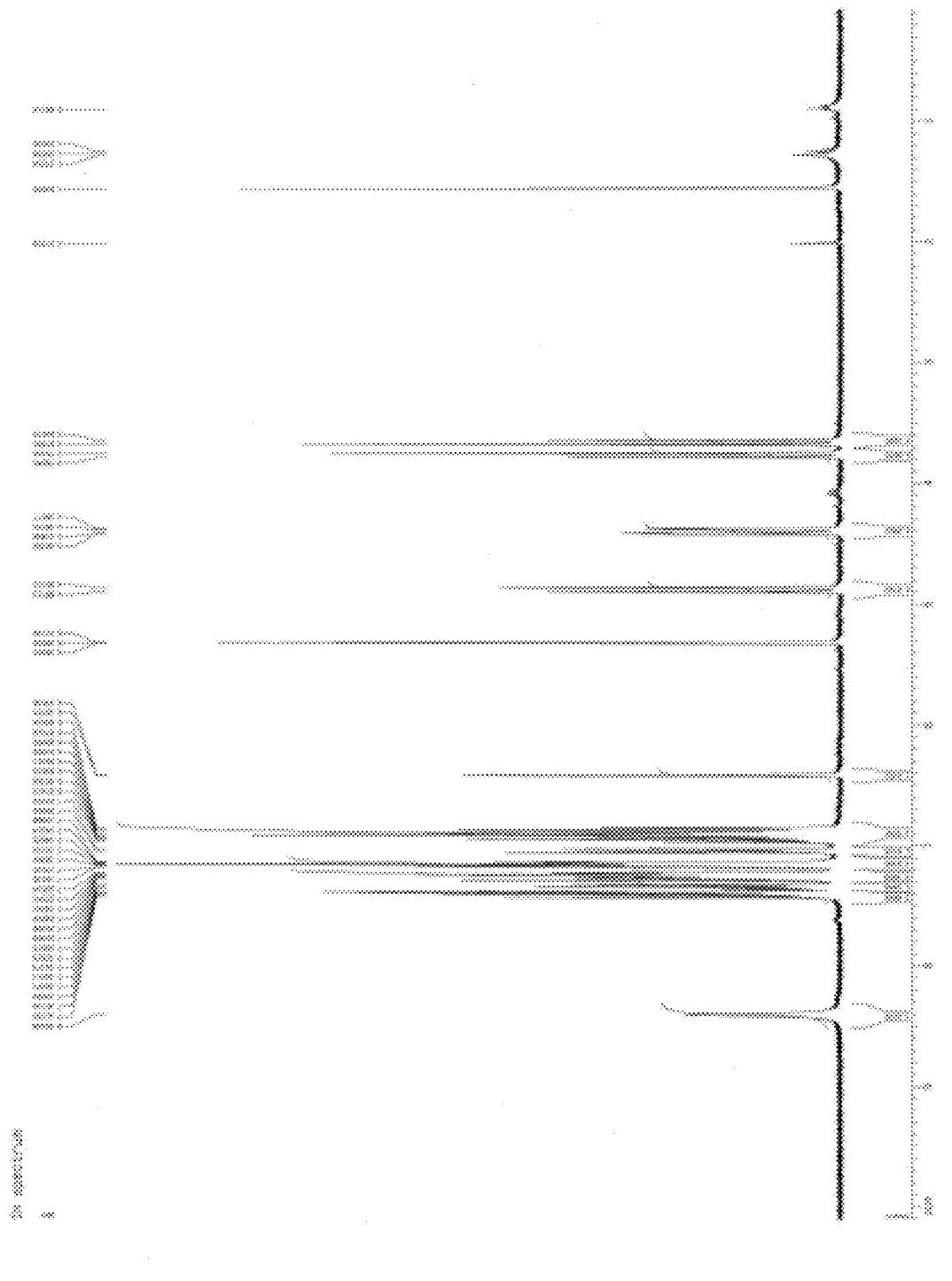
FIG. 17 is an exemplary $^1$H NMR spectrum of IBR120.
Figure 18:
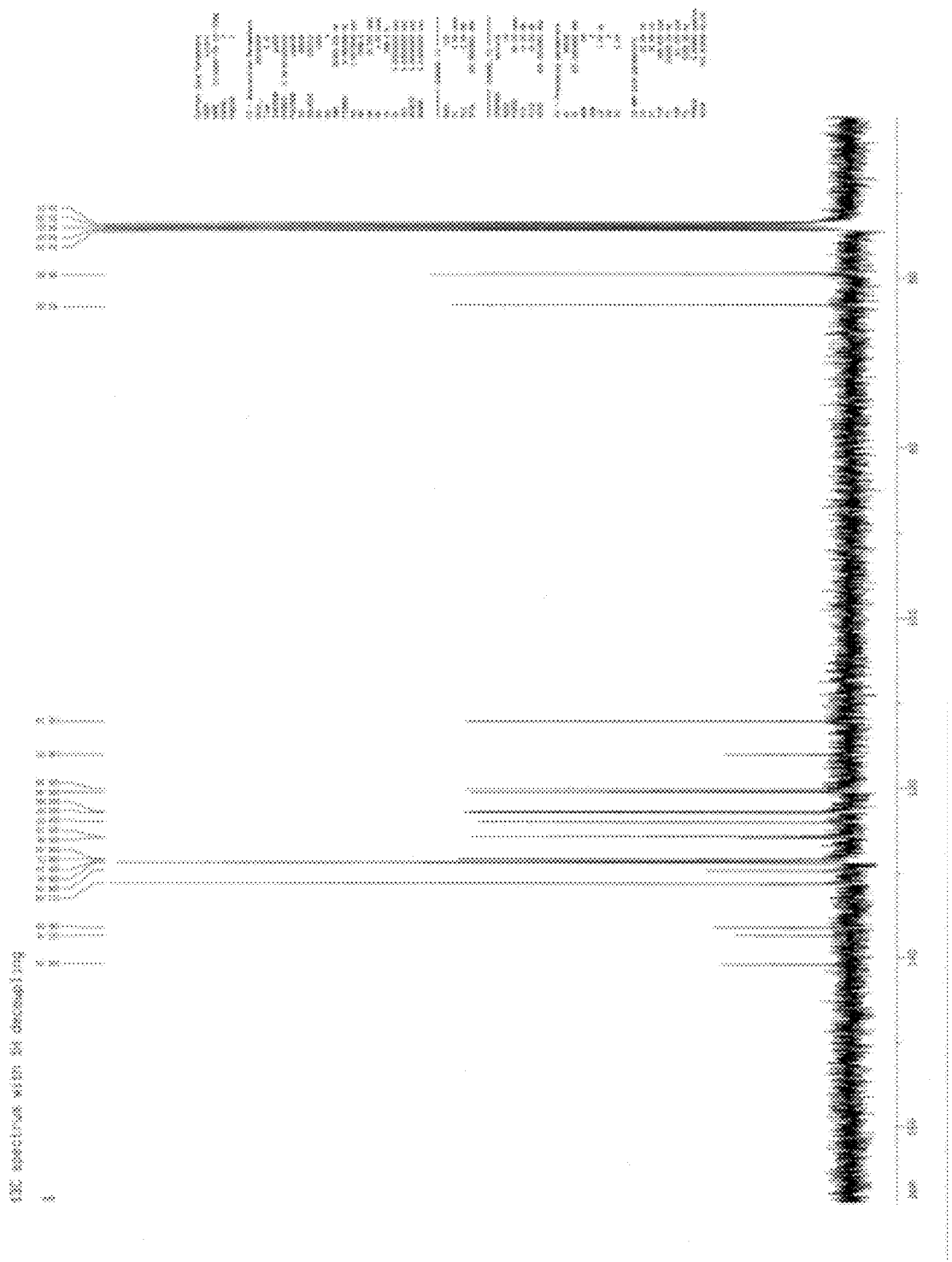
FIG. 18 is an exemplary $^{13}$C NMR spectrum of IBR120.
Figure 19:
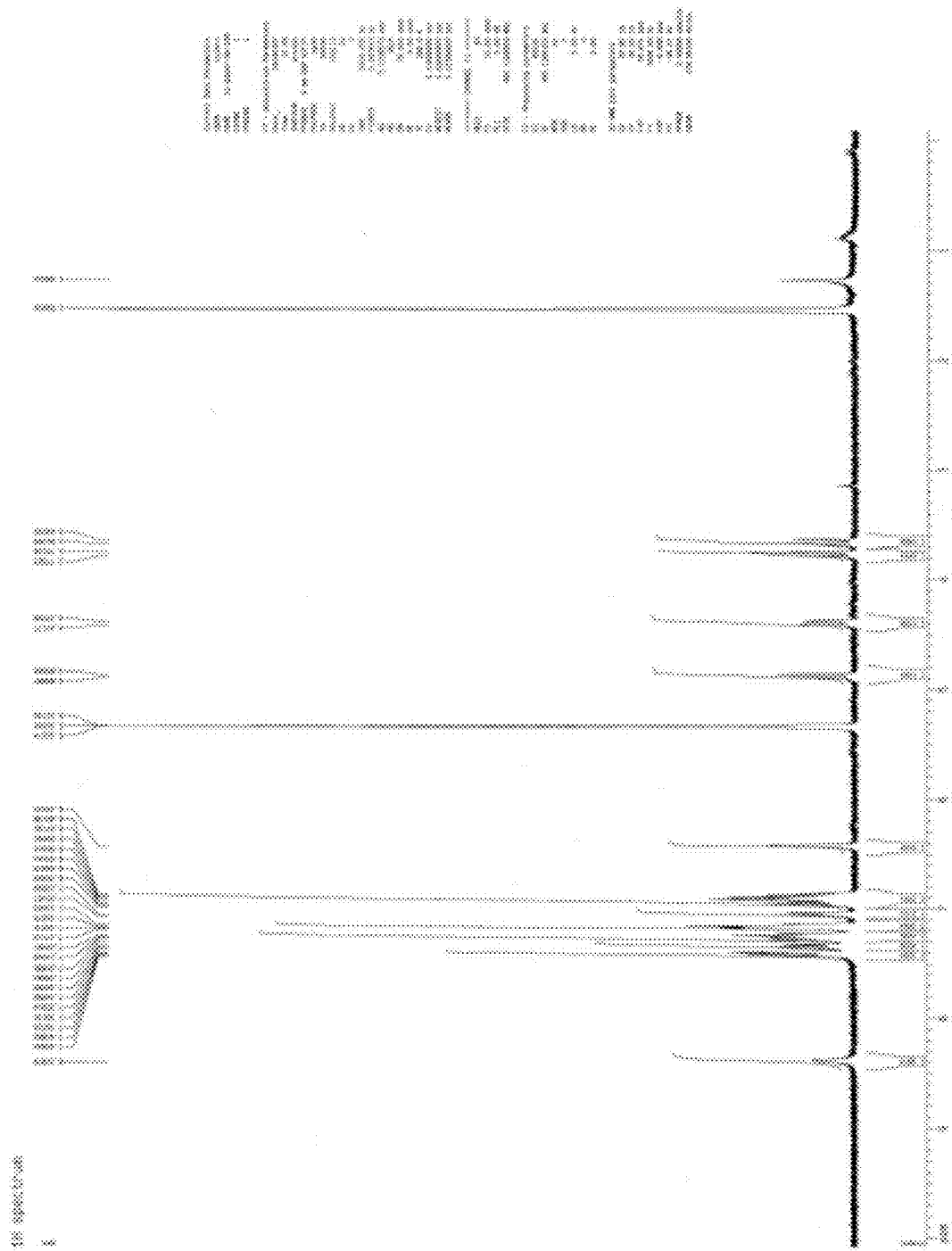
FIG. 19 is an exemplary $^1$H NMR spectrum of IBR121.
Figure 20:
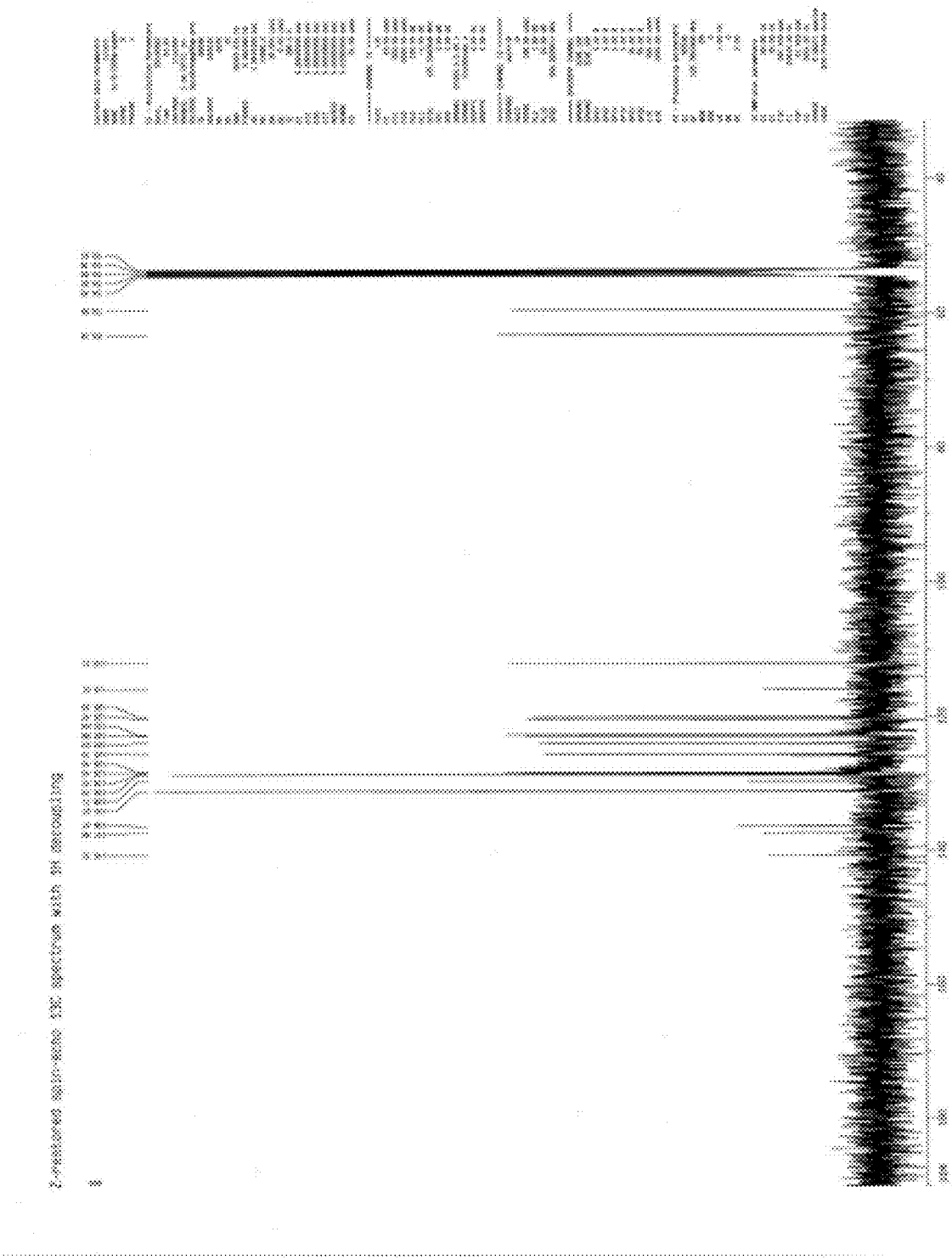
FIG. 20 is an exemplary $^{13}$C NMR spectrum of IBR121.

A predicative multivariate linear regression model of this class of molecules was designed based on the above observations. First, the molecules were randomly divided into a test set (9 compounds) and a training set (16 compounds). A handful of molecular descriptors (Molecular Weight, Log P, Log S, Polar Surface Area, Molecular Volume, Heat of Formation) were then selected to account for the difference in physicochemical properties of the small molecules, and docking scores as indicators of overall binding capacity with RAD51. A first predicative model was generated (Multiple R-squared: 0.7719, Adjusted R-squared: 0.5723, p-value: 0.03853; FIG. 16). Next, based on the above exploratory analysis, two extra parameters (dihedral angle and chirality) were included to account for the important conformational preference as discussed above, and an improved predicative model was obtained (Multiple R-squared: 0.984, Adjusted IBR120 Inhibits RAD51 Multimerization.

Figure 11:
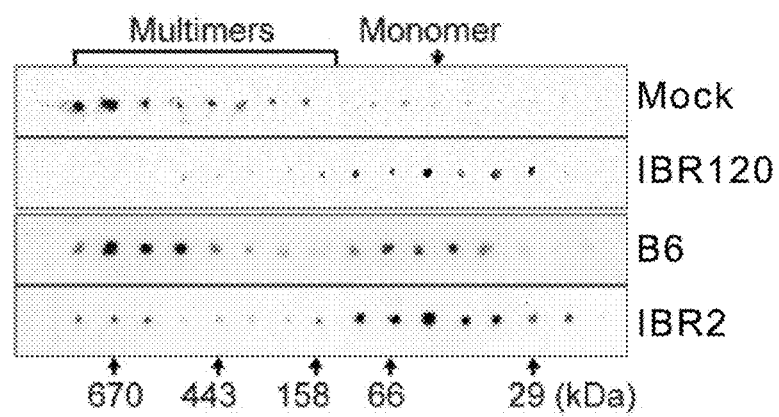
FIG. 11 depicts experimental data demonstrating that IBR120 inhibits RAD51 multimerization.

On the RAD51 core domain, a hydrophobic pocket formed between β-strand B3 and α-helix A4 of RAD51 is critical for RAD51 multimerization (Pellegrini et al., 2002, Nature 420:287-293). It was hypothesized that IBR compounds should be able to inhibit RAD51 multimerization. In order to test this hypothesis, the gel filtration profile of RAD51 multimerization in the presence of IBR120 or vehicle (DMSO) alone were compared. In the presence of IBR120, the RAD51 elution profile exhibited a major peak consistent with the molecular weight of a monomer, while in the absence of IBR120, the majority of RAD51 formed multimers (FIG. 11), indicating that IBR120, can inhibit RAD51 multimerization.

IBR120 Inhibits Homologous Recombination (HR) Repair

Figure 12:
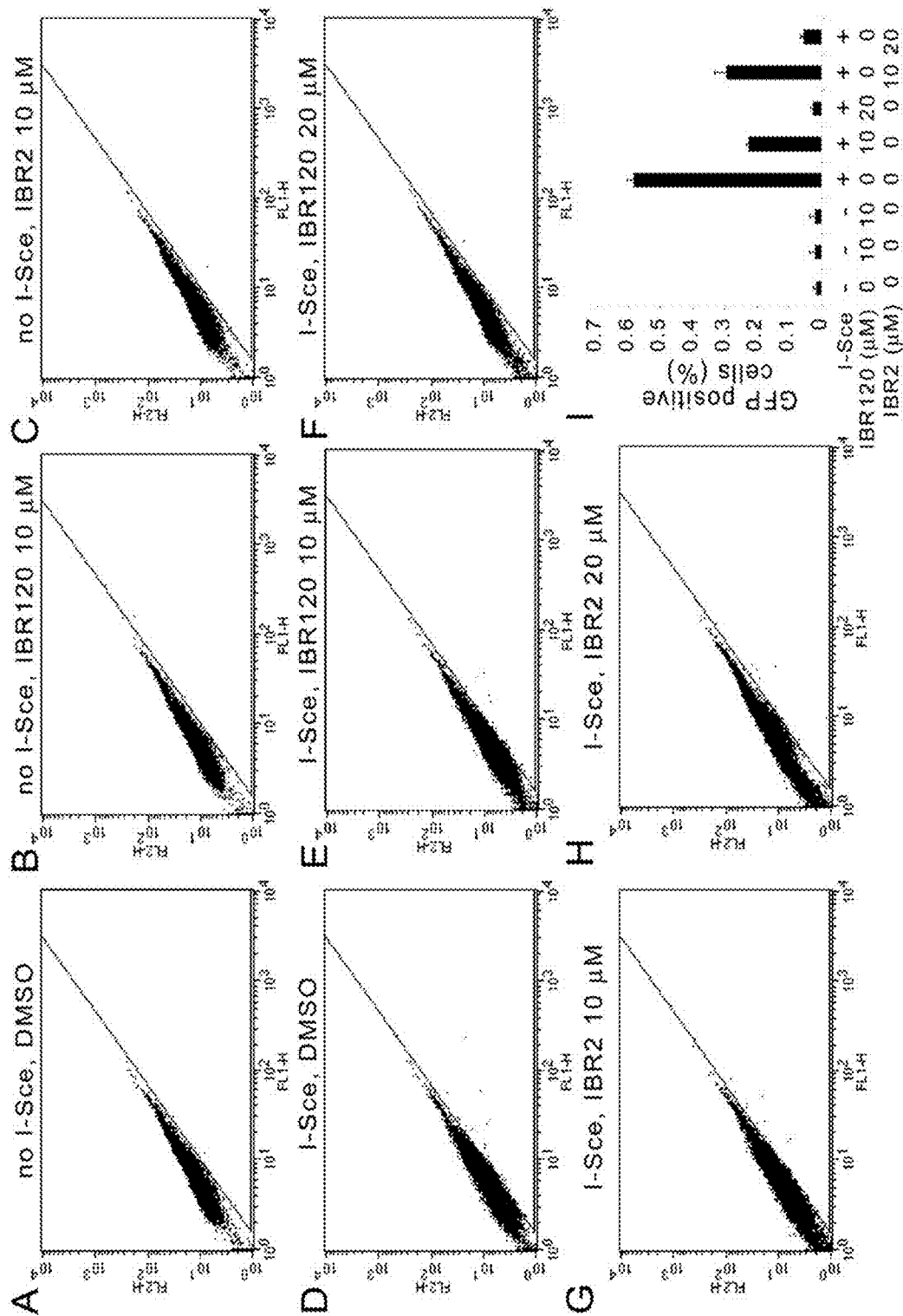
FIG. 12, comprising

Inhibition of RAD51 function will lead to failure in HR repair. To test this possibility, an I-SceI inducible gene conversion assay that measures the DNA double strand break repair frequency by detecting successful restoration of a fluorescent GFP from the repair substrate DR-GFP was used following previously published methods (Zhu et al., 2013, EMBO Mol. Med. 5:1-13; Pierce et al., 1999, Genes Dev. 13:2633-2638). DR-GFP, consisting of two nonfluorescent GFP derivatives, SceGFP and iGFP, was first stably integrated into HeLa cells. Upon I-SceI expression by transient transfection for 24 hours to induce DSBs, cells were treated with DMSO, 10 or 20 µM of IBR120 or IBR2 for another 24 hours and the GFP positive population resulting from successful recombination was measured by flow cytometry. As shown in FIG. 12, the HR frequency was significantly reduced after IBR120 treatment in a dose dependent manner. Compared with IBR2 treatment, IBR120 treatment consistently led to greater depression of HR repair activity.

As demonstrated herein, several stereoselective synthetic routes to synthesize chiral IBR2 analogues were developed. One route featured the addition of N-Boc-3-bromo-indole 1, 3-bromoindazole 5 and N-Boc-2-amino-5-bromothiazole 17 to the benzylidene sulfinamide 2, which provided the separable diasteroisomers in medium to good yields. The results of the biological assays demonstrated that compounds with the R configuration exhibited superior bioactivity over compounds with the S configuration, and the 5-membered central ring system proves to be the most active. Although not wishing to be bound by any particular theory, the results suggest that these effects can be structurally correlated to the fine-tuning of the orientation of the two aromatic groups. As a result, these modifications led to a more than 4-fold increase of growth inhibition activity in a panel of cancer cells to provide improved RAD51 inhibitors.

The synthetic scheme for most of the described IBR compounds relies on the stereoselective arylation of chiral benzylidene sulfinamide 2, using an in situ generated lithium reagent, followed by separation of diastereomers, removal of chiral auxiliary group, and further modifications thereafter. This route calls for a total of 6 to 10 steps of conversions to obtain the target molecules, in which a chromatographic separation of diastereomers is required. In the synthesis of IBR120, catalytic stereoselective arylation methods were employed to satisfactorily obtain the chiral starting material 24. The oxidation/reduction and ring closure reactions were further improved to achieve moderate to high yields of the desired enantiomers. It is noteworthy that these steps were performed under very mild conditions, which is a very attractive feature of this synthetic route.

These results also demonstrate that IBR120 can disrupt RAD51 multimer formation in vitro, and inhibit HR repair in cells, leading to growth inhibition and cell death.

Synthesis of Compounds of the Invention

All reagents were used as received from commercial sources, unless specified otherwise, or prepared as described in the literature. Reactions requiring anhydrous conditions were performed in vacuum heat-dried glassware under nitrogen atmosphere. Reaction mixtures were stirred magnetically. DMF, dichloromethane and pyridine were distilled from $CaH_2$. $^1H$ NMR spectra were recorded at either 400 MHz or 500 MHz. $^{13}C$ NMR spectra were recorded at either 125 MHz or 100 MHz. $^{19}F$ NMR spectra were recorded at 376 MHz with $FCCl_3$ as external standard and low field is positive. Chemical shifts (δ) are reported in ppm, and coupling constants (J) are in Hz. The following abbreviations were used to explain the multiplicities: s=singlet, d=doublet, t=triplet, q=quartet, m=multiplet.

(R)-2-Methylpropane-2-sulfinic acid [[2-(2-benzyloxy-ethyl)phenyl]-(1H-indazol-3-yl)-methyl]amide (6)

A solution of compound 5 (1.34 g, 6.85 mmol) in THF (40 mL) was cooled to −78°C. and n-BuLi (1.6 M in hexane, 4.28 mL, 6.95 mmol) was added dropwise. The resultant solution was stirred at −78°C. for 5 min. After that, t-BuLi (1.7 M in pentane, 8.06 mL, 13.70 mmol) was added dropwise and the resultant solution was stirred for 15 min at −78°C. Then, a solution of compound 2 (2.35 g, 6.85 mmol) (Qiu et al., 2009, J. Org. Chem. 74:2018-2027) in THF (8 mL) was added dropwise. The mixture was stirred for 1 h at −78°C. before saturated aqueous $NH_4Cl$ (3 mL) was added to quench the reaction. After the mixture was warmed up to room temperature, the mixture was poured to $H_2O$ (200 mL) and extracted with $CH_2Cl_2$ (3×60 mL). The combined organic phases were dried over anhydrous $Na_2SO_4$. The solvent was removed in vacuo and the resultant residue was purified by silica gel chromatography (hexane/EtOAc/$NH_3$=100:50:1) to give compound 6 (1.36 g, 43%) as a yellow foam. $^1H$ NMR (500 MHz, $CDCl_3$) δ 7.43 (d, J=8.0 Hz, 0.17H), 7.37-7.33 (m, 1.83H), 7.31-7.23 (m, 8H), 7.17-7.06 (m, 2H), 6.91 (t, J=8.8 Hz, 0.83H), 6.83 (d, J=9.0 Hz, 0.17H), 6.78 (t, J=7.5 Hz, 0.17H), 6.73 (t, J=8.0 Hz, 0.83H), 6.36 (d, J=6.5 Hz, 0.83H), 6.24 (d, J=2.5 Hz, 0.17H), 6.00 (d, J=6.5 Hz, 1H), 4.48 (s, 1.66H), 4.28-4.22 (m, 0.34H), 3.78-3.69 (m, 1.66H), 3.46-3.41 (m, 0.34H), 3.33-3.23 (m, 1.66H), 3.20-3.07 (m, 0.34H), 1.29 (s, 1.5H), 1.27 (s, 7.5H); $^{13}C$ NMR (125 MHz, $CDCl_3$) δ 144.9, 144.9, 141.5, 141.5, 139.5, 138.5, 138.4, 138.1, 136.5, 130.9, 130.3, 128.8, 128.5, 128.5, 128.4, 128.0, 127.8, 127.7, 127.7, 127.5, 126.9, 126.8, 126.5, 126.4, 120.9, 120.9, 120.5, 120.5, 120.4, 120.3, 110.7, 110.7, 73.2, 72.9, 71.1, 70.7, 56.9, 56.6, 54.5, 54.4, 33.0, 32.8, 23.4, 23.0; MS (ESI) m/z 484 (M+Na+); HRMS Calcd for $C_{27}H_{31}N_3O_2SNa$ (M+Na'), 484.2035 Found: 484.2021.

3-[(S)-[2-(2-Benzyloxyethyl)phenyl]-((R)-2-methyl-propane-2-sulfinylamino)methyl]indazole-1-carboxylic acid tert-butyl ester (7) and 3-[(R)-[2-(2-Benzyloxyethyl)phenyl]-((R)-2-methyl-propane-2-sulfinylamino)methyl]indazole-1-carboxylic acid tert-butyl ester (8)

To a 0 °C. solution of compound 6 (706 mg, 1.53 mmol) in $CH_2Cl_2$ (20 mL) was added DMAP (5.0 mg, 0.04 mmol) followed by a solution of $Boc_2O$ (350 mg, 1.60 mmol) in $CH_2Cl_2$ (2.0 mL). The mixture was warmed up to room temperature and stirred for 1 h. Removal of all the solvent in vacuo resulted in a residue, which was purified by silica gel chromatography (hexane/EtOAc=3:1 to 2:1) to give compound 8 (less polar, 117 mg, 14%) as an oil and compound 7 (more polar, 565 mg, 66%) as an oil.

Compound 7: $[α]_D^{20}$=+7.3 (c 0.9 $CH_2Cl_2$); $^1H$ NMR (500 MHz, $CDCl_3$) δ 8.13 (d, J=9.0 Hz, 1H), 7.50 (d, J=8.0 Hz, 1H), 7.44 (t, J=8.0 Hz, 1H), 7.33-7.19 (m, 8H), 7.15-7.10 (m, 2H), 6.42 (d, J=3.0 Hz, 1H), 4.54-4.48 (m, 2H), 4.28 (d, J=3.0 Hz, 1H), 3.86-3.76 (m, 2H), 3.27 (t, J=6.5 Hz, 2H), 1.70 (s, 9H), 1.25 (s, 9H); $^{13}C$ NMR (125 MHz, $CDCl_3$) δ 150.9, 149.4, 141.2, 138.4, 138.2, 138.0, 130.8, 128.9, 128.7, 128.7, 128.5, 127.7, 127.6, 127.0, 124.3, 123.4, 121.7, 114.9, 84.7, 73.1, 70.9, 56.5, 54.1, 32.5, 28.4, 23.0; MS (ESI) m/z 584 (M+Na+); HRMS Calcd for $C_{32}H_{39}N_3O_4SNa$ (M+Na+), 584.2559 Found: 584.2560.

Compound 8: $[α]_D^{20}$=−112 (c 1.1 $CH_2Cl_2$); $^1H$ NMR (500 MHz, $CDCl_3$) δ 8.07 (d, J=8.0 Hz, 1H), 7.39 (dd, J=18.5, 7.5 Hz, 2H), 7.32-7.17 (m, 9H), 7.02-6.96 (m, 2H), 6.26 (d, J=2.5 Hz, 1H), 4.44-4.36 (m, 2H), 3.69-3.61 (m, 2H), 3.29-3.23 (m, 1H), 3.16-3.10 (m, 1H), 1.71 (s, 9H), 1.25 (s, 9H); $^{13}C$ NMR (125 MHz, $CDCl_3$) δ 150.8, 149.2, 141.2, 138.5, 138.4, 137.4, 130.8, 130.3, 129.0, 128.7, 128.5, 127.7, 127.6, 127.1, 123.8, 123.6, 121.2, 114.8, 84.8, 73.1, 70.9, 56.1, 53.4, 33.0, 28.4, 22.9; MS (ESI) m/z 584 (M+Na+); HRMS Calcd for $C_{32}H_{39}N_3O_4SNa$ (M+Na+), 584.2559 Found: 584.2559.

3-[(R)-Amino-[2-(2-benzyloxyethyl)phenyl]methyl]indazole-1-carboxylic acid tert-butyl ester (9)

To a solution of compound 8 (118 mg, 0.21 mmol) in MeOH (2.5 mL) was added 4M HCl solution (in dioxane, 2.5 mL). After the mixture was stirred at room temperature for 30 min, the mixture was diluted with $H_2O$ (100 mL) and saturated aqueous NaHCO$_3$ (20 mL) was added. Then, the resultant aqueous solution was extracted with CH$_2$Cl$_2$ (3×30 mL). The combined organic layers were washed with brine, and then dried over anhydrous Na$_2$SO$_4$. After filtration and removal of the solvent in vacuo, the residue was purified by silica gel column chromatography (CH$_2$Cl$_2$/MeOH/ NH$_3$=200:10:1) to afford compound 9 (87 mg, 90%) as a clear oil. [α]D$^{20}$=−85 (c 1.0 CH$_2$Cl$_2$); $^1$H NMR (500 MHz, CDCl$_3$) δ 8.03 (d, J=9.5 Hz, 1H), 7.41 (t, J=7.3 Hz, 1H), 7.28-7.21 (m, 8H), 7.15-7.10 (m, 2H), 7.03 (t, J=7.5 Hz, 1H), 5.89 (s, 1H), 4.51 (s, 2H), 3.78 (t, J=8.0 Hz, 2H), 3.22 (t, J=6.5 Hz, 2H), 2.98 (br, 2H), 1.73 (s, 9H); $^{13}$C NMR (125 MHz, CDCl$_3$) δ 154.0, 149.5, 140.9, 140.4, 138.3, 137.6, 130.6, 128.9, 128.6, 128.2, 128.0, 127.9, 127.8, 127.1, 124.1, 123.4, 121.5, 114.7, 85.0, 73.2, 71.3, 51.1, 33.1, 28.4; MS (ESI) m/z 480 (M+Na$^+$); HRMS Calcd for C$_{28}$H$_{32}$N$_3$O$_3$ (M+H$^+$), 458.2444 Found: 458.2424.

3-[(R)-Benzyloxycarbonylamino-[2-(2-hydroxyethyl)phenyl]methyl]indazole-1-carboxylic acid tert-butyl ester (10)

To a stirred solution of 9 (86 mg, 0.19 mmol) in MeOH (8 mL) was added 4M HCl in dioxane (0.4 mL), followed by Pd/C (50 mg, 10% Pd). The mixture was hydrogenated at room temperature under 1 atm for 1 h. Then, the mixture was filtrated and the filtrate was neutralized with a NaHCO$_3$ aqueous solution. The resulted mixture was extracted with CH$_2$Cl$_2$ (3×30 mL). The combined organic layers were washed with brine, and then dried over anhydrous Na$_2$SO$_4$. After filtration and removal of the solvent in vacuo, the residue was solved in CH$_2$Cl$_2$ (3 mL) and the solvent was cooled to 0°C. To this solvent was added DIPEA (40 μL, 0.23 mmol) followed by CbzCl (40 mg, 0.23 mmol) dropwise. The mixture was stirred at 0°C. for 20 min. Then, all the solvent was removed in vacuo and the residue was purified by silica gel chromatography (hexane/EtOAc=2:1) to give the compound 10 (57 mg, 61%) as a oil. [α]D$^{20}$=−95 (c 0.9 CH$_2$Cl$_2$); $^1$H NMR (400 MHz, CDCl$_3$) δ 8.04 (d, J=8.4 Hz, 1H), 7.44 (ddd, J=8.4, 7.2, 4.2 Hz, 1H), 7.33-7.22 (m, 9H), 7.16-7.11 (m, 2H), 6.66 (d, J=7.6 Hz, 1H), 6.55 (d, J=6.4 Hz, 1H), 5.14-5.05 (m, 2H), 3.97 (br, 2H), 3.31-3.25 (m, 1H), 3.22-3.16 (m, 1H), 2.77 (br, 1H), 1.72 (s, 9H); $^{13}$C NMR (125 MHz, CDCl$_3$) δ 156.1, 150.6, 149.2, 140.9, 138.2, 137.6, 136.4, 130.7, 129.2, 128.7, 128.7, 128.6, 128.3, 128.2, 127.3, 123.8, 123.8, 120.8, 114.9, 85.3, 67.3, 63.8, 50.6, 35.9, 28.4; MS (ESI) m/z 524 (M+Na$^+$); HRMS Calcd for C$_{29}$H$_{31}$N$_3$O$_5$Na (M+H$^+$), 524.2161 Found: 524.2156.

3-[(R)-Benzyloxycarbonylamino-[2-(2-methanesulfonyloxyethyl)phenyl]methyl]indazole-1-carboxylic acid tert-butyl ester (11)

Compound 10 (57 mg, 0.11 mmol) was dissolved in CH$_2$Cl$_2$ (3 mL) and DIPEA (40 μL, 0.23 mmol) were added. Then, MsCl (13 μL, 0.17 mmol) was added dropwise. The mixture was stirred at room temperature for 20 min. After that, the solvent was removed in vacuo and the residue was purified by silica gel column chromatography (hexane/ EtOAc=2:1) to afford 11 (60 mg, 91%) as a white foam. [α]D$^{20}$=−88 (c 0.8 CH$_2$Cl$_2$); $^1$H NMR (400 MHz, CDCl$_3$) δ 8.06 (d, J=8.4 Hz, 1H), 7.47 (ddd, J=8.4, 7.2, 1.2 Hz, 1H), 7.34-7.26 (m, 9H), 7.22-7.15 (m, 2H), 6.54 (d, J=7.2 Hz, 1H), 6.41 (d, J=6.8 Hz, 1H), 5.15-5.07 (m, 2H), 5.48-4.43 (m, 2H), 3.39 (s, 2H), 2.84 (s, 3H), 1.73 (s, 9H); $^{13}$C NMR (125 MHz, CDCl$_3$) δ 155.9, 150.1, 149.1, 140.9, 138.2, 136.4, 134.6, 131.0, 129.4, 129.2, 128.7, 128.7, 128.3, 128.2, 128.0, 124.0, 123.6, 120.7, 115.0, 85.5, 70.2, 67.3, 50.8, 37.3, 32.2, 28.4; MS (ESI) m/z 602 (M+Na$^+$); HRMS Calcd for C$_{30}$H$_{33}$N$_3$O$_7$SNa (M+Na$^+$), 602.1937 Found: 602.1948.

(R)-3-(1,2,3,4-Tetrahydro-isoquinolin-1-yl)indazole-1-carboxylic acid tert-butyl ester (12)

To a solution of compound 11 (60 mg, 0.10 mmol) in MeOH (4 mL) was added Pd/C (55 mg, 10% Pd). The mixture was hydrogenated at room temperature under 1 atm for 1 h. Then, the solvent was removed in vacuo and the residue was purified by silica gel column chromatography (CH$_2$Cl$_2$/MeOH/NH$_3$=150:10:1) to afford 12 (34 mg, 94%) as a foam. [α]D$^{20}$=+106 (c 1.0 CH$_2$Cl$_2$); $^1$H NMR (500 MHz, CDCl$_3$) δ 8.06 (d, J=9.0 Hz, 1H), 7.41 (ddd, J=7.5, 7.5, 0.8 Hz, 1H), 7.22-7.15 (m, 3H), 7.08 (dd, J=7.8, 7.5 Hz, 1H), 6.99 (t, J=7.5 Hz, 1H), 6.86 (d, J=8.0 Hz, 1H), 5.68 (s, 1H), 3.41-3.36 (m, 1H), 3.24-3.16 (m, 2H), 2.91-2.86 (m, 1H), 2.21 (br, 1H), 1.75 (s, 9H); $^{13}$C NMR (125 MHz, CDCl$_3$) δ 153.9, 149.6, 141.1, 135.4, 135.3, 129.4, 128.8, 127.8, 127.0, 126.2, 124.2, 123.5, 122.5, 114.8, 85.2, 56.4, 43.3, 30.0, 28.5; MS (ESI) m/z 372 (M+Na$^+$); HRMS Calcd for C$_{21}$H$_{23}$N$_3$O$_2$Na (M+Na$^+$), 372.1688 Found: 372.1687.

(R)-1-(1H-Indazol-3-yl)-2-phenylmethanesulfonyl-1,2,3,4-tetrahydroisoquinoline (IBR117)

To a solution of compound 12 (34 mg, 0.097 mmol) in MeOH (1 mL) was added a solution of NaOMe (2.7 mg, 0.05 mmol) in MeOH (0.1 mL). The resultant mixture was stirred at room temperature for 3 h. CH$_2$Cl$_2$ (20 mL) and H$_2$O (50 mL) were added to dilute the mixture and the aqueous phase was extracted with CH$_2$Cl$_2$ (3×25 mL). The combined organic layers were dried over anhydrous Na$_2$SO$_4$. Removal of all the solvent in vacuo gave a residue, which was dissolved in CH$_2$Cl$_2$ (1 mL). The resultant solution was cooled to 0°C. and DIPEA (22 μL, 0.13 mmol) was added. Then, a solution of BnSO$_2$Cl (20 mg, 0.10 mmol) in CH$_2$Cl$_2$ (0.25 mL) was added dropwise. The mixture was stirred at 0°C. for 20 min. Removal of all the solvent gave a residue, which was purified by silica gel chromatography (hexane/EtOAc=2:1) to afford compound IBR117 (24 mg, 61%) as a white foam. [α]D$^{20}$=+93 (c 0.6 CH$_2$Cl$_2$); $^1$H NMR (500 MHz, CDCl$_3$) δ 10.43 (br, 1H), 7.56 (dd, J=8.3, 3.5 Hz, 1H), 7.50 (d, J=8.5 Hz, 1H), 7.40 (t, J=7.5 Hz, 1H), 7.26-7.10 (m, 5H), 7.07 (t, J=7.5 Hz, 2H), 6.97 (d, J=8.0 Hz, 1H), 6.79 (d, J=7.5 Hz, 2H), 6.63 (s, 1H), 4.07-3.97 (m, 2H), 3.52 (dd, J=14.0, 6.5 Hz, 1H), 3.28 (ddd, J=12.5, 12.0, 3.5 Hz, 1H), 3.02 (ddd, J=17.0, 11.5, 6.0 Hz, 1H), 2.77 (dd, J=17.0, 2.5 Hz, 1H); $^{13}$C NMR (125 MHz, CDCl$_3$) δ 146.7, 141.3, 134.1, 133.9, 130.7, 129.5, 128.8, 128.5, 128.5, 128.2, 127.6, 127.4, 126.6, 122.1, 121.8, 121.0, 110.2, 59.4, 53.2, 40.8, 29.1; MS (ESI) m/z 426 (M+Na$^+$); HRMS Calcd for C$_{23}$H$_{22}$N$_3$O$_2$S (M+H$^+$), 404.1433 Found: 404.1430.

3-[(S)-Amino-[2-(2-benzyloxyethyl)phenyl]methyl] indazole-1-carboxylic acid tert-butyl ester (13)

Compound 13 (203 mg, 91%) was prepared as a clear oil using the same conditions as described for compound 9. [α]D$^{20}$=+85 (c 1.0 CH$_2$Cl$_2$); $^1$H NMR (500 MHz, CDCl$_3$) δ 8.03 (d, J=8.5 Hz, 1H), 7.41 (t, J=9.5 Hz, 1H), 7.30-7.20 (m, 8H), 7.16-7.10 (m, 2H), 7.03 (t, J=7.5 Hz, 1H), 5.89 (s, 1H), 4.51 (s, 2H), 3.78 (t, J=7.3 Hz, 2H), 3.22 (t, J=7.0 Hz, 2H), 2.99 (br, 2H), 1.73 (s, 9H); $^{13}$C NMR (125 MHz, CDCl$_3$) δ 154.0, 149.5, 140.9, 140.4, 138.3, 137.6, 130.6, 128.9, 128.5, 128.2, 128.0, 127.9, 127.8, 127.1, 124.1, 123.4, 121.5, 114.7, 85.0, 73.2, 71.3, 51.1, 33.1, 28.4; MS (ESI) m/z 458 (M+H$^+$); HRMS Calcd for C$_{28}$H$_{32}$N$_3$O$_3$ (M+H$^+$), 458.2444 Found: 458.2435.

3-[(S)-Benzyloxycarbonylamino-[2-(2-hydroxyethyl)phenyl]methyl]indazole-1-carboxylic acid tert-butyl ester (14)

Compound 14 (159 mg, 71%) was prepared as a white foam using the same conditions as described for compound 10. [α]D$^{20}$=+99 (c 0.9 CH$_2$Cl$_2$); $^1$H NMR (400 MHz, CDCl$_3$) δ 8.04 (d, J=8.4 Hz, 1H), 7.44 (ddd, J=8.4, 7.2, 1.2 Hz, 1H), 7.33-7.22 (m, 9H), 7.16-7.11 (m, 2H), 6.65 (d, J=7.2 Hz, 1H), 6.55 (d, J=6.4 Hz, 1H), 5.14-5.05 (m, 2H), 3.96 (br, 2H), 3.31-3.25 (m, 1H), 3.22-3.15 (m, 1H), 2.77 (br, 1H), 1.72 (s, 9H); $^{13}$C NMR (125 MHz, CDCl$_3$) δ 156.1, 150.6, 149.2, 140.9, 138.2, 137.6, 136.4, 130.7, 129.2, 128.7, 128.7, 128.6, 128.3, 128.2, 127.3, 123.8, 123.8, 120.8, 114.9, 85.3, 67.3, 63.8, 50.7, 35.9, 28.4; MS (ESI) m/z 524 (M+Na$^+$); HRMS Calcd for C$_{29}$H$_{31}$N$_3$O$_5$Na (M+Na$^+$), 524.2161 Found: 524.2169.

3-[(S)-Benzyloxycarbonylamino-[2-(2-methanesulfonyloxyethyl)phenyl]methyl]indazole-1-carboxylic acid tert-butyl ester (15)

Compound 15 (161 mg, 88%) was prepared as a white foam using the same conditions as described for the compound 11. [α]D$^{20}$=+86 (c 1.2 CH$_2$Cl$_2$); $^1$H NMR (400 MHz, CDCl$_3$) δ 8.06 (d, J=8.4 Hz, 1H), 7.47 (ddd, J=8.4, 7.2, 0.8 Hz, 1H), 7.34-7.26 (m, 9H), 7.22-7.15 (m, 2H), 6.54 (d, J=7.2 Hz, 1H), 6.41 (d, J=5.6 Hz, 1H), 5.15-5.07 (m, 2H), 5.57-4.43 (m, 2H), 3.39 (s, 2H), 2.84 (s, 3H), 1.73 (s, 9H); $^{13}$C NMR (125 MHz, CDCl$_3$) δ 155.9, 150.1, 149.2, 140.9, 138.2, 136.4, 134.6, 131.0, 129.4, 129.2, 128.7, 128.7, 128.3, 128.2, 128.0, 124.0, 123.6, 120.7, 115.0, 85.4, 70.1, 67.3, 50.8, 37.3, 32.2, 28.4; MS (ESI) m/z 602 (M+Na$^+$); HRMS Calcd for C$_{30}$H$_{33}$N$_3$O$_7$SNa (M+Na$^+$), 602.1937 Found: 602.1941.

(S)-3-(1,2,3,4-Tetrahydro-isoquinolin-1-yl)indazole-1-carboxylic acid tert-butyl ester (16)

Compound 16 (95 mg, 97%) was prepared as a white foam using the same conditions as described for the compound 12. [α]D$^{20}$=−108 (c 0.7 CH$_2$Cl$_2$); $^1$H NMR (500 MHz, CDCl$_3$) δ 8.06 (d, J=8.5 Hz, 1H), 7.41 (ddd, J=7.5, 7.3, 0.8 Hz, 1H), 7.22-7.15 (m, 3H), 7.07 (t, J=7.5 Hz, 1H), 6.99 (t, J=4.0 Hz, 1H), 6.86 (d, J=8.0 Hz, 1H), 5.68 (s, 1H), 3.41-3.36 (m, 1H), 3.24-3.16 (m, 2H), 2.91-2.86 (m, 1H), 2.21 (br, 1H), 1.75 (s, 9H); $^{13}$C NMR (125 MHz, CDCl$_3$) δ 153.9, 149.5, 141.1, 135.4, 135.3, 129.4, 128.8, 127.7, 127.0, 126.1, 124.2, 123.5, 122.5, 114.8, 85.2, 56.4, 43.3, 29.9, 28.5; MS (ESI) m/z 350 (M+H$^+$); HRMS Calcd for C$_{21}$H$_{24}$N$_3$O$_2$ (M+H$^+$), 350.1869 Found: 350.1863.

(S)-1-(1H-Indazol-3-yl)-2-phenylmethanesulfonyl-1,2,3,4-tetrahydroisoquinoline (IBR118)

IBR118 (73 mg, 67%) was prepared as white foam using the same conditions as described for the compound IBR117. [α]D$^{20}$=−90 (c 0.8 CH$_2$Cl$_2$); $^1$H NMR (500 MHz, CDCl$_3$) δ 10.43 (br, 1H), 7.55 (dd, J=8.0, 3.0 Hz, 1H), 7.50 (d, J=8.5 Hz, 1H), 7.40 (t, J=7.0 Hz, 1H), 7.26-7.10 (m, 5H), 7.06 (t, J=7.0 Hz, 2H), 6.97 (d, J=8.0 Hz, 1H), 6.79 (d, J=7.5 Hz, 2H), 6.63 (s, 1H), 4.07-3.97 (m, 2H), 3.53 (dd, J=12.5, 6.5 Hz, 1H), 3.28 (ddd, J=12.5, 12.0, 3.5 Hz, 1H), 3.02 (ddd, J=18.0, 11.5, 6.0 Hz, 1H), 2.77 (dd, J=17.0, 3.0 Hz, 1H); $^{13}$C NMR (125 MHz, CDCl$_3$) δ 146.7, 141.3, 134.1, 140.0, 130.7, 129.5, 128.8, 128.5, 128.5, 128.2, 127.6, 127.4, 126.6, 122.1, 121.8, 121.0, 110.2, 59.4, 53.2, 40.8, 29.1; MS (ESI) m/z 426 (M+Na$^+$); HRMS Calcd for C$_{23}$H$_{21}$N$_3$O$_2$SNa (M+Na$^+$), 426.1252 Found: 426.1252.

[5-[(R)-[2-(2-Benzyloxyethyl)phenyl]-((R)-2-methylpropane-2-sulfinylamino)methyl]thiazol-2-yl]carbamic acid tert-butyl ester (18) and [5-[(S)-[2-(2-Benzyloxyethyl)phenyl]-((R)-2-methylpropane-2-sulfinylamino)methyl]thiazol-2-yl]carbamic acid tert-butyl ester (19)

A solution of compound 17 (390 mg, 1.40 mmol) in THF (8 mL) was cooled to −78°C. and n-BuLi (2.86 M, 1.22 mL, 3.50 mmol) was added slowly. The resultant mixture was stirred at −78°C. for 20 min. After that, a solution of compound 2 (480 mg, 1.40 mmol) in THF (4 mL) was added slowly. The mixture was stirred at −78°C. for 20 min. Saturated aqueous NH$_4$Cl (5 mL) was added to quench the reaction and the mixture was warmed up to room temperature. H$_2$O (50 mL) was added and the mixture was extracted with CH$_2$Cl$_2$ (3×30 mL). The combined organic phases were dried over anhydrous Na$_2$SO$_4$. Removal of the solvent in vacuo resulted in a residue, which was purified by silica gel chromatography (hexane/EtOAc/NH$_3$=100/200/0.6 to 100/200/3) to give compound 19 (less polar, 235 mg, 31%) as a foam and compound 18 (more polar, 60 mg, 7.9%) as a foam.

Compound 18: [α]D$^{20}$=−55.8 (c 0.88 CH$_2$Cl$_2$); $^1$H NMR (500 MHz, CDCl$_3$) δ 11.73 (s, 1H), 7.60 (d, J=8.0 Hz, 1H), 7.30-7.18 (m, 8H), 7.15 (s, 1H), 6.12 (d, J=2.5 Hz, 1H), 4.53-4.46 (m, 2H), 3.81 (d, J=2.5 Hz, 1H), 3.73-3.68 (m, 1H), 3.66-3.61 (m, 1H), 3.08-2.95 (m, 2H), 1.49 (s, 9H), 1.22 (s, 9H); $^{13}$C NMR (125 MHz, CDCl$_3$) δ 162.3, 153.0, 138.5, 138.5, 137.0, 135.1, 133.3, 130.8, 128.5, 128.3, 127.8, 127.8, 127.6, 127.2, 82.4, 73.2, 70.7, 56.2, 51.9, 33.2, 28.4, 22.9; MS (ESI) m/z 566 (M+Na$^+$); HRMS Calcd for C$_{28}$H$_{37}$N$_3$O$_4$S$_2$Na (M+Na$^+$), 566.2123 Found: 566.2122.

Compound 19: [α]D$^{20}$=+3.5 (c 0.83 CH$_2$Cl$_2$); $^1$H NMR (500 MHz, CDCl$_3$) δ 7.52 (d, J=7.0 Hz, 1H), 7.29-7.18 (m, 9H), 7.11 (s, 1H), 6.06 (s, 1H), 4.49 (s, 2H), 4.00 (br, 1H), 3.68-3.60 (m, 2H), 3.02 (t, J=6.5 Hz, 2H), 1.47 (s, 9H), 1.24 (s, 9H); $^{13}$C NMR (125 MHz, CDCl$_3$) δ 162.6, 152.8, 139.6, 138.3, 136.7, 132.8, 130.7, 128.6, 128.5, 127.8, 127.7, 127.5, 127.1, 82.5, 73.2, 70.6, 56.3, 52.9, 32.9, 28.4, 23.0; MS (ESI) m/z 566 (M+Na$^+$); HRMS Calcd for C$_{28}$H$_{37}$N$_3$O$_4$S$_2$Na (M+Na$^+$), 566.2123 Found: 566.2128.

(5-[(S)-Amino-[2-(2-benzyloxyethyl)phenyl]methyl]thiazol-2-yl)carbamic acid tert-butyl ester (20)

To a solution of compound 19 (219 mg, 0.40 mmol) in MeOH (5 mL) was added 4 M HCl in dioxane (5 mL). The mixture was stirred at room temperature for 30 min. After that, the mixture was poured to an aqueous NaHCO$_3$ (2.0 g in 50 mL H$_2$O). The mixture was extracted with CH$_2$Cl$_2$ (3×30 mL). The combined organic phases were dried over anhydrous Na$_2$SO$_4$. Removal of the solvent in vacuo resulted in a residue, which was purified by silica gel chromatography (CH$_2$Cl$_2$/MeOH/NH$_3$=200/20/1) to afford compound 20 (178 mg, quant.) as an oil. [α]D$^{20}$=+49.3 (c 0.94 CH$_2$Cl$_2$); $^1$H NMR (500 MHz, CDCl$_3$) δ 7.51 (d, J=7.5

Hz, 1H), 7.31-7.17 (m, 8H), 6.90 (s, 1H), 5.59 (s, 1H), 4.47 (s, 2H), 3.67-3.59 (m, 3H), 3.07-3.01 (m, 1H), 2.94-2.88 (m, 1H), 2.26 (br, 2H), 1.43 (s, 9H); $^{13}$C NMR (125 MHz, CDCl$_3$) δ 161.6, 153.0, 142.4, 138.3, 136.6, 136.2, 133.7, 130.3, 128.6, 127.8, 127.8, 127.8, 127.3, 126.6, 81.9, 73.3, 71.2, 49.7, 33.1, 28.4; MS (ESI) m/z 462 (M+Na$^+$); HRMS Calcd for C$_{24}$H$_{29}$N$_3$O$_3$SNa (M+Na$^+$), 462.1827 Found: 462.1828.

(5-[(S)-[2-(2-Benzyloxyethyl)phenyl]phenylmethanesulfonylamino-methyl]thiazol-2-yl)carbamic acid tert-butyl ester (21)

A solution of compound 20 (178 mg, 0.40 mmol) in CH$_2$Cl$_2$ (8 mL) was added DIPEA (116 μL, 0.65 mmol) and DMAP (8.0 mg, 0.066 mmol) at 0°C. Then, a solution of BnSO$_2$Cl (130 mg, 0.68 mmol) was added dropwise. The mixture was warmed up to room temperature and stirred for 20 min. Removal of the solvent in vacuo resulted in a residue, which was purified by silica gel chromatography (hexane/EtOAc=2/1) to give compound 21 (232 mg, 97%) as a yellow oil. [α]D$^{20}$=−33.6 (c 1.26 CH$_2$Cl$_2$); $^1$H NMR (500 MHz, CDCl$_3$) δ 12.06 (s, 1H), 7.35 (td, J=7.5, 1.5 Hz, 1H), 7.28-7.22 (m, 7H), 7.19-7.14 (m, 4H), 7.05 (s, 1H), 7.00 (d, J=7.0 Hz, 2H), 6.77 (br, 1H), 5.84 (d, J=8.0 Hz, 1H), 4.20-4.11 (m, 2H), 3.99 (s, 2H), 3.64 (dt, J=9.0, 4.5 Hz, 1H), 3.48 (ddd, J=9.5, 9.5, 4.5 Hz, 1H), 2.91 (ddd, J=14.5, 9.3, 4.5 Hz, 1H), 2.67 (dt, J=14.5, 5.0 Hz, 1H), 1.46 (s, 9H); $^{13}$C NMR (125 MHz, CDCl$_3$) δ 162.2, 153.0, 138.7, 138.3, 137.5, 135.1, 133.8, 132.8, 131.5, 131.1, 129.2, 129.1, 128.9, 128.7, 128.6, 128.2, 128.0, 127.3, 82.2, 73.1, 70.7, 59.9, 55.3, 33.1, 28.4; MS (ESI) m/z 616 (M+Na$^+$); HRMS Calcd for C$_{31}$H$_{35}$N$_3$O$_5$S$_2$Na (M+Na$^+$), 616.1916 Found: 616.1909.

(5-[(S)-[2-(2-Hydroxyethyl)phenyl]phenylmethanesulfonylamino-methyl]thiazol-2-yl)-carbamic acid tert-butyl ester (22)

To a solution of compound 21 (225 mg, 0.38 mmol) in MeOH (10 mL) was added Pd/C (10% Pd, 198 mg) and 4 M HCl in dioxane (0.5 mL). The, the mixture was hydrogenated (1 atm) for 5 h. The mixture was subjected to filtration and the filtrate was poured to H$_2$O (50 ml). Saturated aqueous NaHCO$_3$ (10 mL) was added and the mixture was extracted with CH$_2$Cl$_2$ (3×25 mL). The combined organic phases were dried over anhydrous Na$_2$SO$_4$. Removal of the solvent in vacuo resulted in a residue, which was purified by silica gel chromatography (CH$_2$Cl$_2$/MeOH=15/1) to afford compound 22 (152 mg, 80%) as a foam. [α]D$^{20}$=−41 (c 0.58 CH$_2$Cl$_2$); $^1$H NMR (500 MHz, CDCl$_3$) δ 7.37 (t, J=7.0 Hz, 2H), 7.32-7.24 (m, 4H), 7.20 (t, J=7.5 Hz, 2H), 7.03 (d, J=7.5 Hz, 2H), 6.97 (s, 1H), 6.50 (br, 1H), 5.96 (d, J=8.5 Hz, 1H), 4.21 (d, J=14.0 Hz, 1H), 4.07 (d, J=13.5 Hz, 1H), 3.80 (dt, J=9.5, 5.0 Hz, 1H), 3.71-3.65 (m, 1H), 2.81 (ddd, J=14.0, 9.3, 5.5 Hz, 1H), 2.68 (dt, J=14.5, 5.0 Hz, 1H), 1.46 (s, 9H); $^{13}$C NMR (125 MHz, CDCl$_3$) δ 162.0, 152.8, 139.1, 137.9, 135.3, 133.3, 131.6, 131.1, 129.3, 129.1, 128.7, 128.6, 127.5; 82.5, 64.1, 60.0, 54.7, 35.4, 28.4; MS (ESI) m/z 526 (M+Na$^+$); HRMS Calcd for C$_{24}$H$_{29}$N$_3$O$_5$S$_2$Na (M+Na$^+$), 526.1447 Found: 526.1442.

[5-((S)-2-Phenylmethanesulfonyl-1,2,3,4-tetrahydroisoquinolin-1-yl)thiazol-2-yl]carbamic acid tert-butyl ester (23)

To a solution of compound 22 (152 mg, 0.30 mmol) in CH$_2$Cl$_2$ (5 mL) was added DMAP (3.0 mg, 0.025 mmol) and DIPEA (63 μL, 0.36 mmol) at 0°C. Then, MsCl (80 μL, 1.03 mmol) was added dropwise. The mixture was stirred at room temperature for 20 min. After that, the solvent was removed in vacuo to afford a residue, which was purified by gel chromatography (CH$_2$Cl$_2$/MeOH=30/1) to give a foam (168 mg). The yielded foam (168 mg) was dissolved in THF (10 mL) and the solution was cooled to 0°C. To this solution was added KHMDS (0.5 M in toluene, 1.15 mL, 0.58 mmol) and the mixture was stirred at 0°C. for 5 min. The reaction was quenched with aqueous saturated NH$_4$Cl (5 mL) and H$_2$O (30 mL) was added. The mixture was extracted with CH$_2$Cl$_2$ (3×25 mL) and the combined organic phases were dried over anhydrous Na$_2$SO$_4$. The solvent was removed in vacuo and the resultant residue was purified by silica gel chromatography (hexane/EtOAc=2/1) to give compound 23 (118 mg, 81%) as a foam. [α]D$^{20}$=−50.7 (c 0.63 CH$_2$Cl$_2$); $^1$H NMR (500 MHz, CDCl$_3$) δ 11.92 (s, 1H), 7.27-7.24 (m, 1H), 7.21-7.17 (m, 3H), 7.14-7.09 (m, 5H), 6.97 (d, J=7.0 Hz, 1H), 6.08 (s, 1H), 4.13-4.08 (m, 2H), 3.63 (dd, J=14.0, 6.0 Hz, 1H), 3.29 (ddd, J=15.5, 10.5, 3.0 Hz, 1H), 2.82 (ddd, J=16.5, 12.0, 5.0 Hz, 1H), 2.67 (dt, J=15.0, 3.0 Hz, 1H), 1.47 (s, 9H); $^{13}$C NMR (125 MHz, CDCl$_3$) δ 162.5, 152.9, 136.8, 134.0, 133.5, 132.4, 130.9, 129.5, 128.8, 128.7, 128.7, 128.2, 127.9, 126.6, 82.4, 59.6, 53.4, 39.9, 29.9, 28.5; MS (ESI) m/z 508 (M+Na$^+$); HRMS Calcd for C$_{24}$H$_{27}$N$_3$O$_4$S$_2$Na (M+Na$^+$), 508.1341 Found: 508.1344.

5-((S)-2-Phenylmethanesulfonyl-1,2,3,4-tetrahydroisoquinolin-1-yl)thiazol-2-ylamine (IBR119)

To a solution of compound 23 (106 mg, 0.22 mmol) in CH$_2$Cl$_2$ (10 mL) was added TFA (1 mL) at 0°C. The mixture was warmed up to room temperature and stirred for 5 h. CH$_2$Cl$_2$ (20 mL) and H$_2$O (30 mL) were added to the reaction mixture. The reaction was quenched with aqueous saturated NH$_4$Cl (5 mL) and H$_2$O (30 mL) was added. After saturated aqueous NaHCO$_3$ (10 ml) was added, the mixture was extracted with CH$_2$Cl$_2$ (3×20 mL) and the combined organic phases were dried over anhydrous Na$_2$SO$_4$. The solvent was removed in vacuo and the resultant residue was purified by silica gel chromatography (hexane/EtOAc/NH3=1:1:0 to 1:2:0.005) to give compound IBR119 (73 mg, 87%) as a foam. [α]D$^{20}$=−62.9 (c 0.43 CH$_2$Cl$_2$); $^1$H NMR (500 MHz, CDCl$_3$) δ 7.19-7.26 (m, 1H), 7.24-7.19 (m, 3H), 7.16-7.10 (m, 4H), 6.98 (d, J=8.0 Hz, 1H), 6.61 (s, 1H), 5.93 (s, 1H), 5.07 (br, 2H), 4.19-4.10 (m, 2H), 3.62 (dd, J=14.3, 6.0 Hz, 1H), 3.22 (ddd, J=15.5, 10.5, 3.5 Hz, 1H), 2.78 (ddd, J=17.8, 11.3, 5.0 Hz, 1H), 2.66 (dd, J=16.5, 1.5 Hz, 1H); $^{13}$C NMR (125 MHz, CDCl$_3$) δ 169.1, 138.9, 133.8, 133.6, 130.9, 129.4, 129.3, 128.8, 128.7, 128.7, 128.3, 127.9, 126.5, 59.8, 53.7, 39.6, 29.9; MS (ESI) m/z 386 (M+H$^+$); HRMS Calcd for C$_{19}$H$_{20}$N$_3$O$_2$S$_2$ (M+H$^+$), 386.0997 Found: 386.0996.

(R)—N-((2-(hydroxymethyl)phenyl)(1H-indol-3-yl)methyl)-1-phenylmethanesulfonamide (25)

To a solution of compound 24 (176 mg, 0.44 mmol) (Qiu et al., 2009, J. Org. Chem. 74:2018-2027) in dioxane-water (3:1, 8 mL) were added 2, 6-lutidine (0.101 mL, 0.88 mmol), OsO$_4$ (2.5% in tert-butanol, 89 μL, 8.8 μmol) and NaIO$_4$ (371.4 mg, 1.75 mmol). The reaction was stirred at r.t and monitored by TLC. After the reaction was complete, water (10 mL) and CH$_2$Cl$_2$ (20 mL) were added. The organic layer was separated, and the water layer was extracted by CH$_2$Cl$_2$ (10 mL×3). The combined organic layers were washed with brine and dried over Na$_2$SO$_4$. The solvent was removed under reduced pressure. The residue was absorbed onto SiO$_2$, and eluted with EtOAc/hexane (1:3) to afford the aldehyde intermediate as white foam (158 mg). This foam was dissolved in THF-MeOH (1:1, 4 mL) at 0°C. and NaBH$_4$ (44 mg, 1.17 mmol) in THF (1 mL) was added. The reaction was stirred for 10 min at room temperature and saturated aqueous NH$_4$Cl (3 mL) was added to quench the reaction. H$_2$O (30 mL) was added and the mixture was extracted with Et$_2$O (3×20 mL). The combined organic phases were dried with anhydrous Na$_2$SO$_4$. The solvent was removed under reduced pressure and the residue was absorbed onto silica gel and eluted with hexane/EtOAc (1:2) to give compound 25 (146 mg, 82%) as a foam. [α]D$^{20}$=+70.2 (c 1.06 CH$_2$Cl$_2$); $^1$H NMR (400 MHz, CD$_2$Cl$_2$) δ 8.26 (s, 1H), 7.62 (d, J=7.5 Hz, 1H), 7.36-7.52 (m, 6H), 7.15-7.31 (m, 4H), 7.02-7.04 (d, J=7.5 Hz, 2H), 6.94 (s, 1H), 6.27 (d, J=7.5 Hz, 1H), 5.76 (d, J=7.8 Hz, 1H), 4.47-4.57 (m, 2H), 4.13 (d, J=13.8 Hz, 1H), 4.02 (d, J=13.8 Hz, 1H), 1.80 (t, J=6.0 Hz, 1H); $^{13}$C NMR (100 MHz, CDCl$_3$) δ140.1, 138.2, 136.9, 130.9, 130.7, 129.1, 129.0, 128.9, 128.7, 128.6, 128.6, 128.6, 125.5, 123.8, 122.6, 120.1, 119.6, 116.0, 111.6, 63.3, 60.1, 53.8; MS (ESI) m/z 429 (M+Na$^+$); HRMS Calcd for C$_{23}$H$_{22}$N$_2$O$_3$SNa (M+Na$^+$), 429.1249 Found: 429.1230.

(R)-3-(2-(benzylsulfonyl)isoindolin-1-yl)-1H-indole (IBR120)

To a stirred solution of compound 25 (28 mg, 0.069 mmol) in CH$_2$Cl$_2$ (2.0 mL) was added Et$_3$N (9.6 μL, 0.069 mmol) at 0°C. Then, MsCl (7.1 μL, 0.092 mmol) was added dropwise. The mixture was warmed up to room temperature and stirred for 1 h. The reaction solution was diluted with CH$_2$Cl$_2$ (5 ml) and washed with ice water. Organic phases were dried with anhydrous Na$_2$SO$_4$ and removed under vacuum. The residue was then dissolved in dry MeCN (2 mL) and to this solution was added DIPEA dropwise at 0°C. The reaction was allowed warm up to r.t and monitored by TLC. After the reaction was completed, saturated aqueous NH$_4$Cl (1 mL) was added and the mixture was extracted with CH$_2$Cl$_2$ (3×5 mL). The combined organic phases were dried over anhydrous Na$_2$SO$_4$. Removal of the solvent in vacuo resulted in a residue, which was purified by silica gel chromatography (EtOAc/hexane=1:3) to give compound IBR120 (14.2 mg, 53%) as a white solid. [α]D$^{20}$=+89.5 (c 0.44 CH$_2$Cl$_2$); $^1$H NMR (400 MHz, CD$_2$Cl$_2$) δ 8.40 (s, 1H), 7.37-7.42 (m, 2H), 7.31-7.37 (t, J=7.3 Hz, 1H), 7.21-7.30 (m, 3H), 7.13-7.19 (m, 3H), 7.03-7.07 (d, J=7.6 Hz, 1H), 6.85-6.97 (m, 4H), 6.41 (d, J=1.8 Hz, 1H), 4.86 (d, J=13.3 Hz, 1H), 4.38-4.42 (dd, J=2.8, 13.6 Hz, 1H), 3.75 (d, J=13.6 Hz, 1H), 3.64 (d, J=13.7 Hz, 1H); $^{13}$C NMR (125 MHz, CD$_2$Cl$_2$) δ 140.7, 137.4, 136.5, 131.2, 129.7, 128.8, 128.7, 128.5, 128.4, 125.9, 125.7, 124.0, 122.9, 122.8, 120.4, 120.1, 116.0, 112.1, 63.2, 59.5, 54.2; MS (ESI) m/z 411 (M+Na$^+$); HRMS Calcd for C$_{23}$H$_{20}$N$_2$O$_2$SNa (M+Na$^+$), 411.1143 Found: 411.1134.

(S)-3-(2-(benzylsulfonyl)isoindolin-1-yl)-1H-indole (IBR121)

IBR121 (13.6 mg, 51%) was prepared as white solid using the same conditions as described for the compound IBR120. [α]D$^{20}$=−90.1 (c 0.75 CH$_2$Cl$_2$); $^1$H NMR (400 MHz, CD$_2$Cl$_2$) δ 8.37 (s, 1H), 7.39-7.42 (m, 2H), 7.32-7.35 (m, 1H), 7.22-7.28 (m, 3H), 7.13-7.17 (m, 3H), 7.03-7.05 (d, J=7.7 Hz, 1H), 6.85-6.96 (m, 4H), 6.41 (s, 1H), 4.85 (d, J=13.3 Hz, 1H), 4.37 (d, J=13.8 Hz, 1H), 3.74 (d, J=13.5 Hz, 1H), 3.63 (d, J=13.6 Hz, 1H); $^{13}$C NMR (125 MHz, CD$_2$Cl$_2$) δ 140.7, 137.3, 136.4, 131.2, 129.7, 128.7, 128.7, 128.4, 128.4, 125.7, 124.0, 122.9, 122.8, 120.4, 120.1, 116.0, 112.1, 63.1, 59.5, 54.2; MS (ESI) m/z 411 (M+Na$^+$); HRMS Calcd for C$_{23}$H$_{20}$N$_2$O$_2$SNa (M+Na$^+$), 411.1143 Found: 411.1150.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A compound selected from the group consisting of formula (I), formula (II), and formula (III), a salt or solvate, and any combinations thereof:

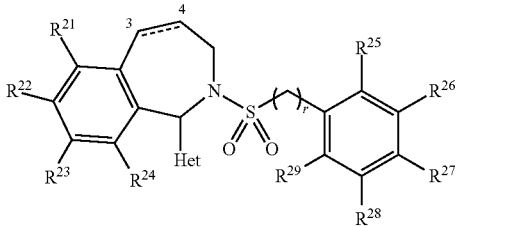

wherein:
$R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{27}$, $R^{28}$, and $R^{29}$ are each independently selected from the group consisting of H, $C_1$-$C_6$ alkyl, $C_1$-$C_6$ fluoroalkyl, $C_1$-$C_6$ heteroalkyl, F, Cl, Br, I, CN, NO$_2$, OR$^{30}$, SR$^{30}$, S(=O)R$^{30}$, S(=O)$_2$R$^{30}$, NHS(=O)$_2$R$^{30}$, C(=O)R$^{30}$, OC(=O)R$^{30}$, CO$_2$R$^{30}$, OCO$_2$R$^{30}$, CH(R$^{30}$)$_2$, N(R$^{30}$)$_2$, C(=O)N(R$^{30}$)$_2$, OC(=O)N(R$^{30}$)$_2$, NHC(=O)NH(R$^{30}$), NHC(=O)R$^{30}$, NHC(=O)OR$^{30}$, C(OH)(R$^{30}$)$_2$, and C(NH$_2$)(R$^{30}$)$_2$;
each occurrence of R$^{30}$ is independently selected from the group consisting of H and $C_1$-$C_6$ alkyl;

Het is a 5- to 14-membered substituted or unsubstituted heteroaryl ring;
the bond between carbon 1 and carbon 2 may be a single bond or a double bond;
the bond between carbon 3 and carbon 4 may be a single bond or a double bond;
p is an integer from 0-3;
q is an integer from 1-3; and
r is an integer from 0-3,
with the proviso that in a compound of formula (II), if $R^{11}$, $R^{12}$, $R^{13}$, $R^{14}$, $R^{15}$, $R^{16}$, $R^{17}$, $R^{18}$, and $R^{19}$ are all H, the bond between carbon 1 and carbon 2 is a double bond, and q is 0, or 1 then Het cannot be 3-indolyl.

2. The compound of claim 1, wherein the compound is a compound of formula (I).

3. The compound of claim 2, wherein $R^1$, $R^2$, $R^3$, $R^4$, $R^5$, $R^6$, $R^7$, $R^8$, and $R^9$ are each H.

4. The compound of claim 1, wherein Het is selected from the group consisting of indolyl, azaindolyl, and thiazolyl, wherein the indolyl, azaindolyl, or thiazolyl group may be optionally substituted.

5. The compound of claim 1, wherein Het is selected from the group consisting of:

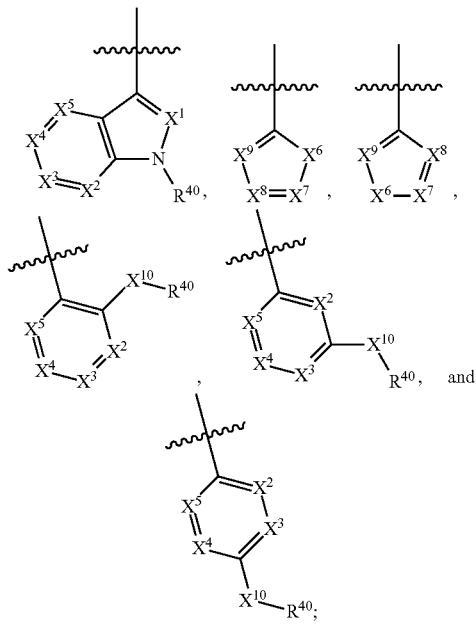

wherein $X^1$, $X^2$, $X^3$, $X^4$, $X^5$, $X^7$, $X^8$, and $X^9$ are each independently selected from the group consisting of N and $CR^{41}$;
$X^6$ and $X^{10}$ are each independently selected from the group consisting of S, O, $C(R^{42})_2$, and $NR^{43}$;
each occurrence of $R^{40}$, $R^{41}$, $R^{42}$, and $R^{43}$ is independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{44}$, $SR^{44}$, $S(=O)R^{44}$, $S(=O)_2R^{44}$, NHS$(=O)_2R^{44}$, $C(=O)R^{44}$, $OC(=O)R^{44}$, $CO_2R^{44}$, $OCO_2R^{44}CH(R^{44})_2$, $N(R^{44})_2$, $C(=O)N(R^{44})_2$, $OC(=O)N(R^{44})_2$, $NHC(=O)NH(R^{44})$, $NHC(=O)R^{44}$, $NHC(=O)OR^{44}$, $C(OH)(R^{44})_2$, and $C(NH_2)(R^{44})_2$; and
each occurrence of $R^{44}$ is independently selected from the group consisting of H and $C_1$-$C_6$ alkyl.

6. The compound of claim 5, wherein at least one of $X^1$, $X^2$, or $X^3$ is $NR^{41}$.

7. The compound of claim 5, wherein Het is selected from the group consisting of:

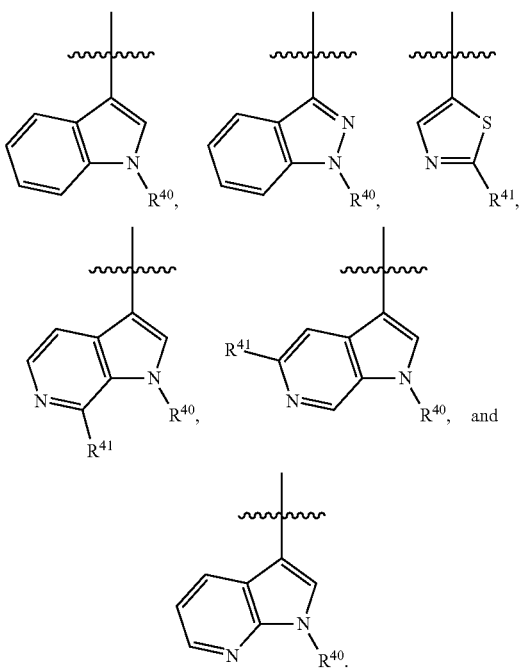

8. The compound of claim 2, wherein p is 1.

9. The compound of claim 1, wherein the compound is selected from the group consisting of:

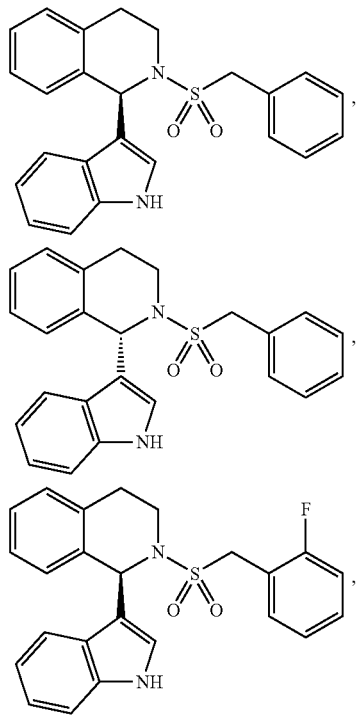

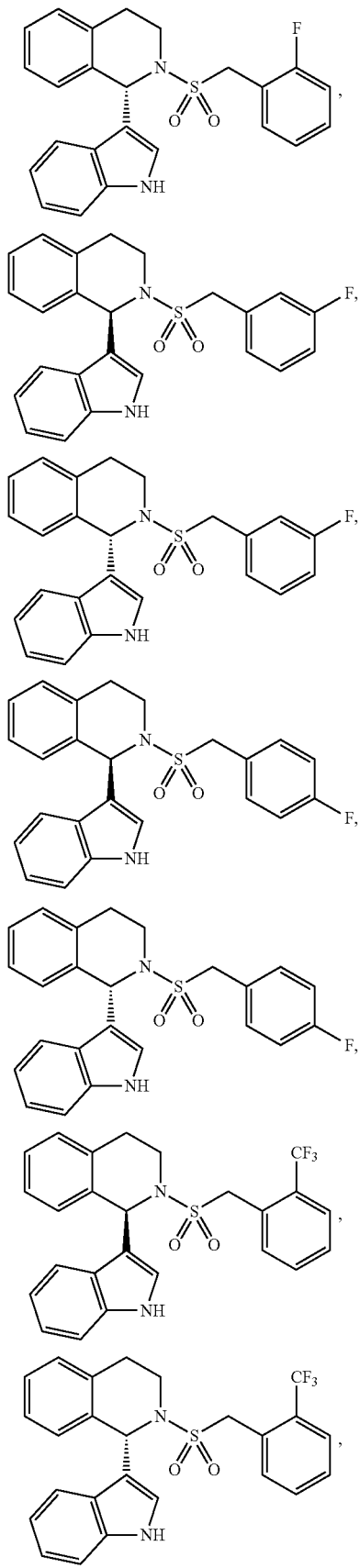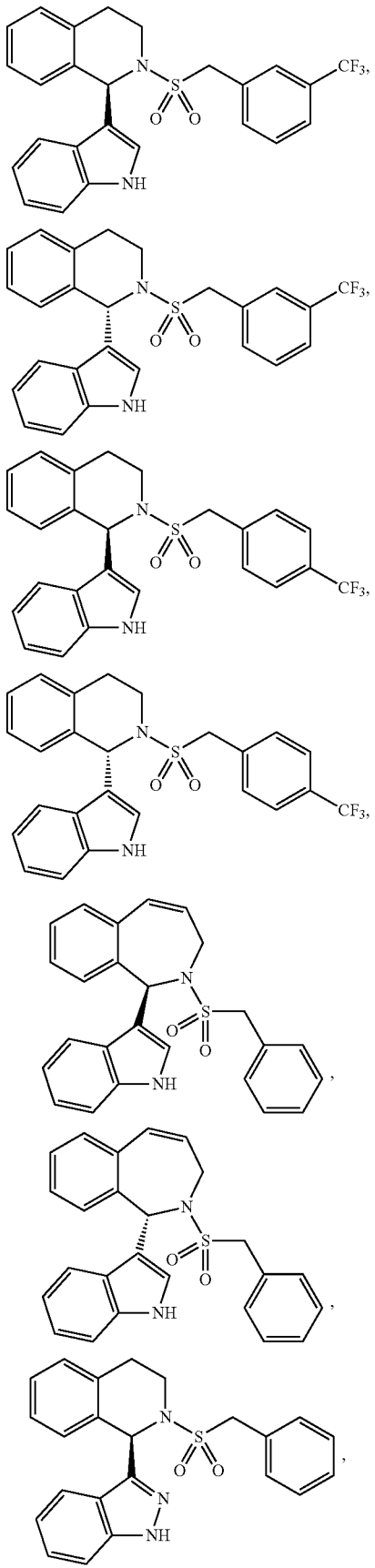

-continued

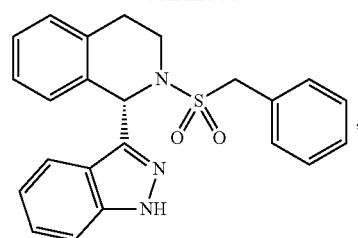

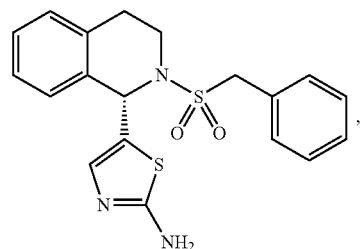

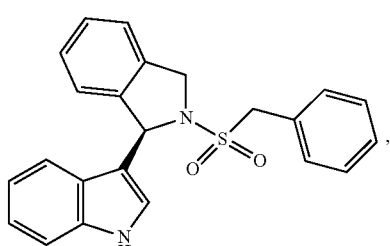

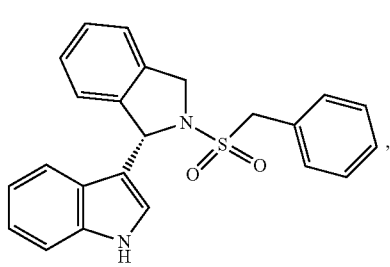

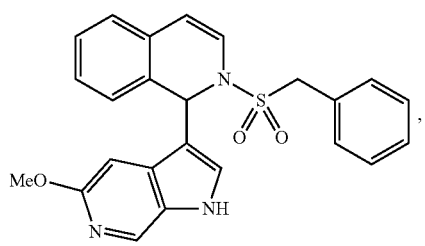

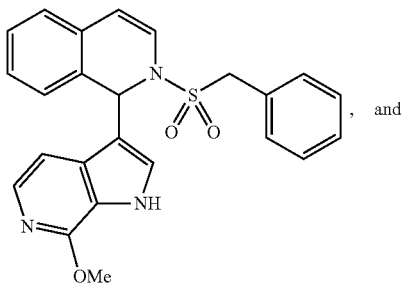

-continued

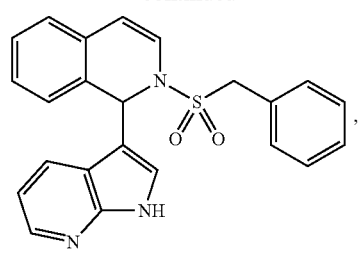

a salt or solvate, and any combinations thereof.

10. The compound of claim 1, wherein the compound is:

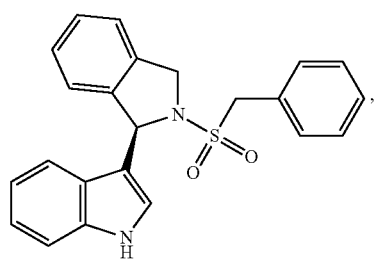 [SMILES: O=S(=O)(Cc1ccccc1)N1Cc2ccccc2[C@@H]1c1c[nH]c2ccccc12]

a salt or solvate, and any combinations thereof.

11. A pharmaceutical composition comprising at least one compound of claim 1.

12. A method of preventing or treating cancer in a subject in need thereof, the method comprising administering to the subject a therapeutically effective amount of a composition comprising a compound selected from the group consisting of formula (I), formula (II), and formula (III), a salt or solvate, and any combinations thereof:

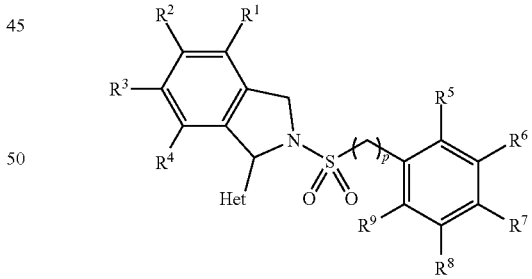

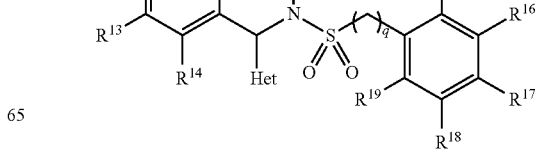

(III)

wherein:
R$^1$, R$^2$, R$^3$, R$^4$, R$^5$, R$^6$, R$^7$, R$^8$, R$^9$, R$^{11}$, R$^{12}$, R$^{13}$, R$^{14}$, R$^{15}$, R$^{16}$, R$^{17}$, R$^{18}$, R$^{19}$, R$^{21}$, R$^{22}$, R$^{23}$, R$^{24}$, R$^{25}$, R$^{26}$, R$^{27}$, R$^{28}$, and R$^{29}$ are each independently selected from the group consisting of H, C$_1$-C$_6$ alkyl, C$_1$-C$_6$ fluoroalkyl, C$_1$-C$_6$ heteroalkyl, F, Cl, Br, I, CN, NO$_2$, OR$^{30}$, SR$^{30}$, S(=O)R$^{30}$, S(=O)$_2$R$^{30}$, NHS(=O)$_2$R$^{30}$, C(=O)R$^{30}$, OC(=O)R$^{30}$, CO$_2$R$^{30}$, OCO$_2$R$^{30}$, CH(R$^{30}$)$_2$, N(R$^{30}$)$_2$, C(=O)N(R$^{30}$)$_2$, OC(=O)N(R$^{30}$)$_2$, NHC(=O)NH (R$^{30}$), NHC(=O)R$^{30}$, NHC(=O)OR$^{30}$, C(OH)(R$^{30}$)$_2$, and C(NH$_2$)(R$^{30}$)$_2$;

each occurrence of R$^{30}$ is independently selected from the group consisting of H and C$_1$-C$_6$ alkyl;

Het is a 5- to 14-membered substituted or unsubstituted heteroaryl ring;

the bond between carbon 1 and carbon 2 may be a single bond or a double bond;

the bond between carbon 3 and carbon 4 may be a single bond or a double bond;

p is an integer from 0-3;

q is an integer from 1-3; and r is an integer from 0-3, with the proviso that in a compound of formula (II), if R$^{11}$, R$^{12}$, R$^{13}$, R$^{14}$, R$^{15}$, R$^{16}$, R$^{17}$, R$^{18}$, and R$^{19}$ are all H, the bond between carbon 1 and carbon 2 is a double bond, and q is 0 or 1, then Het cannot be 3-indolyl.

13. The method of claim 12, wherein the compound is a compound of formula (I).

14. The method of claim 13, wherein R$^1$, R$^2$, R$^3$, R$^4$, R$^5$, R$^6$, R$^7$, R$^8$, and R$^9$ are each H.

15. The method of claim 12, wherein Het is selected from the group consisting of indolyl, azaindolyl, and thiazolyl, wherein the indolyl, azaindolyl, or thiazolyl group may be optionally substituted.

16. The method of claim 12, wherein Het is selected from the group consisting of:

wherein X$^1$, X$^2$, X$^3$, X$^4$, X$^5$, X$^7$, X$^8$, and X$^9$ are each independently selected from the group consisting of N and CR$^{41}$;

X$^6$ and X$^{10}$ are each independently selected from the group consisting of S, O, C(R$^{42}$)$_2$, and NR$^{43}$;

each occurrence of R$^{40}$, R$^{41}$, R$^{42}$, and R$^{43}$ is independently selected from the group consisting of H, C$_1$-C$_6$ alkyl, C$_1$-C$_6$ fluoroalkyl, C$_1$-C$_6$ heteroalkyl, F, Cl, Br, I, CN, NO$_2$, OR$^{44}$, SR$^{44}$, S(=O)R$^{44}$, S(=O)$_2$R$^{44}$, NHS(=O)$_2$R$^{44}$, C(=O)R$^{44}$, OC(=O)R$^{44}$, CO$_2$R$^{44}$, OCO$_2$R$^{44}$, CH(R$^{44}$)$_2$, N(R$^{44}$)$_2$, C(=O)N(R$^{44}$)$_2$, OC(=O)N(R$^{44}$)$_2$, NHC(=O)NH(R$^{44}$), NHC(=O)R$^{44}$, NHC(=O)OR$^{44}$, C(OH)(R$^{44}$)$_2$, and C(NH$_2$)(R$^{44}$)$_2$; and each occurrence of R$^{44}$ is independently selected from the group consisting of H and C$_1$-C$_6$ alkyl.

17. The method of claim 16, wherein at least one of X$^1$, X$^2$, or X$^3$ is NR$^{41}$.

18. The method of claim 16, wherein Het is selected from the group consisting of:

19. The method of claim 13, wherein p is 1.

20. The method of claim 12, wherein the compound is:

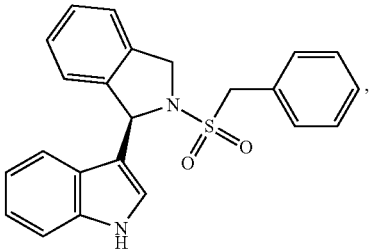 [SMILES: O=S(=O)(Cc1ccccc1)N1Cc2ccccc2[C@@H]1c1c[nH]c2ccccc12]

a salt or solvate and any combinations thereof.

21. A compound selected from the group consisting of formula (I) and formula (III), a salt or solvate, and any combinations thereof:

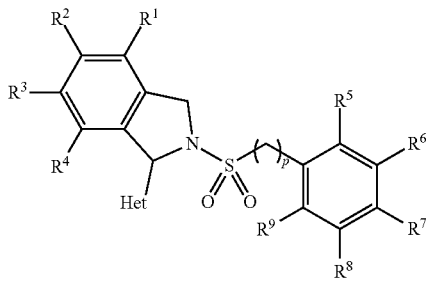

(I)

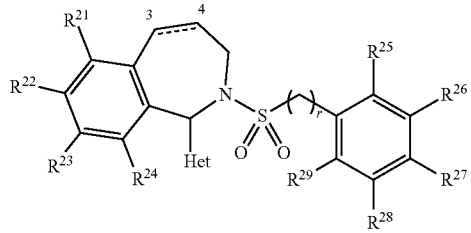

(III)

wherein:
$R^1, R^2, R^3, R^4, R^5, R^6, R^7, R^8, R^9, R^{21}, R^{22}, R^{23}, R^{24}, R^{25}, R^{26}, R^{27}, R^{28}$, and $R^{29}$ are each independently selected from the group consisting of H, $C_1$-$C_6$ alkyl, $C_1$-$C_6$ fluoroalkyl, $C_1$-$C_6$ heteroalkyl, F, Cl, Br, I, CN, $NO_2$, $OR^{30}$, $SR^{30}$, $S(=O)R^{30}$, $S(=O)_2R^{30}$, $NHS(=O)_2R^{30}$, $C(=O)R^{30}$, $OC(=O)R^{30}$, $CO_2R^{30}$, $OCO_2R^{30}$, $CH(R^{30})_2$, $N(R^{30})_2$, $C(=O)N(R^{30})_2$, $OC(=O)N(R^{30})_2$, $NHC(=O)NH(R^{30})$, $NHC(=O)R^{30}$, $NHC(=O)OR^{30}$, $C(OH)(R^{30})_2$, and $C(NH_2)(R^{30})_2$;

each occurrence of $R^{30}$ is independently selected from the group consisting of H and $C_1$-$C_6$ alkyl;

Het is a 5- to 14-membered substituted or unsubstituted heteroaryl ring;

the bond between carbon 3 and carbon 4 may be a single bond or a double bond;

p is an integer from 0-3; and r is an integer from 0-3.

* * * * *